United States Patent
Alkhatib et al.

(10) Patent No.: US 12,396,845 B2
(45) Date of Patent: Aug. 26, 2025

(54) FABRIC MATERIAL FOR MEDICAL DEVICES

(71) Applicant: Abbott Laboratories, Abbott Park, IL (US)

(72) Inventors: Yousef F. Alkhatib, Edina, MN (US); Jay Reimer, Saint Paul, MN (US); Paul E. Ashworth, Danbury, WI (US); Keith T. High, White Bear Lake, MN (US); Richard Kaleta, Arden Hills, MN (US); Ryan Finn, Roseville, MN (US)

(73) Assignee: Abbott Laboratories, Abbott Park, IL (US)

( * ) Notice: Subject to any disclaimer, the term of this patent is extended or adjusted under 35 U.S.C. 154(b) by 479 days.

(21) Appl. No.: 16/713,356

(22) Filed: Dec. 13, 2019

(65) Prior Publication Data

US 2020/0188098 A1 Jun. 18, 2020

Related U.S. Application Data

(60) Provisional application No. 62/925,402, filed on Oct. 24, 2019, provisional application No. 62/925,412, filed on Oct. 24, 2019, provisional application No. 62/925,391, filed on Oct. 24, 2019, provisional application No. 62/925,379, filed on Oct. 24, 2019, (Continued)

(51) Int. Cl.
 *A61F 2/24* (2006.01)

(52) U.S. Cl.
 CPC .......... *A61F 2/2418* (2013.01); *A61F 2/2409* (2013.01); *A61F 2210/0076* (2013.01); *A61F 2250/0015* (2013.01); *A61F 2250/0028* (2013.01); *A61F 2310/00005* (2013.01); *A61F 2310/00389* (2013.01)

(58) Field of Classification Search
 CPC ........................................................ A61F 2/24
 See application file for complete search history.

(56) References Cited

U.S. PATENT DOCUMENTS

| 2,852,811 A | 9/1958 | Petriello |
| 3,657,744 A | 4/1972 | Ersek |
| 4,056,854 A | 11/1977 | Boretos et al. |

(Continued)

FOREIGN PATENT DOCUMENTS

| EP | 2435250 A1 | 4/2012 |
| EP | 2926766 A1 | 10/2015 |

(Continued)

OTHER PUBLICATIONS

Basir et al., "Flexible mechanoprosthesis made from woven ultra-high-molecular-weight polyethylene fibers: proof of concept in a chronic sheep model"; Interactive CardioVascular and Thoracic Surgery, Dec. 1, 2017, pp. 942-949, vol. 25, No. 6.

(Continued)

*Primary Examiner* — Jacqueline Woznicki

(74) *Attorney, Agent, or Firm* — SLEMAN & LUND LLP

(57) ABSTRACT

At least a portion of fabrics for use in medical devices is formed from polymeric materials. The fabrics may be uncoated, partially coated or fully coated with one or more layers of a polymer. The fabrics may be used for the leaflets and/or cuffs of prosthetic heart valves and as a component of other medical devices.

14 Claims, 36 Drawing Sheets

Related U.S. Application Data provisional application No. 62/779,176, filed on Dec. 13, 2018.

(56) References Cited

U.S. PATENT DOCUMENTS

| | | | |
|---|---|---|---|
| 4,222,126 A | 9/1980 | Boretos | |
| 4,610,688 A | 9/1986 | Silvestrini et al. | |
| 4,610,918 A | 9/1986 | Effenberger et al. | |
| 4,876,049 A | 10/1989 | Aoyama et al. | |
| 5,411,552 A | 5/1995 | Andersen et al. | |
| 5,545,214 A | 8/1996 | Stevens | |
| 5,855,601 A | 1/1999 | Bessler et al. | |
| 5,957,948 A | 9/1999 | Mariant | |
| 5,957,949 A | 9/1999 | Leonhardt et al. | |
| 6,458,153 B1 | 10/2002 | Bailey et al. | |
| 6,540,782 B1 | 4/2003 | Snyders | |
| 6,821,297 B2 | 11/2004 | Snyders | |
| 7,109,135 B2 | 9/2006 | Taghavi | |
| 7,393,360 B2 | 7/2008 | Spenser et al. | |
| 7,510,575 B2 | 3/2009 | Spenser et al. | |
| 7,530,253 B2 | 5/2009 | Spenser et al. | |
| 7,585,321 B2 | 9/2009 | Cribier | |
| 7,682,390 B2 | 3/2010 | Seguin | |
| 7,923,094 B1 | 4/2011 | Harding et al. | |
| 8,758,389 B2 | 6/2014 | Glimsdale | |
| 8,992,608 B2 | 3/2015 | Haug et al. | |
| 9,056,006 B2 | 6/2015 | Edelman et al. | |
| 9,241,794 B2 | 1/2016 | Braido et al. | |
| 9,289,296 B2 | 3/2016 | Braido et al. | |
| 9,326,856 B2 | 5/2016 | Schraut et al. | |
| 9,629,714 B2 | 4/2017 | Letac et al. | |
| 10,022,211 B2 | 7/2018 | Braido et al. | |
| 10,039,640 B2 | 8/2018 | Grundeman et al. | |
| 10,052,204 B2 | 8/2018 | McLean et al. | |
| 10,299,915 B2 | 5/2019 | Edelman et al. | |
| 2001/0021872 A1 | 9/2001 | Bailey | |
| 2003/0078652 A1* | 4/2003 | Sutherland | A61F 2/2412 623/2.12 |
| 2003/0209835 A1 | 11/2003 | Chun | |
| 2004/0088046 A1* | 5/2004 | Speziali | A61F 2/2415 623/2.15 |
| 2005/0137682 A1 | 6/2005 | Justino | |
| 2006/0190074 A1* | 8/2006 | Hill | A61F 2/2475 623/2.18 |
| 2006/0235511 A1 | 10/2006 | Osborne | |
| 2008/0020182 A1 | 1/2008 | Gregg et al. | |
| 2009/0105813 A1* | 4/2009 | Chambers | A61F 2/2475 623/2.38 |
| 2009/0117334 A1 | 5/2009 | Sogard | |
| 2010/0094392 A1 | 4/2010 | Nguyen | |
| 2012/0078352 A1 | 3/2012 | Wang et al. | |
| 2012/0171917 A1 | 7/2012 | Rasmussen | |
| 2013/0150956 A1* | 6/2013 | Yohanan | A61F 2/2418 623/2.14 |
| 2013/0197631 A1 | 8/2013 | Bruchman | |
| 2014/0005771 A1* | 1/2014 | Braido | A61F 2/2418 623/2.12 |
| 2014/0005772 A1* | 1/2014 | Edelman | A61F 2/2415 623/2.17 |
| 2014/0107772 A1* | 4/2014 | Li | A61F 2/2418 29/428 |
| 2014/0249567 A1 | 9/2014 | Adams et al. | |
| 2014/0277417 A1* | 9/2014 | Schraut | A61F 2/2418 623/2.17 |
| 2015/0091219 A1* | 4/2015 | Munnelly | A61F 2/2415 264/479 |
| 2015/0127100 A1 | 5/2015 | Braido et al. | |
| 2015/0157455 A1* | 6/2015 | Hoang | B29C 49/26 264/269 |
| 2015/0157456 A1* | 6/2015 | Armstrong | A61F 2/2418 29/467 |
| 2015/0182332 A1* | 7/2015 | Edelman | B05B 7/0433 623/2.17 |
| 2015/0223932 A1 | 8/2015 | Dixon | |
| 2015/0320556 A1 | 11/2015 | Levi et al. | |
| 2016/0100939 A1 | 4/2016 | Armstrong | |
| 2016/0220359 A1* | 8/2016 | Backus | A61F 2/2409 |
| 2016/0220360 A1* | 8/2016 | Lin | A61F 2/2418 |
| 2017/0014227 A1* | 1/2017 | Boden | A61F 2/2412 |
| 2017/0065408 A1 | 3/2017 | Grundeman et al. | |
| 2017/0071729 A1 | 3/2017 | Wrobel | |
| 2017/0086971 A1 | 3/2017 | Braido et al. | |
| 2017/0189175 A1* | 7/2017 | Justino | A61F 2/2418 |
| 2017/0196688 A1 | 7/2017 | Christianson et al. | |
| 2017/0258585 A1 | 9/2017 | Marquez et al. | |
| 2017/0296332 A1 | 10/2017 | Harder | |
| 2017/0325944 A1 | 11/2017 | Erzberger et al. | |
| 2018/0055631 A1 | 3/2018 | Morin et al. | |
| 2018/0055632 A1 | 3/2018 | Hill et al. | |
| 2018/0078368 A1 | 3/2018 | Vidlund et al. | |
| 2018/0116780 A1 | 5/2018 | Laine | |
| 2018/0133003 A1* | 5/2018 | Levi | A61F 2/2418 |
| 2018/0296341 A1 | 10/2018 | Noe et al. | |
| 2019/0015192 A1 | 1/2019 | Nakazawa | |
| 2019/0117387 A1* | 4/2019 | Li | A61F 2/246 |
| 2019/0117390 A1 | 4/2019 | Neethling et al. | |
| 2019/0201190 A1 | 7/2019 | Dakin et al. | |
| 2019/0314154 A1* | 10/2019 | Armstrong | A61F 2/2418 |
| 2019/0328525 A1 | 10/2019 | Noe et al. | |
| 2019/0351099 A1* | 11/2019 | McCarthy | A61L 31/129 |
| 2020/0022807 A1* | 1/2020 | Karciauskas | A61F 2/2418 |
| 2020/0093590 A1 | 3/2020 | Reimer et al. | |
| 2020/0188095 A1 | 6/2020 | Liu | |
| 2021/0045868 A1* | 2/2021 | Reimer | D03D 15/283 |
| 2021/0121290 A1* | 4/2021 | Alkhatib | A61F 2/2415 |
| 2021/0315690 A1 | 10/2021 | Morin | |
| 2021/0393400 A1* | 12/2021 | Alkhatib | A61F 2/2409 |

FOREIGN PATENT DOCUMENTS

| | | |
|---|---|---|
| EP | 2949292 A1 | 12/2015 |
| EP | 2926766 B1 | 2/2016 |
| WO | 0224119 A1 | 3/2002 |
| WO | 2010138143 A1 | 12/2010 |
| WO | 2015169870 | 11/2015 |
| WO | 2018121341 A1 | 7/2018 |
| WO | 2020123945 | 6/2020 |

OTHER PUBLICATIONS

International Search Report including the Written Opinion from Application No. PCT/US2020/037239 mailed Mar. 11, 2020, 16 pages.

Yamagishi M, Kurosawa H., "Outflow Reconstruction of Tetralogy of Fallot Using a Gore-Tex Valve," The Annals of Thoracic Surgery, Dec. 1, 1993, pp. 1411-1416, vol. 56, No. 6.

International Search Report including the Written Opinion from Application No. PCT/US2019/066237 mailed Mar. 3, 2020, 13 pages.

Plain weave, Encyclopaedia Brittanica, Dec. 17, 2010, <https://www.britannica.com/technology/plain-weave> accessed on Oct. 11, 2019.

Watson, Kate Heintz et al., Textiles and Clothing, 1907, Home Economics Association, p. 77.

Difference between Warp Rib Weave and Weft Rib Weave, Define Textile, 2019, <http://www.definetextile.com/2013/05/difference-between-warp-rib-weave-and.html>, accessed on Oct. 23, 2019.

Twill weave, 2019, <https://www.dictionary.com/browse/twill-weave>, accessed on Oct. 11, 2019.

What is a Herringbone Weave?, Shirts of Holland B.V., 2019, <https://sleeve7.com/blog/what-is-a-herringbone-weave/>, accessed on Oct. 11, 2019.

Basic Weaves, Cotton Incorporated, 2019, <https://www.cottonworks.com/topics/sourcing-manufacturing/weaving/the-art-of-weaving-basic-weaves/>, accessed on Oct. 11, 2019.

Leno Weaves, Serial 512. Ed. 1., International Textbook Co., <https://www2.cs.arizona.edu/patterns/weaving/monographs/ics512.pdf>, accessed on Oct. 11, 2019.

(56) References Cited

OTHER PUBLICATIONS

Bedford Cords, TextileSchool4U.Blogspot.com, 2013, http://textileschool4u.blogspot.com/2013/12/bedford-cords.html, accessed on Oct. 11, 2019.
Honeycomb, The Free Dictionary, <https://www.thefreedictionary.com/waffle+weave>, accessed on Oct. 11, 2019.
Adam Augustyn, Weaving, 2008, <https://www.britannica.com/technology/weaving#ref290551, accessed on Oct. 11, 2019.
Tapestry Weaving Basics, 2019, <https://www.mirrixlooms.com/pages/> tapestryweaving-basics, accessed on Oct. 11, 2019.
Double Cloth, Mar. 20, 2019, https://en.wikipedia.org/wiki/Double_cloth#cite_ref-text_2-0 <https://en.wikipedia.org/wiki/Double_cloth>, accessed on Oct. 11, 2019.
<https://www.thefreedictionary.com/single-knit> ; accessed Jul. 24, 2020.
Rib-Knit, Merriam-Webster, 2019, <https://www.merriam-webster.com> /dictionary/rib-knit, accessed on Oct. 11, 2019.
Warp knitting, Sep. 15, 2019, <https://en.wikipedia.org/wiki/> Warp_knitting, accessed on Oct. 11, 2019.
Basir et al., "Flexible mechanoprosthesis made from woven ultra-high-molecular-weight polyethylene fibers: proof of concept in a chronic sheep model"; Interactive CardioVascular and Thoracic Surgery, 25(2017) 942-949.
Yamagishi M, Kurosawa H. Outflow reconstruction of tetralogy of Fallot using a Gore-Tex valve. The Annals of thoracic surgery. Dec. 1, 1993;56(6):1414-6.
<https://www.thefreedictionary.com/double-knit> ; accessed Jul. 24, 2020.

\* cited by examiner

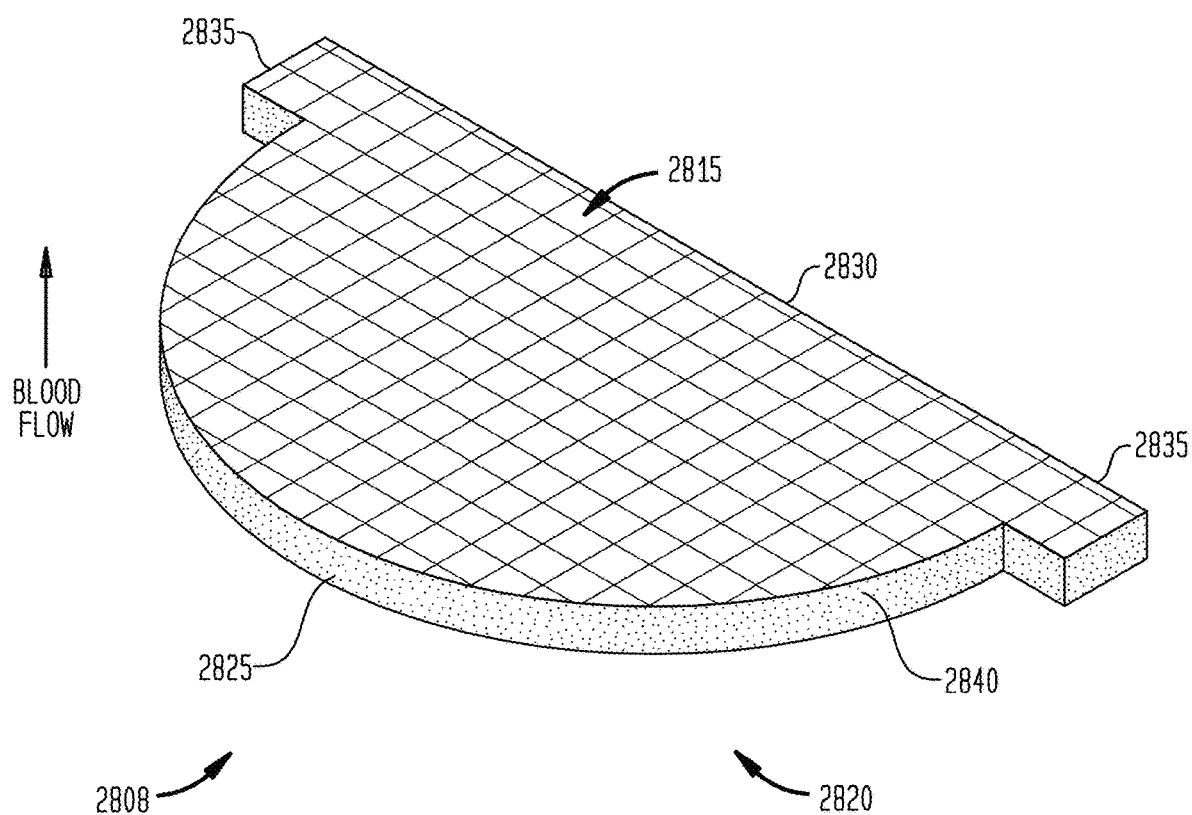

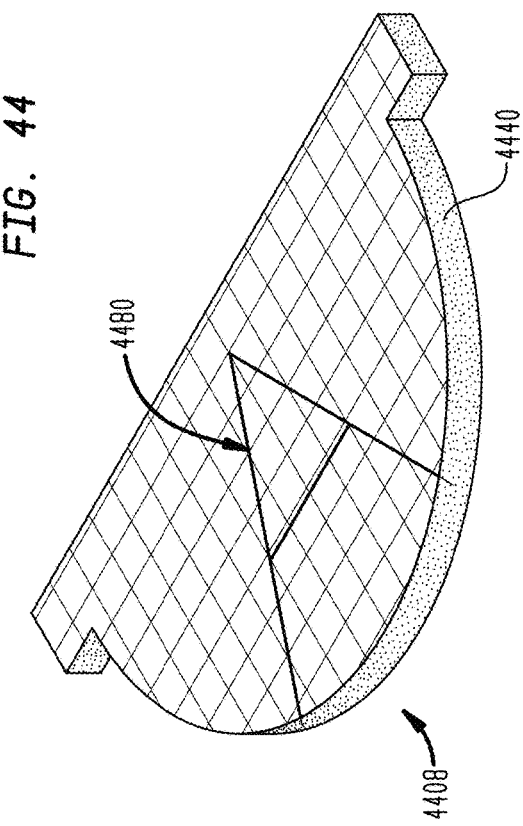
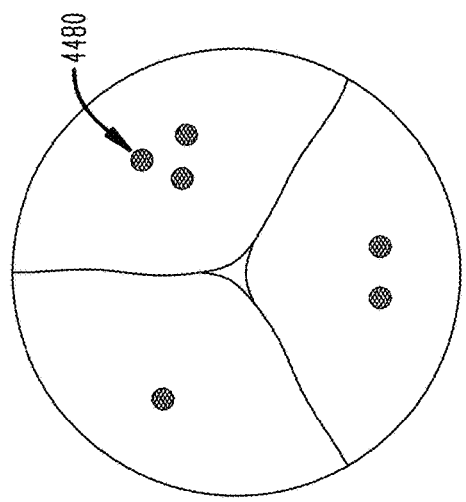
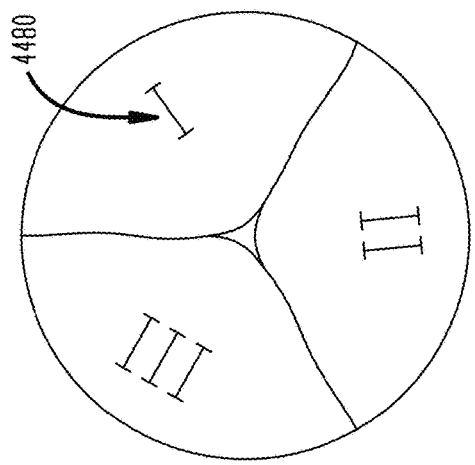
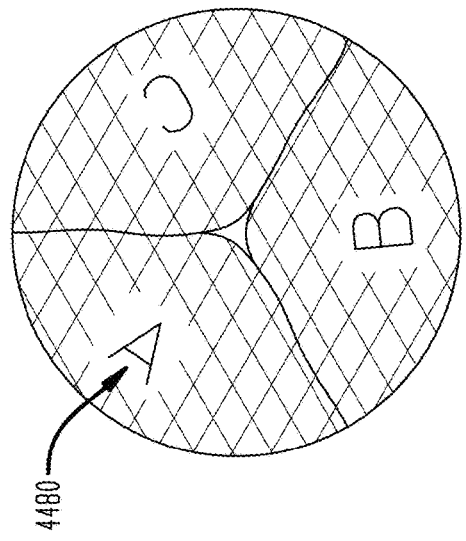
FIG. 44
FIG. 44A
FIG. 44B
FIG. 44C

FABRIC MATERIAL FOR MEDICAL DEVICES

CROSS-REFERENCE TO RELATED APPLICATIONS

The present application claims the benefit of the filing dates of U.S. Provisional Patent Application Nos. 62/779,176, filed Dec. 13, 2018; 62/925,379, filed Oct. 24, 2019; 62/925,391, filed Oct. 24, 2019; 62/925,402, filed Oct. 24, 2019; and 62/925,412, filed Oct. 24, 2019, the disclosures of all of which are hereby incorporated by reference herein.

BACKGROUND OF THE DISCLOSURE

The present disclosure relates to synthetic fabric materials that can be used in various medical devices and the medical devices including the synthetic fabric materials. For purposes of discussing the state of the art, however, prosthetic heart valves, and particularly collapsible/expandable prosthetic heart valves useful for delivery through a catheter or trocar, will be exemplified.

Prosthetic heart valves, including surgical heart valves and collapsible/expandable heart valves intended for transcatheter aortic valve replacement ("TAVR") or transcatheter mitral valve replacement ("TMVR"), are well known in the patent literature. (See U.S. Pat. Nos. 3,657,744; 4,056,854; 5,411,552; 5,545,214; 5,855,601; 5,957,948; 6,458,153; 6,540,782; 7,510,575; 7,585,321; 7,682,390; and 9,326,856; and U.S. Pub. No. 2015/0320556.) Surgical or mechanical heart valves may be sutured into a native annulus of a patient during an open-heart surgical procedure, for example. Collapsible/expandable heart valves may be delivered into a patient via a tube-like delivery apparatus such as a catheter, a trocar, a laparoscopic instrument, or the like to avoid a more invasive procedure such as full open-chest, open-heart surgery. As used herein, reference to a "collapsible/expandable" heart valve includes heart valves that are formed with a small cross-section that enables them to be delivered into a patient through a tube-like delivery apparatus in a minimally invasive procedure, and then expanded to an operable once in place, as well as heart valves that, after construction, are first collapsed to a small cross-section for delivery into a patient and then expanded to an operable size once in place.

Collapsible/expandable prosthetic heart valves typically take the form of a one-way valve structure (often referred to herein as a valve assembly) mounted to/within an expandable stent. In general, these collapsible/expandable heart valves include a self-expanding or balloon-expandable stent, often made of nitinol or steel. The one-way valve assembly mounted to/within the stent includes one or more leaflets, and may also include a cuff or skirt. The cuff may be disposed on the stent's interior or luminal surface, its exterior or abluminal surface, and/or on both surfaces. (See U.S. Pat. Nos. 6,458,153; 7,585,321; 8,992,608; 9,241,794; and 9,289,296; and U.S. Pub. No. 2015/0320556.) A cuff ensures that blood does not just flow around the valve leaflets if the valve or valve assembly are not optimally seated in a valve annulus. A cuff, or a portion of a cuff disposed on the exterior of the stent, can help retard leakage around the outside of the valve (the latter known as paravalvular leakage or "PV" leakage).

Leaflets, cuffs and valve assemblies for prosthetic heart valves may be derived from various natural tissues or synthetic materials. Commercial natural tissues that have been chemically treated or "fixed" are often used. For example, leaflets could be made of bovine pericardium and cuffs could be made of porcine pericardium. (See, e.g., U.S. Pat. Nos. 5,957,949 at 6:23-33; U.S. Ser. No. 6,458,153 at 8:28-40; U.S. Ser. No. 5,855,601 at 6:21-30; and U.S. Ser. No. 7,585,321 at 13:5-36.) Other materials that may be used include various synthetic polymers including, without limitation, polytetrafluoroethylene (PTFE) or polyester (see U.S. Pat. Nos. 5,855,601 at 6:29-31; U.S. Ser. Nos. 10,039,640; 10,022,211; 9,056,006; and 10,299,915; and U.S. Pub. Nos. 2018/0055632; 2017/0258585; 2018/0078368; and 2019/0201190), and elastic materials including silicone rubber and polyurethanes. (See U.S. Pat. No. 6,540,782 at 6:2-5.) These materials have been used in the form of continuous sheets, porous felts (U.S. Pat. No. 6,540,782 at 6:17-23) or woven fabrics. (See also U.S. Pat. Nos. 10,039,640; 10,299,915; 10,022,211; and 4,610,688; and U.S. Pub. Nos. 2018/0055632; 2017/0258585; and 2018/0078368.) Valve components and valve assemblies may be attached to a collapsible/expandable stent or frame by sutures or may be molded, glued, or soldered to the stent. (See U.S. Pat. No. 7,585,321 at 13:30-31.)

Despite the disclosure of various natural tissues and synthetic materials for possible uses in various medical devices, little is often disclosed about the specifics of the structure and compositions of such elements beyond illustrations of their general structure and a generic identification of polymers that can be used. Those generalized disclosures show that, while the concept of polymer-based implantable medical devices, and in particular valves, is known, actually successfully taking the broad concept to working solutions is far more challenging. Therefore, there exists a need for further improvements in the materials for these devices and the devices made therefrom.

BRIEF SUMMARY OF THE DISCLOSURE

The disclosure describes polymer-containing fabric materials that may be used for construction of medical devices including, without limitation: venous valves, occluders, prosthetic vascular conduits, grafts, and embolic protection devices, fabrics for treating hernias, skin patches, vaginal patches, cardiac patches, adhesion barriers, surgical heart valves (those requiring open chest surgery to implant) and collapsible/expandable prosthetic heart valves which can be implanted using a catheter such as trans-femorally, trans-apically, and trans-septally. The disclosure also describes and contemplates the medical devices made using these polymer-containing fabric materials as well as methods of making the fabric materials and the medical devices.

The polymeric fabric materials include uncoated fabrics and coated fabrics. Fabrics are made from interlaced fibers and include, inter alia, woven fabrics, knitted fabrics, felts, other non-woven mats and the like. The fabric materials described herein include at least some synthetic fibers, such as, for example, fibers made from polyolefins such as polytetrafluoroethylene (PTFE) (which includes expanded and stretched PTFE and PTFE of any molecular weight) (also known as Teflon®), polyethylenes including those of any molecular weight (e.g., ultra-high molecular weight polyethylene (UHMWPE)), and polypropylenes including those of any molecular weight (e.g., ultra-high molecular weight polypropylene (UHMWPP), as well as polyurethanes, PEEK, polyvinyl alcohols, silicones, rayons, polyesters, aramids, spandex, or combinations, blends and copolymers thereof.

The uncoated fabric may have at least one of the following properties: a thread count of at least about 150 fibers per square inch, and the thread count need not be symmetrical; a high density weave of generally at least 300 fibers or more per square inch; a tensile strength of at least 50N and in some embodiments, 100 N or more; and/or an areal density of between 0.5 and 1.3 ounces/yard$^2$ (the areal density being the mass of the fabric per square yard). The uncoated fabric may have a thickness of between about 10 μm and about 200 μm. The fabric may also control (facilitate or retard) cell attachment and proliferation.

In some embodiments the polymeric fabric may be coated with at least one polymer layer to form a coated fabric. "Coated" as used herein means that the fabric has a polymer applied to at least a portion of it after the fabric has otherwise been formed. Coatings may be formed of a single polymer layer, multiple polymer layers, and/or patterns of discrete polymer layers on one or more surfaces of the fabric. Where multiple polymer coatings are used, they may be the same or different in terms of thickness, composition, number of layers and/or location. In some embodiments, the polymer coating may provide improved or altered properties to the fabric relative to the uncoated fabric. These altered properties may include, without limitation, one or more of: (1) adjusting the porosity of the fabric, (2) adjusting surface roughness, (3) altering strength, abrasion resistance, and/or flexibility, (4) altering lubricity, (5) providing weight or rigidity to portions of the fabric, (6) promoting folding in specific regions, (7) altering cell adhesion to the fabric, and (8) retention or release of a therapeutic agent.

The polymers which may be used for the coatings include all of those previously identified for use for the fabric. In addition, in some embodiments, the polymer coating can be bioabsorbable, biodegradable, and/or bio-erodible. Exemplary bioabsorbable, biodegradable, and/or bio-erodible polymers may include poly-glycolic acid, poly-L-lactic acid, copolymers of poly-glycolic acid, poly-L-lactic acid, poly-caprolactone, poly-DL lactic acid, polytrimethylene carbonate, polydioxanone, poliglecaprone and polyglactin. Such bioabsorbable, biodegradable, and/or bio-erodible polymers may be provided as a coating on a surface in a thickness sufficient to delay tissue growth on the coated surface.

A single polymer coating layer may be used on one major surface of a fabric layer or multiple layers of the same or different polymer materials may be used on both major surfaces. Indeed, up to about 20 layers may be used on any surface or edge of the fabric. The total thickness of all such coatings can range from a minimum of about 0.50 μm to a maximum of about 100 μm per side of the fabric.

The coating may also be a partial coating and/or a contoured coating. Partially coated means that some portion of a major surface or edge is uncoated while other portions are coated. Contoured surfaces may be coated completely, but to different thicknesses or degrees. Either or both may be used to provide specific structural features to a side or edge of a coated fabric, to provide different patterns, and the like. Partial coatings may alter flexibility, provide extra resistance against wear from contact, can add weight, can help maintain a desired shape, can help prevent fraying or unravelling of the fabric, facilitate attachment, add strength, etc., to a localized area of the fabric and any structure made from that fabric. Coated (including partially coated) and uncoated fabrics may be provided with grommets to facilitate attachment while reducing damage that can come from the use of, for example, sutures. Coated and uncoated fabrics may also be constructed with indicia to assist in placement or confirming operability during surgery. Structures made from uncoated fabrics, coated fabrics, and partially coated fabrics include, without limitation: the elements of a valve assembly used in a collapsible/expandable heart valve such as interior cuffs, exterior cuffs, and leaflets.

Another embodiment of the disclosure provides a method of manufacturing a collapsible/expandable valve prosthesis that includes providing an uncoated polymeric fabric as just discussed having a top surface and a bottom surface (first and second major surfaces); providing a polymer such as, without limitation, an ultra-high molecular weight polyolefin; and applying the polymer to the top surface and/or the bottom surface of the fabric to form a coated fabric. This application process may form the layer directly on the fabric or involve the application of a pre-prepared film to the fabric. For example, one or more polymer films may be laminated to one or more surfaces of a fabric by gluing or the application of heat and/or pressure. A polymer layer may also be formed on the fabric by applying a liquid polymer material to a surface of the fabric and allowing it to solidify, cross-link, or otherwise become an adhered layer. This may be done by, for example, spray coating a polymer on one or more sides of the fabric, dip coating the fabric, and the like. Other techniques for applying the polymer coating include, for example, 3D printing. Partial coatings may be applied to a limited portion of the fabric as just discussed or may be formed by applying a complete coating to the fabric and removing portions by, for example, ablation.

The fabric and any medical device made using that fabric may undergo sterilization. This may be done with a variety of sterilization modalities, for example, with ethylene oxide, peracetic acid, nitrogen oxide, e-beam, steam, gamma radiation, carbon dioxide and chemical liquid sterilant.

Various methods of forming the components of medical devices, including valve components and valve assemblies, may be used. These include mechanical methods, for example cutting with scissors or a blade. Other techniques include, for example, cautery; stamping; chemical, laser, ultrasonic, or water jet cutting, bio-glue, folding or lamination.

One embodiment of a useful coated, partially coated or uncoated fabric is a high density weave of a polyethylene, a polypropylene or a PTFE, or blends or copolymers thereof, the fabric having a thread count of 300-500×100-300 fibers per square inch, a tensile strength of at least 65N, an areal density of at least 0.65±0.1 ounces/yard$^2$, and a thickness of approximately 50-100 μm.

In another embodiment, a useful coated, partially coated or uncoated fabric is a high density weave of UHMWPE, UHMWPP or UHMWPTFE, or blends or copolymers thereof, the fabric having a thread count of 300-500×100-300 fibers per square inch, a tensile strength of at least 65N, an areal density of at least 0.5±0.1 ounces/yard$^2$, and a thickness of approximately 20-200 μm.

In another embodiment, a useful coated, partially or uncoated fabric is a high density weave of ultra-high molecular weight polyethylene having a thread count of 440×220 fibers per square inch. In a particular embodiment, the uncoated fabric has a tensile strength of at least about 75N, an areal density of at least 0.65±0.1 ounces/yard$^2$, and a maximum thickness of approximately 50-100 μm.

In another embodiment, a useful coated, partially coated or uncoated fabric is a high density weave of ultra-high molecular weight polyethylene having a thread count of 440×220 fibers per square inch. In a particular embodiment, the uncoated fabric has a tensile strength of at least about 75N, an areal density of at least 0.5±0.05 ounces/yard$^2$, and a thickness of approximately 50-100 μm.

In another embodiment, a useful coated, partially coated or uncoated fabric is a high density weave of ultra-high molecular weight polyethylene having a thread count of 300-500×100-300 fibers per square inch. In a particular embodiment, the uncoated fabric has a tensile strength of at least 75N, an areal density of about 0.8±0.05 ounces/yard$^2$, and a thickness of approximately 76 μm.

In another embodiment, a useful coated, partially coated or uncoated fabric is a high density weave of ultra-high molecular weight polyethylene having a thread count of 440×220 fibers per square inch. In a particular embodiment, the uncoated fabric has a tensile strength of at least about 75N, an areal density of at least 0.65±0.05 ounces/yard$^2$, and a thickness of approximately 50 μm.

In another embodiment, a useful coated or partially coated fabric is a high density weave of PE or PTFE having a thread count of 300-500×100-300 fibers per square inch. In a particular embodiment, the uncoated fabric has a tensile strength of at least about 75N, an areal density of at least 0.65±0.05 ounces/yard$^2$, and a thickness of approximately 250 μm or less.

BRIEF DESCRIPTION OF THE DRAWINGS

This disclosure may be best understood by reference to the following description taken in conjunction with the accompanying drawing figures in which:

FIG. 28 is a schematic perspective view of a leaflet formed from an uncoated fabric according to the present disclosure;

FIG. 44 is a schematic perspective view of a leaflet formed from another uncoated fabric incorporating indicia according to the present disclosure;

FIGS. 44A-44C are highly schematic transverse cross-sections of a prosthetic heart valve incorporating a plurality of the leaflets of FIG. 44 with different indicia;

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the terms "proximal" and "upstream" refer to the inflow end of a prosthetic heart valve and these terms may be used interchangeably. The terms "distal" and "downstream" refer to the outflow end of a prosthetic heart valve and also may be used interchangeably. As used herein, the terms "generally," "substantially," and "about" are intended to mean that slight deviations from absolute are included within the scope of the term so modified. When used herein in the context of a prosthetic heart valve, or a component thereof, the lengthwise or axial direction refers to a direction parallel to a longitudinal axis passing through the center of the stent or heart valve from the inflow end to the outflow end. When used herein in the context of a prosthetic heart valve, or a component thereof, the circumferential direction refers to a direction extending along the circumference of the prosthetic heart valve.

Figure 1A:
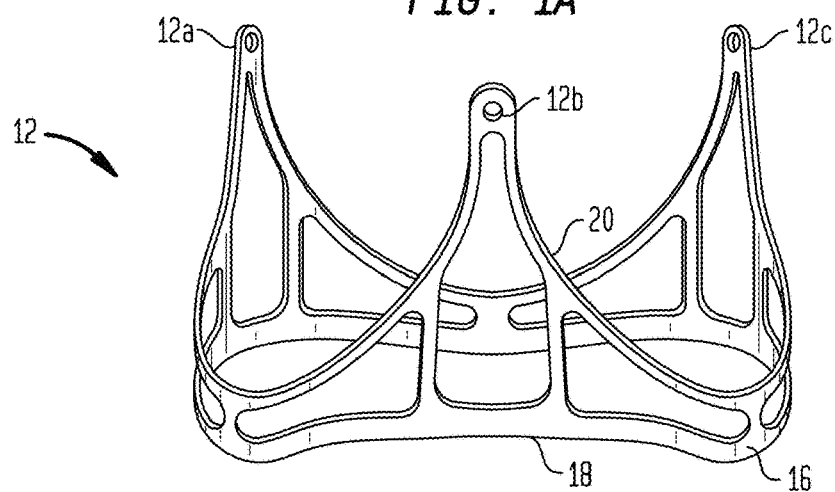
FIG. 1A is a perspective view of a frame of a surgical prosthetic heart valve.
Figure 1B:
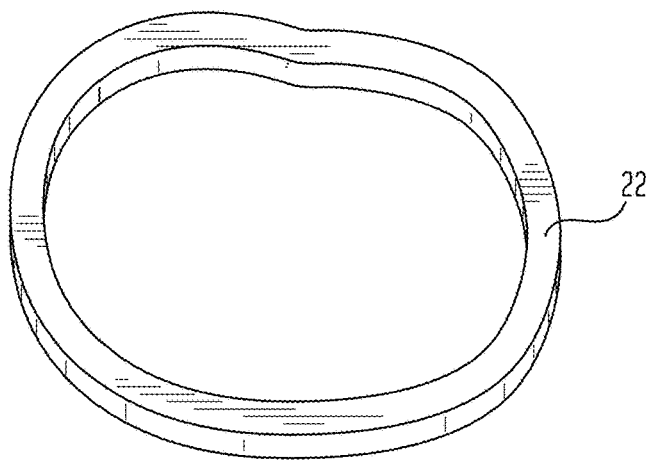
FIG. 1B is a perspective view of a sewing cuff insert of a surgical prosthetic heart valve.
Figure 1C:
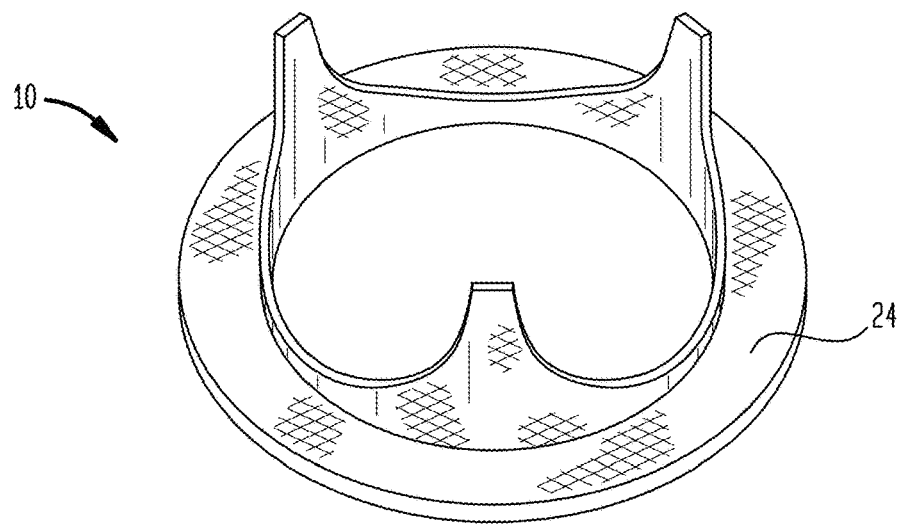
FIG. 1C is a perspective view of the frame and sewing cuff insert of FIGS. 1A-B in an assembled condition and covered by a fabric.

FIGS. 1A-1C illustrate a surgical heart valve 10 and several components thereof. Surgical heart valve 10 may be surgically implanted into a patient to replace a native heart that may be not functioning as intended, such as the aortic valve, mitral valve, pulmonary valve, or the tricuspid valve. Surgical heart valve 10 may have a non-collapsible frame 12, shown in FIG. 1A, having a generally annular shape. Frame 12 may be formed of any suitable biologically compatible material, including titanium, Elgiloy® MP3N, or another metal, which may be laser cut from a tube, or from a biologically compatible polymer, such as PEEK or acetal. Since the valve of the illustrative embodiment is a tricuspid valve (e.g., for use in replacing a patient's aortic valve), frame 12 has three commissure posts 12a, 12b, and 12c that are equally spaced from one another around the circumference of the frame. Each commissure post stands up from the annularly continuous base 16 of frame 12, and they support and/or serve as attachment points for a plurality of prosthetic leaflets (not shown). Although frame 12 is illustrated with three commissure posts 12a-c for supporting a three-leaflet valve assembly, it should be understood that the frame could include more or fewer commissure posts for supporting a corresponding number of prosthetic leaflets. Base 16 of frame 12 may include a blood-inflow edge 18 that is scalloped as one proceeds around the frame to approximately match the natural scallop of the native valve annulus. The frame may also include an annularly continuous blood-outflow edge 20, which merges with and becomes part of each commissure post 12a-c. The inflow edge 18, outflow edge 20, and flexibility of the frame are designed to help ensure proper opening and coaptation of the leaflets of the prosthetic heart valve during use. The prosthetic leaflets may be formed of a biological material, such as bovine pericardium, or from any of the engineered leaflet materials disclosed herein.

Frame 12 may be covered by a fabric covering (not shown), particularly over each commissure post 12a-c. One example of an appropriate covering fabric is reemay fabric, which is a spun form of polyester. A ring 22 (FIG. 1B), which may be formed of silicone, may be positioned around the outside of the inflow edge 18 of frame 12. The entire frame 12 and ring 22 may be completely covered inside and out by a further fabric layer. Subsequently, a layer of tissue 24 may be applied over the fabric layer, including both inside and outside of frame 12 and over ring 22. Tissue layer 24 is typically formed of any mammalian tissue, and in particular any mammalian pericardium tissue, such as porcine, equine, or bovine pericardium. In the completed surgical heart valve 10, the covered ring 22 serves as a sewing cuff for sewing the prosthetic heart valve into the native valve annulus of the patient.

The collapsible/expandable prosthetic heart valves of the disclosure have an expanded condition and may also have a collapsed condition. Although aspects of the disclosure apply to a collapsible/expandable prosthetic heart valve for replacing a native aortic valve, the disclosure is not so limited, and may apply to prosthetic valves for replacing other types of cardiac valves, including, the mitral valve, the tricuspid valve and the pulmonary valve. Nor is the disclosure limited to a specific method of delivery. For example, the collapsible/expandable prosthetic heart valves described herein may be delivered via any suitable transcatheter delivery route, including a transfemoral route, a transvenous route, a transapical route, a transjugular route, a transaortic route, a transsubclavian route, etc. Further, the collapsible/expandable prosthetic heart valves described herein may be delivered via traditional surgical routes, or any suitable minimally invasive route.

Figure 2:
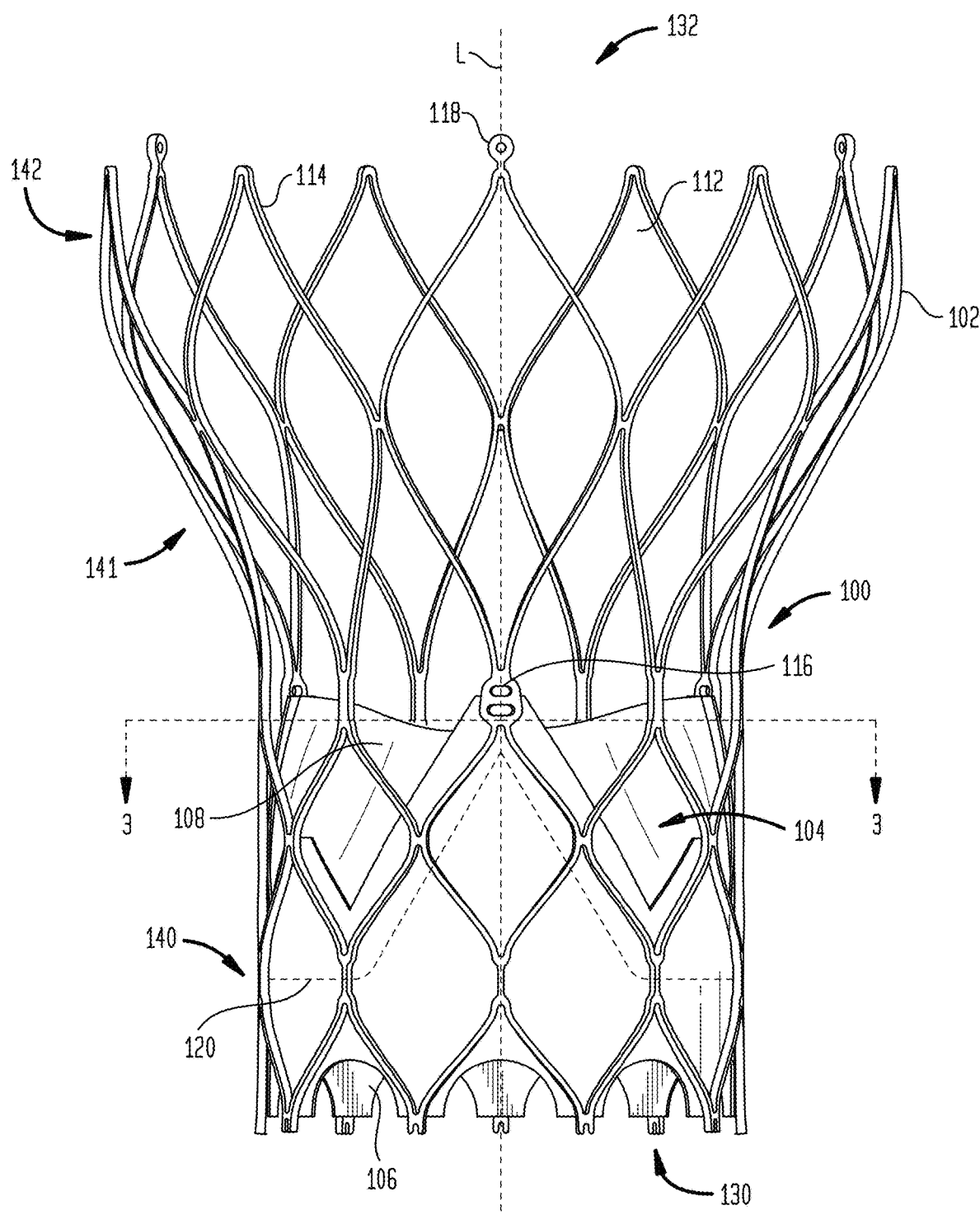
FIG. 2 is a side view of a stent-supported prosthetic heart valve according to the prior art in an expanded condition.

FIG. 2 shows one embodiment of a collapsible/expandable stent-supported prosthetic heart valve 100 according to the prior art, the prosthetic heart valve being shown in an expanded condition. Prosthetic heart valve 100 is designed to replace the function of the native aortic valve of a patient, and includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 2, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a delivery device (not shown). The engagement of retaining elements 118 with the retaining structures on the deployment device may help maintain prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is described in U.S. Patent Publication No. 2012/0078352, the disclosure of which is hereby incorporated by reference herein.

Stent 102 may also include a plurality of commissure attachment features 116 for mounting the leaflet commissures of the valve assembly to the stent. As can be seen in FIG. 2, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. It should be understood that stent 102 may include other forms of commissure attachment features, or may omit commissure attachment features, with the prosthetic leaflets being attached to the stent via other mechanisms, such as direct suturing or via intermediary attachment panels. Examples of other attachment modalities may be found in U.S. patent application Ser. No. 16/568,345, filed Sep. 12, 2019, the disclosure of which is hereby incorporated by reference herein.

Prosthetic heart valve 100 includes a valve assembly 104 which, in one embodiment, may be positioned entirely in the annulus section 140 of stent 102. Valve assembly 104 includes a plurality of leaflets 108 that collectively function as a one-way valve by coapting with one another, and a cuff 106 positioned on the luminal surface of stent 102 surrounding leaflets 108. Although cuff 106 is shown in FIG. 2 as being disposed on the luminal or inner surface of annulus section 140, the cuff may be disposed on the abluminal or outer surface of the annulus section, or may cover all or part of either or both of the luminal and abluminal surfaces of the annulus section. As prosthetic heart valve 100 is intended to replace the aortic valve (which ordinarily is a tri-leaflet valve), it is shown in FIG. 2 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a attachment edge 120, indicated with broken lines in FIG. 2. Leaflets 108 may be joined to stent 102 and/or to cuff 106 by techniques known in the art other than suturing. Above attachment edge 120, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130 which allows the left and right coronary arteries to fill and feed blood to the heart muscle. It will be appreciated that prosthetic heart valves according to aspects of the present disclosure may have more or less than the three leaflets 108 and commissure attachment features 116 shown in FIG. 2 and described above.

Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features and the outflow end 132 of the stent.

In operation, prosthetic heart valve 100 may be used to replace a native heart valve, such as the aortic valve, a surgical heart valve, or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, transvenous, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction. (See U.S. Patent No. 7,585,321 FIGS. 13a-16b and accompanying disclosure; U.S. Pat. No. 6,458,153 FIGS. 20A-20I and accompanying disclosure.)

Figure 3:
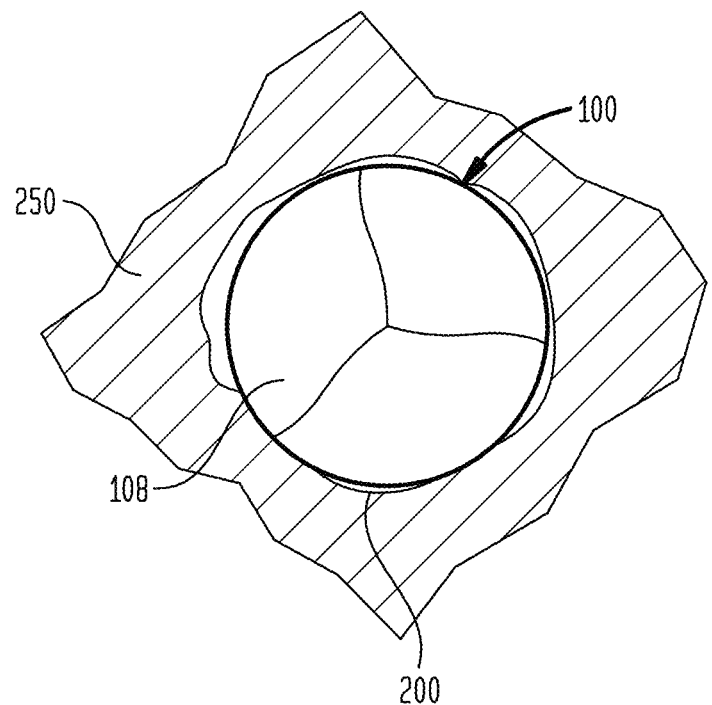
FIG. 3 is a highly schematic transverse cross-section of the prosthetic heart valve taken along line 3-3 of FIG. 2 and implanted in a native valve annulus.

FIG. 3 is a highly schematic transverse cross-section of prosthetic heart valve 100 taken along line 3-3 of FIG. 2 and showing leaflets 108 disposed within native valve annulus 250. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in PV leak or regurgitation and other inefficiencies which can reduce cardiac performance. Such improper fitment may be due to suboptimal native valve annulus geometry, for example, as a result of the calcification of the tissue of native valve annulus 250 or the presence of unresected native leaflets.

Figure 4:
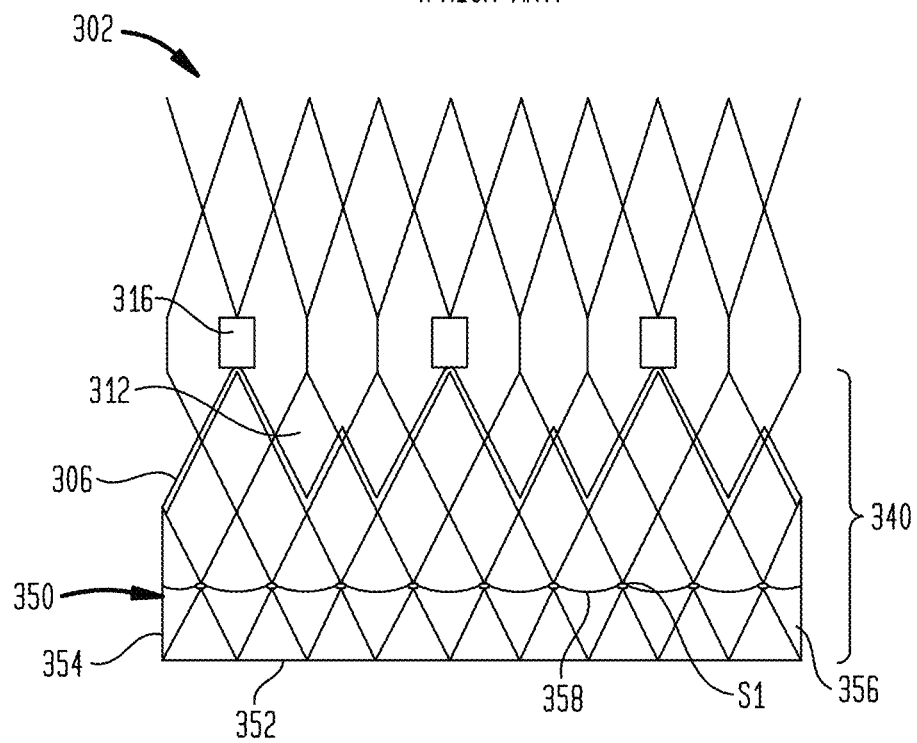
FIG. 4 is a highly schematic developed view of an expanded stent which is illustrated flattened as if it were cut longitudinally, illustrating inner and outer cuffs attached to the stent.

FIG. 4 depicts a collapsible/expandable prosthetic heart valve very similar to that shown in FIGS. 2 and 3, except that it is shown as if cut longitudinally and flattened. The heart valve can include a stent 302 with commis sure attachment features 316. A cuff 306 similar or identical to cuff 106 may be positioned on the luminal and/or abluminal surface of stent 302. Indeed, cuff 306 in FIG. 4 is illustrated as being positioned on the luminal or inner surface of stent 302. However, in order to help minimize or eliminate PV leak, for example through the gaps 200 shown in FIG. 3, additional material may be coupled to the exterior of stent 302 as an outer cuff 350. In the illustrated example, outer cuff 350 may have a substantially rectangular shape and may be wrapped around the circumference of stent 302 at the inflow end of the stent so as to overlap in the longitudinal direction of the stent with cuff 306. This is only one embodiment of such an exterior or outer cuff. Outer cuff 350 may be formed as a single piece of material having a proximal edge 352, two side edges 354, 356, and a distal edge 358. Preferably, the proximal edge 352 of outer cuff 350 is coupled to stent 302 and/or to inner cuff 306 at or near the inflow end of the stent, for example by a continuous line of sutures (not shown), with the side edges 354 and 356 of the outer cuff joined to one another, so that retrograde blood flow (flowing from the outflow end toward the inflow end) entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff may be attached to stent 302 and/or to inner cuff 306 at locations that are spaced apart in the circumferential direction. The distal edge 358 of outer cuff 350 may, for example, be sutured to stent 302 at attachment points S1 located where each cell 312 in the proximal-most row of cells intersects with an adjacent cell in that same row. In the illustrated example, since there are nine cells 312 in the proximal-most row, there are nine separate attachment points Si at which the distal edge 358 of outer cuff 350 is sutured or otherwise attached to stent 302 and/or to inner cuff 306. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Outer cuff 350 may also comprise multiple pieces of material that, when joined together, form a shape and provide a function that are similar to what has been described above. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximal-most row of cells in stent 302 as measured along the major axis of the cell between two of its apices when the cell is in an expanded condition. However, outer cuff 350 may have other suitable heights, such as the full axial height of a cell 312 in the proximal-most row of cells, or more or less than the full axial height of a cell 312 in the proximal-most row of cells. Still further, although inner cuff 306 and outer cuff 350 are described above as separate pieces of material joined to stent 302 and to each other, the cuffs may be formed integrally with one another from a single piece of material that is wrapped around the inflow edge of the stent, with the distal edge 358 of the outer portion of the cuff joined to the stent and/or to the inner portion of the cuff at attachment points Si as described above. With this configuration, the proximal edge 352 of outer cuff 350 does not need to be sutured to stent 302, although it still may be preferable to provide such attachment. The various valve components including, without limitation, inner cuffs, outer cuffs and leaflets, and valve assemblies made therefrom, may be attached to each other and/or to the stent in any conventional manner, including suturing, gluing, molding, welding, heating, cross-linking, and the like. (See U.S. Pat. Nos. 6,821, 297; 6,458,153; 7,585,321; 5,957,949.)

Valve assemblies, such as valve assembly 104 comprising inner cuff 106/306, leaflets 108, as well as outer cuff 350, may be formed of the same or different materials, including any suitable biological material, including "fixed" bovine or porcine tissue, or a polymer such as, for example, polyolefins such as polytetrafluoroethylene (PTFE), polyethylenes including ultra-high molecular weight polyethylene (UHMWPE), and polypropylene, as well as polyurethane, PEEK, polyvinyl alcohol, silicone, or combinations thereof. (See U.S. Pub. No. 2018/0055631 A1, the disclosure of which regarding the structure, function and manufacture of a heart valve are hereby incorporated by reference herein.) In accordance with the present disclosure, at least one of the components of a valve, including, without limitation, leaflets or cuffs, valve assemblies, and the like, is produced from an uncoated or coated fabric as described herein.

The description of surgical heart valve 10 and collapsible/expandable prosthetic heart valve 100 are for context only. Thus, the coated and uncoated fabric materials described herein may be used in surgical heart valves that are similar to surgical heart valve 10 or surgical heart valves that are very different therefrom. Similarly, the presently disclosed coated and uncoated fabric materials may be used in collapsible/expandable prosthetic heart valves that are similar to prosthetic heart valve 100, or prosthetic heart valves that are very different therefrom, such as heart valves having a balloon-expandable stent; heart valves that do not have an aortic section; heart valves in which the stent has an hourglass profile, right cylindrical sections or ovoid cross-sections; heart valves intended to replace other cardiac valves, such as the mitral valve; etc. For example, the stent may be made of a single or multiple bent wires such as illustrated in U.S. Pat. No. 5,411,552 or U.S. Pat. No. 5,855,601, forming a zigzag or sinusoidal shape, or may be made from interwoven or intercrossing bars such as shown in U.S. Pat. Nos. 5,545,214 and 7,585,321. The stent may also be formed of woven materials which can be such as shown in EP 2,926,766, which is hereby incorporated by reference herein for its teaching of a woven stent and for its teachings regarding the mounting of a cuff and/or sac on the interior or exterior of a stent. Often, however, the stent is made from a laser-cut nitinol tube. A balloon-expandable stent may be composed of biocompatible metals known in the art, including but not limited to, cobalt chromium and stainless steel. The stent may be continuous or discontinuous (made in sections that are attached to one another directly or indirectly—see, for example, U.S. Pat. No. 5,957,949). Therefore, the descriptions herein of surgical heart valve 10 and collapsible/expandable prosthetic heart valve 100 should in no way be considered as limiting the features and applications of the coated and uncoated fabric materials disclosed herein.

According to the present disclosure, one or more of the valve components and, in particular, the inner and/or outer cuff(s) and/or one or more leaflets, may be made from a woven or knitted fabric, or from a felt or other polymeric fabric that is nonwoven. As used herein, the term "fabric" refers to a polymer-fiber containing material having filaments, threads, yarns, or other strands (collectively, "fibers") that are interlaced with one another to form a web. The fibers may be formed of any one or more of a variety of materials, including natural materials, polymers, or blends of natural materials and polymers, so long as it includes a majority of polymer fibers. The natural materials may include cotton, wool, hemp, jute, silk, linen, alpaca, cashmere and the like. The polymer fibers may include, for example, polyolefins such as polytetrafluoroethylene (PTFE) (including expanded, stretched, low molecular weight, medium molecular weight, high molecular weight and ultra-high molecular weight (UHMW)), polyethylenes (including low, medium, high and ultra-high molecular weight polyethylene (UHMWPE—e.g., having an average molecular weight of between about 2 and about 7.5 million atomic mass units)), and polypropylene (including low, medium, high and ultra-high molecular weight polypropylene (UHMWPP)), as well as polyurethane, PEEK, polyvinyl alcohol, silicone, rayon, polyesters, aramid, spandex, or combinations thereof. The fibers may have any cross-sectional shape, including round, rectangular, triangular, polygonal, oval, etc. Moreover, the fibers may be selected to have desired dimensions, such as diameter, width, thickness and/or length. The fibers may also be porous or nonporous, and drug-eluting or non drug-eluting. In addition, the fibers may each consist of a single strand or filament, or of multiple strands or filaments. For fibers comprised of multiple strands or filaments, the strands or filaments may be braided, twisted or otherwise joined together in a bundle. (When used herein, the term "fibers" shall include both individual fibers as well as fiber bundles.) The fibers may be selected based on certain properties, such as creep, tensile strength, elastic modulus, strain/elongation, compressibility, flexural rigidity and stiffness, and twist direction and magnitude. Other properties that may influence the selection of certain fibers include melt flow viscosity, percent spin finish, linear density, tenacity, melting temperature, biocompatibility, purity, Denier, color, radiopacity, surface friction and entanglement.

In addition to their mechanical properties, the individual fibers may be uncoated, or they may be coated with another material. In one form of coated fiber, the fiber may be conjugated (i.e., chemically reacted) with another material, for example, a therapeutic drug or a lubricious material. In another form of coated fiber, the fiber may be coated with a polymer or other material. In still another form of coated fiber, a porous fiber may be infused with a polymer, a therapeutic drug, a lubricity-promoting agent or another material. Any known technique may be used to coat the fiber with a polymer or other material, including spray coating, dip coating and the like. Once coated, the fibers may be allowed to dry or, for polymer coatings, the polymer may be solidified by cross-linking. It will be appreciated that, for coated fibers, the coating may be applied uniformly around the surface of the fiber, or it may be applied to only portions of the fiber surface and/or along only portions of the fiber length.

Despite the various materials and structures that have been used to produce the various components of prosthetic heart valves and other medical devices, the prior art has not taught the use of the uncoated and coated polymer fabrics described hereafter for use in such devices. Fabrics that are formed by interlacing fibers, whether the interlacing is ordered as in a woven or knitted fabric, or random as in a felt, and whether the fibers themselves are individually coated or uncoated, but not coated by another material after the interlacing step or steps, are referred to herein as "uncoated fabrics." Uncoated fabrics include fabrics formed of woven or knitted fibers and fiber bundles, as well as felts, mats and other nonwoven materials formed from interlaced fibers. The fabrics of the present disclosure, whether uncoated fabrics or coated fabrics as described below, may be formed from fibers having any of the compositions or any of the properties described above. However, "fabrics" must include at least a majority of polymer fibers. The properties of the resulting fabric will depend, of course, on the properties of the fibers from which the fabric is formed, as well as on the manner in which the fabric is formed. In some embodiments, the fabric may be created by knitting or weaving together fibers of one or more materials through various weaving or knitting techniques. In other embodiments, the fabrics may be formed by randomly interlacing the fibers to form a felt or matted web. By controlling the forming process, certain desired properties in the resultant fabric may be obtained. For example, for woven fabrics, controlling the fabric "thread count," or number of fibers (or fiber bundles) per square inch, or for knitted fabrics, controlling the fabric "stitch density," or number of needle loops per square inch, can affect at least the overall strength of the fabric, as well as the fabric's flexibility and porosity.

The weave of the fabric may also determine the extent of porosity in the fabric. The fabric's porosity corresponds to the number and size of the open areas formed between the fibers as a result of the weaving or knitting process. When used as a component of a prosthetic heart valve, the fabric, when the prosthetic heart valve has been implanted, may be in contact with tissue and may promote a healing response. The porosity of the woven or knitted fabric may allow cells to flow through the valve component, but after blood makes contact with the fabric, the fabric may become less permeable or impermeable.

Expanding on the foregoing, an uncoated fabric may promote cell adhesion, wherein cells may attach to a single fiber of the fabric or to a plurality of fibers of the fabric. The cells may adhere or attach to the fabric without inhibiting the expected performance of the material. For example, for fabrics having a high porosity weave, the cells may attach to a single fiber of the fabric. Cell adhesion may be aided by the deposition of blood proteins, plasma, coagulation products, fibrin or other materials. In some embodiments, cells may migrate into the prosthetic heart valve from the adjacent tissue and may attach or adhere to the fabric components. In other embodiments, cells from the blood may be entrapped in the fabric and may attach or adhere to individual fibers of the fabric.

Figure 5:
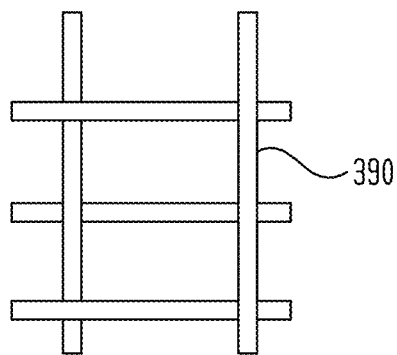
FIG. 5 is an enlarged schematic view of the fibers of a porous uncoated fabric.
Figure 6:
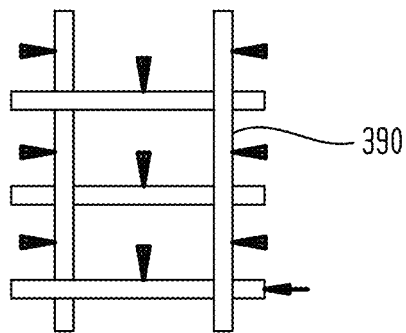
FIG. 6 is an enlarged schematic view of the fibers of a porous uncoated fabric, in which the fibers are conjugated with another material.
Figure 7:
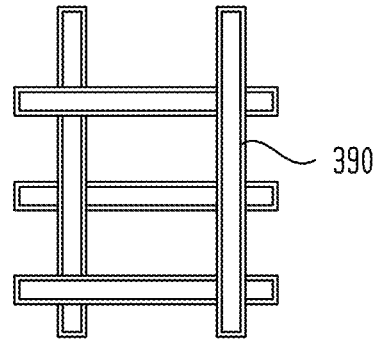
FIG. 7 is an enlarged schematic view of the fibers of a porous uncoated fabric, in which the fibers are coated with another material.

The adhesion of cells to the fabric may also be influenced by the composition of the fibers and whether the fibers themselves are coated or uncoated, and if coated, the composition of the coating. In some embodiments, porous fibers may be impregnated with a drug or other material that may either promote or retard cell adhesion. In other embodiments, the individual fibers may be either partially or fully conjugated or coated with a polymer, a therapeutic drug and/or another material prior to forming the fibers into a fabric. FIGS. 5-7 show different embodiments of an uncoated fabric. In one embodiment, shown in FIG. 5, the individual fibers 390 of the fabric are uncoated. In another embodiment, shown in FIG. 6, the individual fibers 390 of the fabric may be conjugated with another material, for example, a therapeutic drug, before the fibers are woven or knitted to form the uncoated fabric. In a further embodiment, shown in FIG. 7, the individual fibers 390 of the fabric may be coated with a polymer or other material before the fibers are woven or knitted to form the uncoated fabric. Where the fabric is formed from fibers that have been conjugated or coated with another material, every fiber of the fabric may be so conjugated or coated, either partially or fully, or only some of the fibers of the fabric may be so conjugated or coated.

The fabrics may also be engineered to have certain mechanical properties, such as a desired creep, compression, burst strength, suture retention, flexural rigidity/stiffness, tearing strength, delamination strength, and stretch/elongation. Other fabric properties that may be sought include a specific anisotropy, color, weight, extractable content, permeability, radiation sensitivity, radiopacity, moisture sensitivity, temperature sensitivity, and/or chemical sensitivity. As noted, many of these parameters may be influenced by the particular fibers used to form the fabric, while others may be more influenced by the manner in which the fabric is formed from the fibers. In addition, the fabric may include one or more radiopaque fibers to assist in identifying the location and orientation of one or more features of the prosthetic heart valve or other medical device in which the fabric is incorporated.

The fabrics may be engineered to have a desired thread count, a desired tensile strength, a desired areal density, and/or a desired thickness, all measured before the medical device incorporating the fabric is implanted in a patient. When the fabric is a woven fabric, it preferably has a thread count of at least about 150, 200, 250, 300, 350, 400, 450, 500, 600, 700, 800, 900, 1000 or more total fibers per square inch per layer of fabric. The thread count need not be symmetrical. For example, one could use a fabric of about 100×50, 100×125, 220×110, 330×170, 360×180, 400×200 and 440×220 fibers in a square inch. In one embodiment, the thread count is from about 200 to about 500 by about 200 to about 500 fibers in a square inch (200-500×200-500), and in another embodiment is from about 300 to about 500 by about 100 to about 300 fibers in a square inch (300-500× 100-300). In some embodiments, the fabric is a high density weave having more than 300 fibers per square inch. Further, the thread count in one portion of the fabric may be different from the thread count in another portion of the fabric. For example, when the fabric is used to form a leaflet of a prosthetic heart valve, the thread count at the attachment edge may be greater than the thread count in the belly portion or at the free edge of the leaflet. The greater thread count at the attachment edge produces a fabric with greater strength in the region at which the leaflet is attached to the cuff and/or stent and experiences a large amount of stress in use. The density of the weave may be adjusted, and often reduced, to promote flexibility and adhesion of layers, including adhesion through the fabric of a coating on one major surface of the fabric to a coating on the other major surface of the fabric. When the fabric is a knitted fabric, it typically has a lower thread count or stitch density than a woven fabric. Knitted fabrics may have a stitch density of from about 2 to about 750 per square inch or from about 5 to about 500 per square inch.

In some embodiments, the fabric has a tensile strength of at least about 50N, and in other embodiments about 60N. In still other embodiments, the tensile strength is about 70N or more. A tensile strength of at least about 75N may be used, as may a tensile strength of at least about 85N or at least about 100N.

In some embodiments, woven or knitted fabric has an areal density of at least about 0.5±0.1 ounces/yard$^2$, in other embodiments, an areal density of at least about 0.65±0.1 ounces/yard$^2$, and in still other embodiments, an areal density of about 0.8±0.05 ounces/yard$^2$. It will be appreciated that weave density and thread counts balance the need for strength, flexibility and porosity. For an uncoated fabric, pore density between woven/knitted fabric fibers should not be large enough to cause appreciable leakage through the fabric. On the other hand, in general, the fewer the number of fibers and/or the larger the number of pores in the fabric, the greater will be the flexibility of the fabric and the more a synthetic fabric leaflet will resemble a healthy native leaflet. Stated another way, the woven or knitted fabric in one embodiment has an areal density of at most about 1.3±0.1 ounces/yard$^2$, and in another embodiment, an areal density of no more than about 1.0±0.1 ounces/yard$^2$.

In some embodiments, the uncoated fabric has a thickness of about 10 µm to about 200 µm, and in other embodiments, a thickness of about 20 µm to about 100 µm. In some embodiments, the thickness of the fabric is from about 50 µm to about 100 µm. Thickness is a balance between durability, resilience, and flexibility. At a thickness of about 75 µm, the fabric leaflets of the disclosure are often only about 20% of the thickness of most tissue leaflets used in conventional collapsible heart valves, which are about 300-450 µm thick, or about 10% of the thickness of most tissue leaflets used in surgical heart valves, which are about 400-800 µm thick.

Any of the properties of the fabric may be selected depending on the particular application for the fabric. For example, while some parameters may be suitable for fabrics forming the cuffs and/or leaflets of a collapsible/expandable prosthetic heart valve, fabrics having other parameters may be better suited for other medical devices described below.

Figure 8:
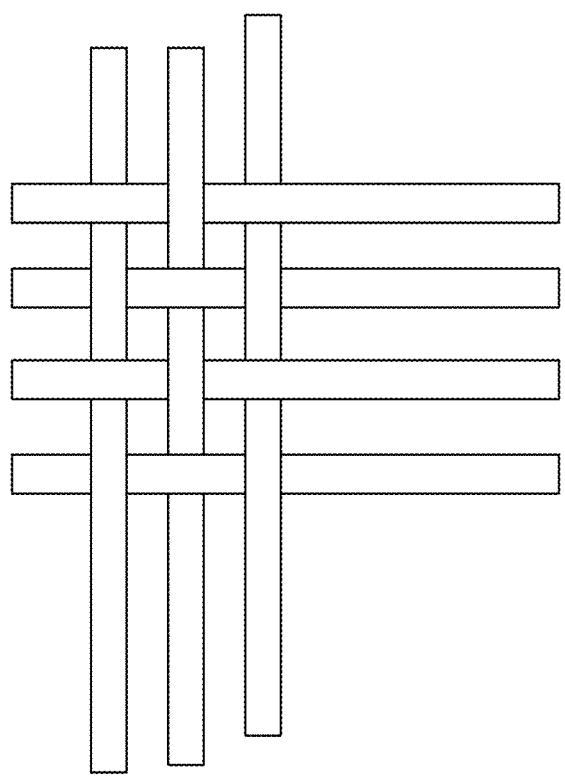
FIG. 8 is an enlarged view of a plain weave pattern.
Figure 9:
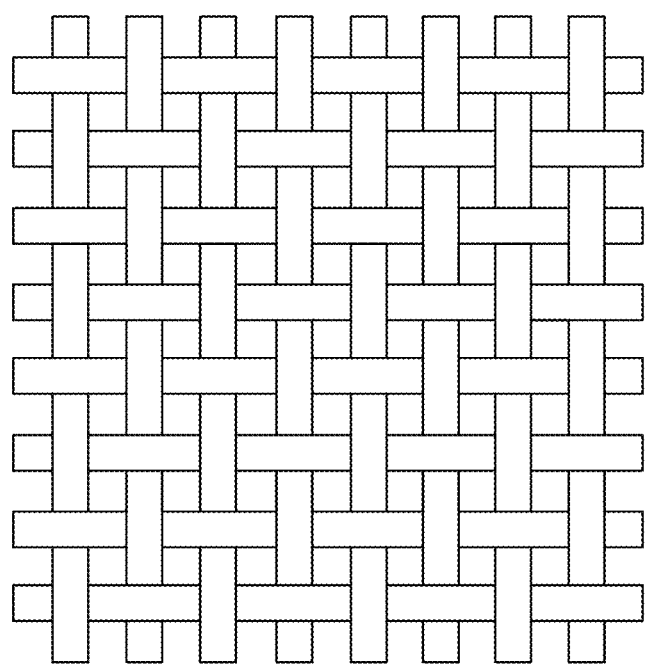
FIG. 9 is a plan view of a plain weave pattern.
Figure 10:
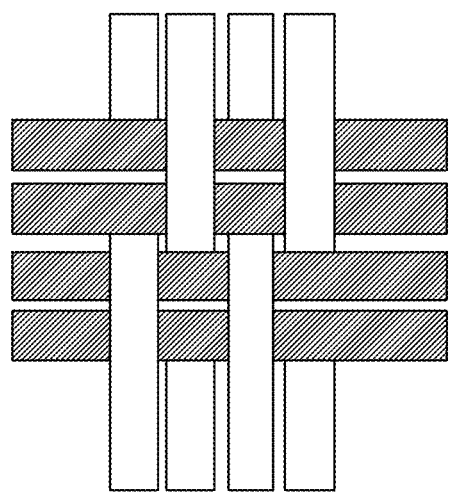
FIG. 10 is a plan view of a warp rib weave pattern.
Figure 11:
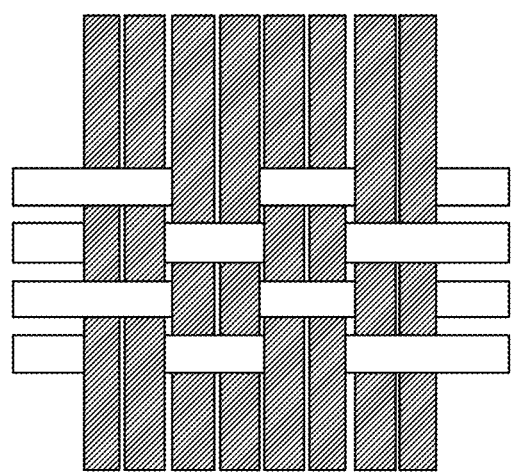
FIG. 11 is a plan view of a weft rib weave pattern.
Figure 12:
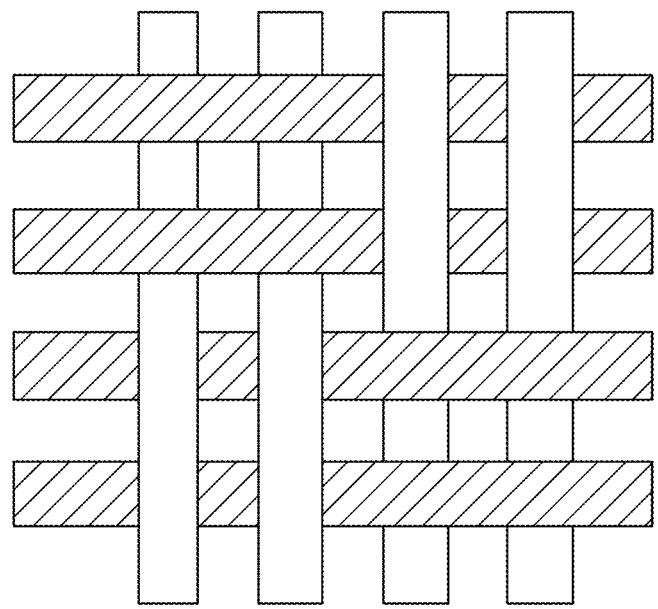
FIG. 12 is a plan view of a basket weave pattern.
Figure 13:
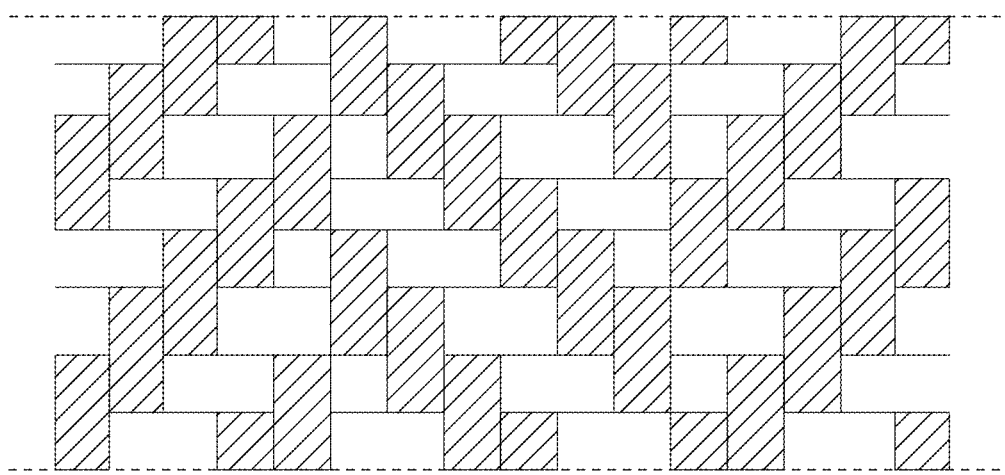
FIG. 13 is a plan view of a herringbone weave pattern.
Figure 14:
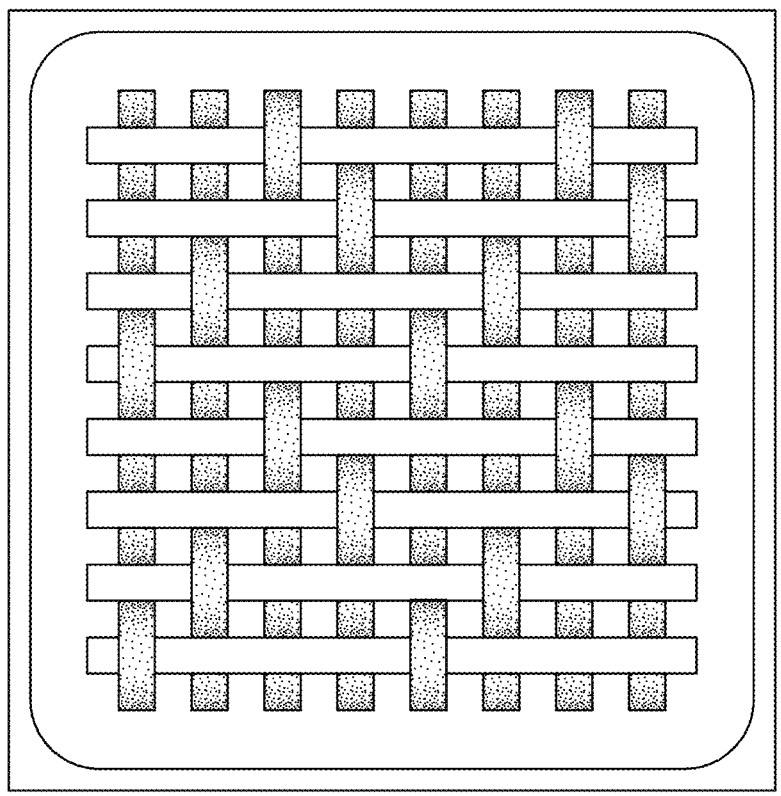
FIG. 14 is a plan view of a satin weave pattern.
Figure 15:
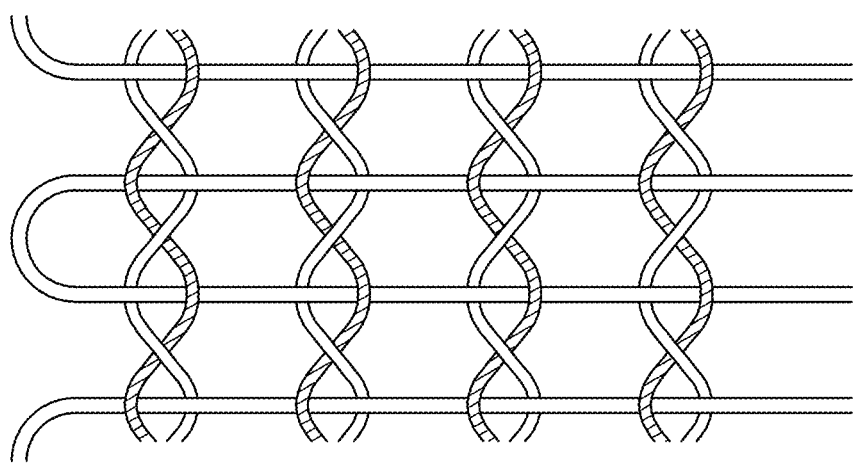
FIG. 15 is a plan view of a leno weave pattern.
Figure 16:
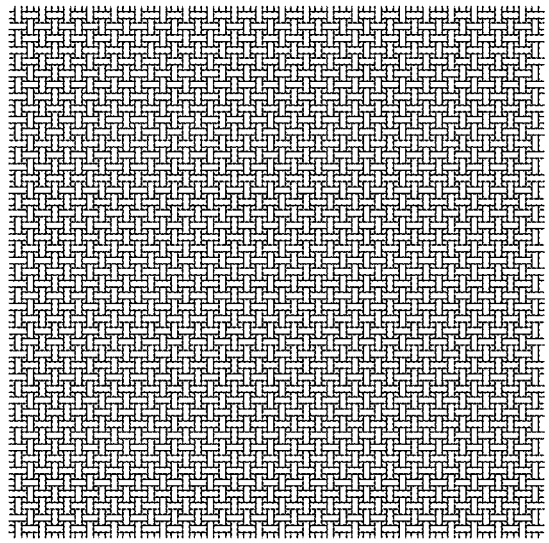
FIG. 16 is a plan view of a twill weave pattern.

FIGS. 8 to 19 illustrate various techniques that may be used to form the fabric. As noted previously, the fabric may be formed by interlacing two or more fibers, or in the case of knit fabrics at least one fiber, which can be accomplished in several ways. Some of the methods for interlacing two or more fibers include weaving, knitting, braiding, plaiting, electro spinning, 3-D printing or entangling the fibers through felting, bonding or lamination. Woven fabrics may be fabricated through various techniques. As used herein in connection with the various weaving techniques, "filling" or "weft" refers to fibers that extend along the width of the fabric, while "warp" refers to fibers that extend along the length of the fabric. A plain weave, shown in FIGS. 8 and 9, is the simplest weaving method in which a single filling fiber is passed over and under each warp fiber, with the pattern in adjacent rows alternating. (*Plain weave*, Encyclopaedia Brittanica, Dec. 17, 2010, https://www.britannica.com/technology/plain-weave accessed on Oct. 11, 2019.) One derivative of the plain weave is the rib weave, in which two or more adjacent rows of the filling fiber are passed in the same pattern over and under each warp fiber. (Watson, Kate Heintz et al., *Textiles and Clothing,* 1907, Home Economics Association, p. 77.) Two versions of the rib weave may also be used, the warp rib weave and the weft rib weave shown in FIGS. 10 and 11. The warp rib weave produces a rib or cord in the weft direction, while the weft rib weave produces a rib or cord effect in the warp direction. (*Difference between Warp Rib Weave and Weft Rib Weave*, Define Textile, 2019, http://www.definetextile.com/2013/05/difference-between-warp-rib-weave-and.html, accessed on Oct. 23, 2019). A weft weave of polyethylene terephthalate (PET) may be particularly desirable for certain applications, such as for cuffs and/or leaflets of prosthetic valves. Another derivative of the plain weave is a basket weave, in which both the filling fiber and the warp fiber run in double or triple strands. (Watson, Kate Heintz et al., *Textiles and Clothing,* 1907, Home Economics Association, p. 77.) That is, in a basket weave, shown in FIG. 12, two or more adjacent rows of the filling fiber are passed in the same pattern over and under two or more adjacent rows of the warp fiber. Another weaving technique that may be used to fabricate a woven fabric is the twill weave, shown in FIG. 16. The twill weave is known for producing a diagonal pattern when the filling fibers are woven over and under two or more adjacent warp fibers. (*Twill weave,* 2019, https://www.dictionary.com/browse/twill-weave, accessed on Oct. 11, 2019.) A version of the twill weave includes the herringbone weave, shown in FIG. 13, which resembles a broken zigzag or the bones of a fish. (*What is a Herringbone Weave*?, Shirts of Holland B. V., 2019, https://sleeve7.com/blog/what-is-a-herringbone-weave/, accessed on Oct. 11, 2019.) Another basic weaving technique is the satin weave which produces a soft, smooth and lustrous face without the appearance of a pattern. (*Basic Weaves*, Cotton Incorporated, 2019, https://www.cottonworks.com/topics/sourcing-manufacturing/weaving/the-art-of-weaving-basic-weaves/, accessed on Oct. 11, 2019). An example of the satin weave is shown in FIG. 14.

Figure 17:
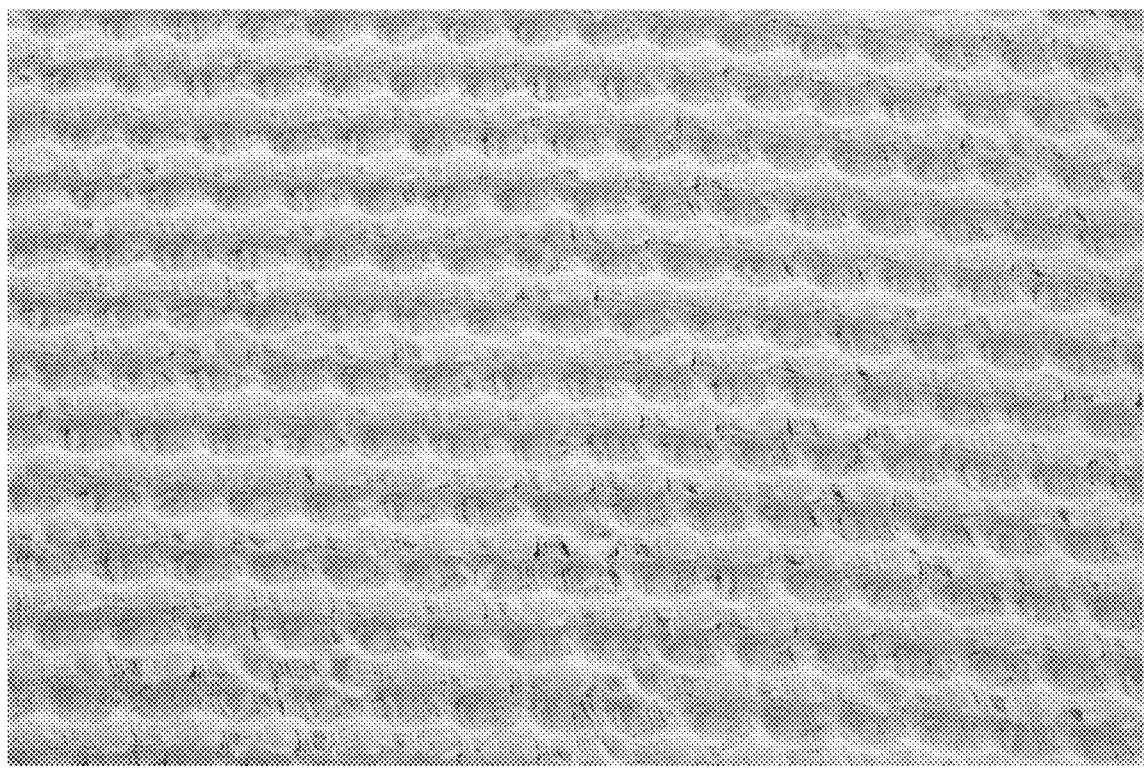
FIG. 17 is a plan view of a waffle weave pattern.
Figure 18:
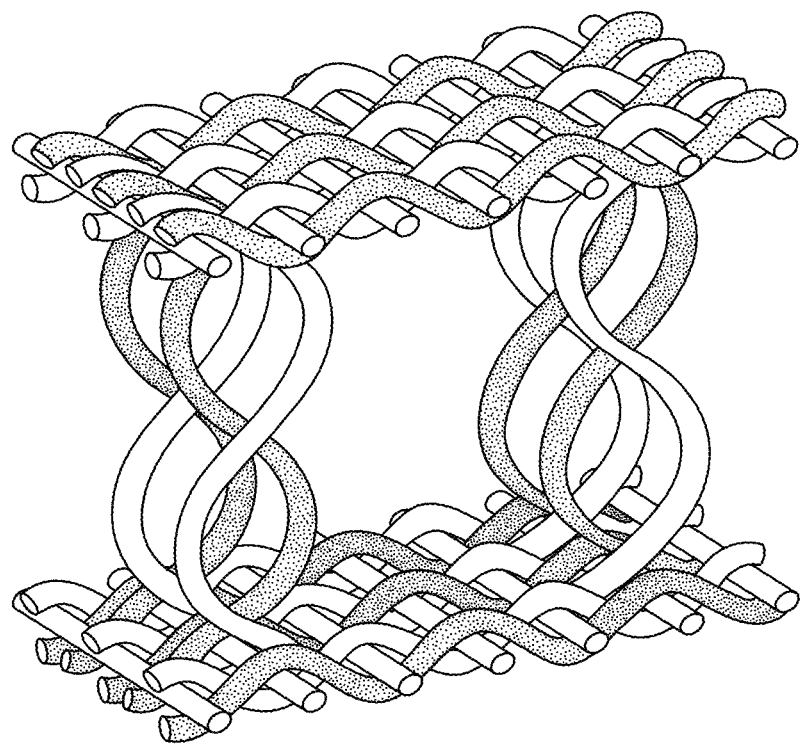
FIG. 18 is a perspective view of a pile weave pattern.

Additional weaving techniques can be used to form the fabric as well. One additional weaving technique is the leno weave, shown in FIG. 15, a principal of interweaving in which some of the warp ends do not lie parallel to one another, but are twisted partly around other ends. (*Leno Weaves*, Serial 512. Ed. 1., International Textbook Co., https://www2.cs.arizona.edu/patterns/weaving/monographs/ics512.pdf, accessed on Oct. 11, 2019.) Another weaving technique is the Bedford cord, in which the weave produces longitudinal warp lines in the fabric with fine sunken lines in between. (*Bedford Cords*, TextileSchool4U.Blogspot.com, 2013, http://textileschool4u.blogspot.com/2013/12/bedford-cords.html, accessed on Oct. 11, 2019.) A waffle weave as shown in FIG. 17 can also be used by weaving the fabric into a pattern resembling a honeycomb. (*Honeycomb*, The Free Dictionary, https://www.thefreedictionary.com/waffle+weave, accessed on Oct, 11, 2019.) Also usable is a pile weave, which incorporates a loop pattern into the weave to produce a fabric with a raised, dense surface. (Adam Augustyn, Weaving, 2008, https://www.britannica.com/technology/weaving#ref290551, accessed on Oct. 11, 2019.) An example of a pile weave is shown in FIG. 18. A jacquard weave is another available technique which produces a fabric on a special loom because of the complex woven-in designs. (Id.) Similarly, a dobby weave requires a special loom attachment to incorporate small, geometric, textured, repeated woven-in designs. (Id.) Tapestry weaving, in which the warp fibers do not show at all, is another available technique. (*Tapestry Weaving Basics,* 2019, https://www.mirrixlooms.com/pages/tapestry-weaving-basics, accessed on Oct, 11, 2019.) An additional weaving technique is the double cloth weave, in which the fabric is made of two or more sets of warp fibers and one or more sets of weft or filling fibers that are interconnected to form a two-layered fabric. (Double Cloth, Mar. 20, 2019, https://en.wikipedia.org/wiki/Double_cloth#cite_ref-text_2-0, accessed on Oct. 11, 2019.)

Figure 19:
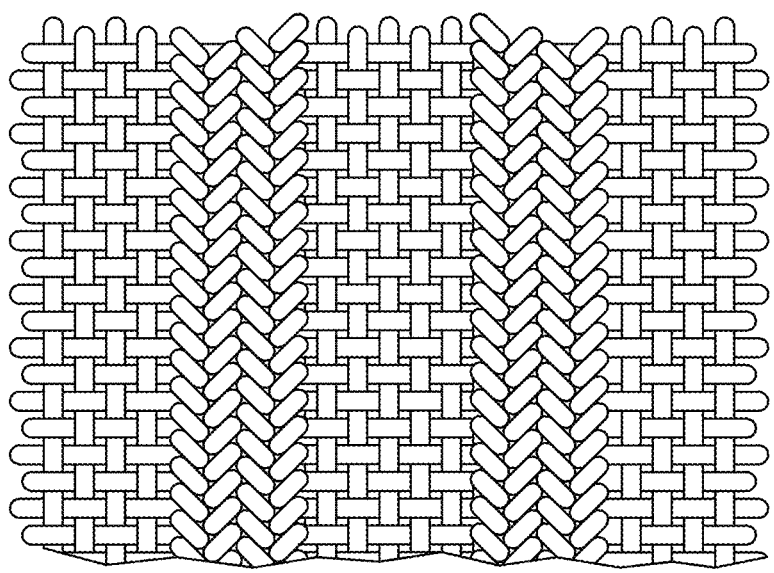
FIG. 19 is a plan view of single knit and purl knit patterns.

A variety of knitting techniques may also be used to produce the fabric. Knitting involves interlacing loops of at least one fiber. The main fabrics produced by knitting are weft knits, specialized weft knits and warp knits. A weft knit fabric can either be a single knit or a double knit. A single knit fabric is produced by one set of needles, while a double knit fabric is produced by two sets of needles. (Random House Kernerman Webster's College Dictionary, 2010, K Dictionaries Ltd.) The most common example of a single knit fabric is a single jersey. The most common double knit fabrics include rib knit, purl knit, interlock knit, cable fabric, bird's eye, cardigans, Milano ribs and pointelle. Examples of single knit and purl knit fabrics are shown in FIG. 19. The rib knit fabric is known for having a ribbed pattern. (*Rib-knit*, Merriam-Webster, 2019, https://www.merriam-webster.com/dictionary/rib-knit, accessed on Oct, 11, 2019.) A fabric with an interlock knit is a variation of the rib knit fabric with closely interlocking stitches providing the tightest weave. Fabrics produced with a specialized weft knit include intarsia, jacquard jerseys, knitted terry, knitted velour, sliver knit, fleece and French terry. There are two types of warp knitting commonly used, raschel and tricot. (*Warp knitting*, Sep. 15, 2019, https://en.wikipedia.org/wiki/Warp_knitting, accessed on Oct. 11, 2019.) Raschel knitting produces fabrics by using latch needles, while tricot knitting uses a bearded needle. (Id.)

No matter their form, polymer fabrics may be coated, either partially or completely, with one or more polymer layers, resulting in a coated fabric. "Coated fabric" in accordance with the disclosure means any of the uncoated fabrics described above, to which a polymer coating, film or layer is deposited or applied, either partially or completely covering at least a portion of one surface or edge of the fabric. The materials used for the fabric, as described previously, can be used for any coating or partial coating. Individual coatings may be the same as or different from one another and from the fabric, and include, without limitation, a PTFE, such as ultra-high molecular weight PTFE (UHMWPTFE) and expanded or stretched PTFE, a polyethylene, such as UHMWPE, and a polypropylene, such as UHMWPP, copolymers or block copolymers of polyethylenes and polypropylenes, and combinations or blends thereof. Other polymers which may be used alone or in combination with those mentioned above include, without limitation, polyurethanes, acrylics, polyesters, polyamides, polyimides, vinyl acetates, alkyds, epoxies, silanes, siloxanes, and the like. Homo- and co-polymers of these materials may also be used. A woven fabric could include fibers of one of or more of these materials or fiber bundles of one or more of these materials. Individual layers of a coating could be made of a single one of these materials or of blends/copolymers of them. When more than one coating layer is used, each of the layers may have the same or a different composition.

In some embodiments, the polymer coating may be produced using films that are directionally oriented in the same or in different directions. In one example, a polymer film may be applied to a top side of the fabric in one direction and a second polymer film may be applied to the bottom side of the fabric in a different direction. In another example, if more than one polymer film is applied to the top or bottom side of the fabric, the polymer film on each side of the fabric may be applied in the same direction or in different directions such that one polymer film is oriented differently from the polymer film that it sits on top of. The fabric/coating could further include or be coated with a drug or active pharmaceutical ingredient (API) or the coating could include the API, which gradually elutes from it. API's may include, for example, Sirolimus, Paclitaxel, Everolimus, or any treatment to enhance resistance to calcification. APIs may also include growth factors, such as vascular endothelial growth factor (VEGF) and transforming growth factor (TGF-beta). It may also be coated with, or the coating may include hyaluronan, hyaluronic acid, glycosaminoglycans (GAGs), Heparin, or amino acids for cell attachment sites, and anti-oxidants such as super oxide dismutase or ascorbic acid. In another embodiment, the fabric can be coated with one or more layers (completely or partially) which are composed of one or more bio-absorbable/biodegradable polymers such as, without limitation: poly-glycolic acid; poly-L-lactic acid; copolymers of poly-glycolic acid and poly-L-lactic acid; polycaprolactone; poly-DL lactic acid; polytrimethylene carbonate; polydioxanone; poliglecaprone; and polyglactin, as well as blends, mixtures and copolymers of the foregoing. It may be important that, for example, tissue ingrowth onto a surface be delayed. Applying a coating to an otherwise porous fabric—sufficiently porous to promote cell attachment—might prevent this, depending on many factors including the type of coating. Using a bio-absorbable/biodegradable polymer for the coating could retard cell attachment until the coating erodes or is absorbed. In another embodiment, and as described elsewhere herein, the coating may include an API that is released gradually. Taxol and other drugs have been released from coated stents in a like manner for a variety of reasons, including mitigating the initial stress of placement of the stent. But it may be that an uncoated fabric in contact with the annulus of a heart valve, for example, might be otherwise desirable, such as to allow cell ingrowth to fix the valve in place. Using a thin outermost layer of a cuff material of the disclosure, for example made of one or more bio-absorbable/biodegradable polymers, could facilitate drug release, then get out of the way.

Figure 20:
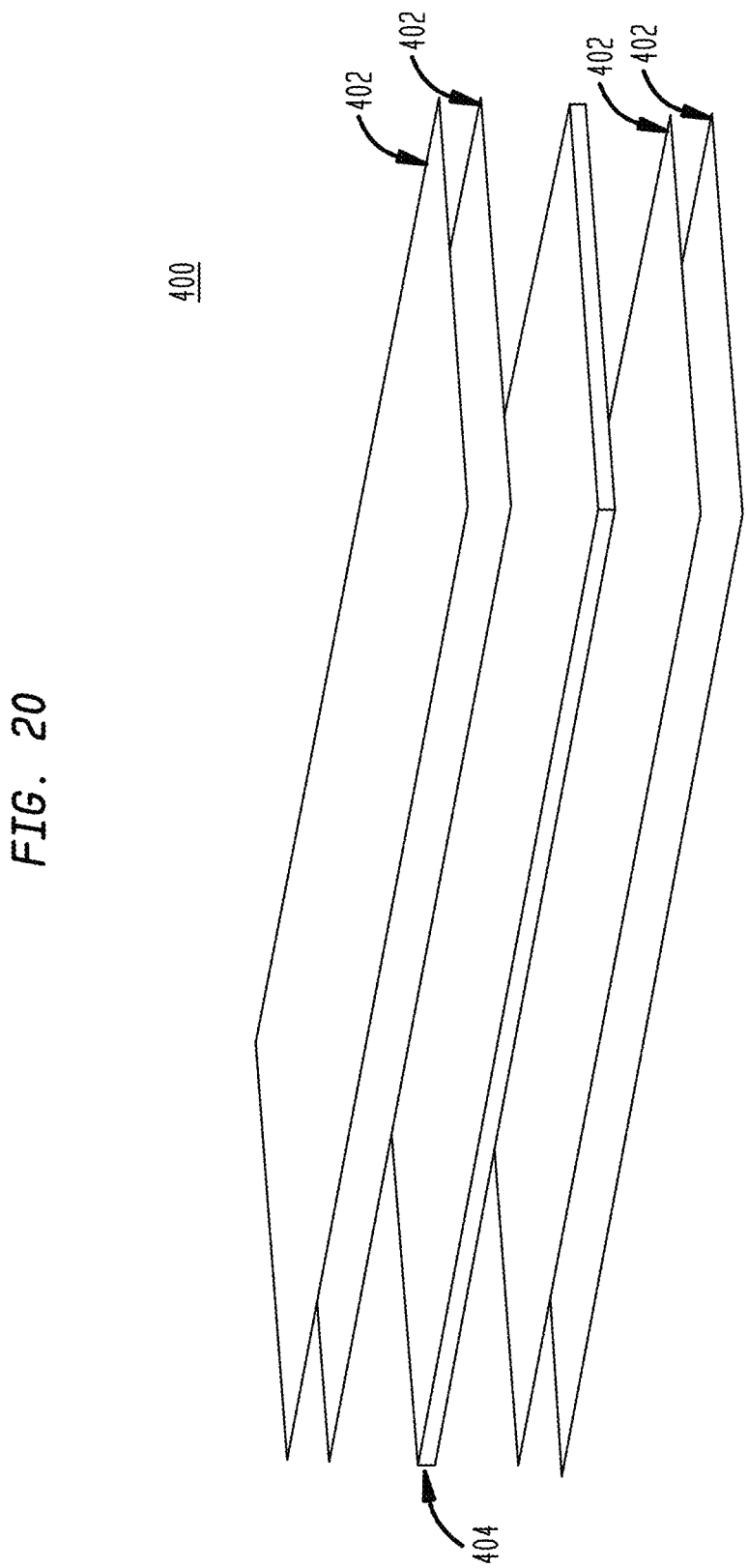
FIG. 20 is an exploded view of a coated fabric including a single fabric layer sandwiched between two polymer films or layers adhered to each side of the fabric layer.

FIG. 20 is an exploded view of an exemplary coated fabric 400 in accordance with the present disclosure useful for discussing its general structure in a non-limiting fashion. A completely coated fabric 400 can be created by heat laminating polymer film layers 402 to fabric 404. In FIG. 20, a single fabric layer 404 may be covered on only one side by a single polymer film layer 402, or the fabric layer 404 may be sandwiched between polymer film layers 402, one or two on each side of the fabric (the latter is illustrated). More complex partially coated constructs of coated fabric 400 are also possible. (See FIGS. 21-23C, 34-45B.) Two fabric layers 404 may sandwich a single or multiple polymer film layers 402 and an outer surface of at least one of the two fabric layers 404 may be covered with another polymer film layer 402. It should be noted that the use of the terms "polymer film" and "polymer film layer" herein is not intended to be limited to the application of one or more discrete preformed polymer films to the fabric, but also includes one or more layers of polymer formed directly on the fabric, such as by dip coating, spray coating, 3-D printing and the like.

In some embodiments, up to 20 layers of polymer film may be applied to one or to each side of the fabric layer. In other embodiments, 1 to 10 layers of polymer film may be applied to one or to both sides of the fabric layer. In still other embodiments, 1 to 5 layers of polymer film may be applied to one or to both sides of the fabric layer. Thus, each side of the fabric layer can be covered, completely or partially, by 1, 2, 3, 4, 5, 6, 7, 8, 9, 10, 11, 12, 13, 14, 15, 16, 17, 18, 19, or 20 polymer film layers.

When more than one coating layer is used, the various layers need not each have the same thickness or, as noted previously, the same composition or orientation. While even thicker coatings are possible, generally speaking, the thickness of the coating on each side, whether comprised of 1 layer or 20, may range from about 0.5 μm to about 100 μm, in another embodiment from about 0.5 μm to about 50 μm, and in some further embodiments from about 10 μm to about 40 μm. In one other embodiment, the thickness of the coating on each side may range from about 15 μm to about 30 μm. Very thin polymer layers, i.e., from about 0.50 μm to about 2 μm, may be applied simply to fill the open pores in the fabric or for other reasons.

A resultant coated fabric in accordance with the disclosure often will be thicker than an uncoated fabric. The overall thickness of a coated fabric could be as high as about 500 μm, or even higher (about 1,000 μm), depending on the fabric being used, the type and number of coatings, and the intended use of the fabric. If the coating is being applied just at or adjacent the attachment edge of a leaflet such that it can be sewn through when attaching the leaflet to a cuff and/or stent, it can be relatively thicker as it will not impact the flexibility of the balance of the leaflet. The thickness of the leaflet could also vary along a gradient, such as from the attachment edge to the free edge of the leaflet. In general, the coated fabric will have a maximum thickness in some embodiments of no more than about 500 μm, in other embodiments of no more than about 250 μm, and in still other embodiments of no more than about 200 μm.

It will be appreciated that the thicknesses of the polymer film layers and the coated fabric are dictated by a balancing of properties and functionality. The number of layers of polymer film applied to the fabric can have an impact on the size to which a collapsible medical device, such as a collapsible prosthetic heart valve, can be collapsed. For non-collapsible devices, such as prosthetic heart valves that are only expandable and surgical heart valves, collapsibility is not a factor dictating thickness. In such instances, other properties may dictate composition, number of layers and thickness, such as, without limitation, rigidity, porosity, stability and flexibility. Of course, there are many other factors involved as well including, without limitation, the size and geometry of the stent or other medical devices to which the coated fabric may be applied or attached.

Producing coated fabrics may be accomplished by any known method. U.S. Pat. No. 2,852,811, for example, describes methods for casting thin plastic films, particularly those composed of polytetrahaloethylene. U.S. Pat. No. 4,610,918 describes the production of fluoropolymer coated textiles and U.S. Pat. No. 7,109,135 relates to a woven fabric sandwiched between PTFE layers. In some embodiments, the polymer layers may be extruded via any extrusion mechanism known to those of skill in the art and applied or laminated to fabrics using heat and pressure, such as rollers. In some embodiments, polymer layers may be bonded to fabric layers using an adhesive or adhesion promoting agent. The polymer layers may also be formed in situ by spray coating or dip coating the fabric layers, or a side thereof, with a polymer that will dry, or that can be cross-linked, to form a layer or layers. The coatings and partial coatings may also be applied by 3D printing. The coated fabric may also include intermediate materials or layers intended to improve adhesion between the polymer layers and the fabric layers.

FIGS. 21-23 and 34-42 illustrate certain exemplary structures that can result from the formation of a partial coating. The partial coatings forming these structures can, of course, be applied to a fabric layer in a manner similar to complete coatings. For example, polymer films of the desired shape and size can be placed where desired and glued, laminated, etc. in place; liquid polymer can be molded to the shape desired; or an edge of the fabric can be dip coated. However, a partial coating may also be achieved by fully coating a major surface of the fabric layer (or a partially or fully coated fabric layer) and then removing unwanted portions of that coating or unwanted portions of specific layers by ablating, melting, evaporating, cutting, eroding or frictionally removing (sanding, grinding, rubbing). Thus ribs, reinforced areas adjacent an attachment region, and structures at or adjacent the free edge used to resist wear can all be formed by removing the coating material between those structures.

Ablation can also be used to provide a pattern in a coated surface or to impart other surface features. Ablation could be used, for example, to taper the thickness of a leaflet, just for example, from an attachment edge to the free edge. This is accomplished by progressively ablating the coating layer(s) from one edge to the other, deeper and deeper, thus removing more and more of the coating. As another example, ablation could be used to remove a portion of the coating(s) in a selected area, such as in the portion of a leaflet that will form its belly when in use in a heart valve, to provide additional flexibility to that region. Other surface patterns may also be developed. In addition, surface roughening, such as to promote cell adhesion generally or in specific areas of the surface, may be employed.

When ablation is used, it may be preferable to use a single thicker coating layer rather than multiple layers. In other circumstances, the top most layers that will be selectively ablated could be composed of one polymer material, with one or more under layers that are not to be removed or patterned being composed of a different polymer material. Indeed, while these processes for removing portions of a full coating have just been described in connection with forming partial coatings, they may also be used to provide patterns and/or surface features in complete coatings where no portion of the major surface of the fabric is substantially uncoated. See, for example, FIG. 37, which contains a full coating 3751 disposed between fiber layer 3740 and an additional coating feature 3750 adjacent the free edge 3730. Layer 3750 could be applied to polymer layer 3571 or it could be formed by ablating away a portion of a top layer leaving only portion 3750.

The polymer layer or layers may therefore form a pattern or relief on one or both sides of a fabric layer. They may vary thickness; provide rigidity or additional cohesion to specific regions; retard fraying; reinforce shape, stretch, or friction; alter porosity; provide or encourage cell attachment or prohibit it in specific areas; enhance coaptation; and the like.

Figure 21:
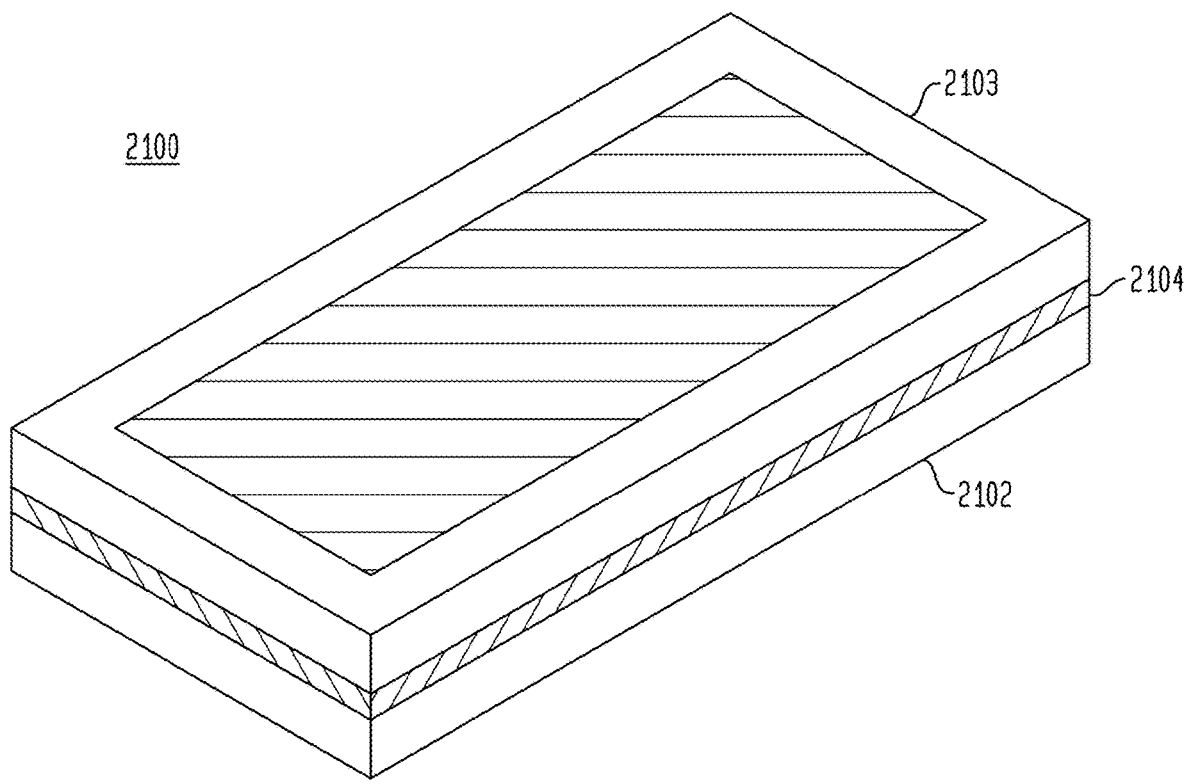
FIG. 21 is a perspective view of a fabric having a polymer film or layer on the edges of the top surface of the fabric layer.

FIG. 21 illustrates a non-limiting example of a coated fabric 2100 which may be patterned as shown. A fabric layer 2104 may be discontinuously coated with a polymer layer 2103 such that only the area a few millimeters from each edge of the top major surface of the fabric layer 2104 is polymer coated—forming a structure looking like a picture in a frame, as shown in FIG. 21. The bottom major surface of the fabric layer 2104 may be continuously coated with a polymer layer 2102. The reverse may also be possible. A checkerboard pattern, a series of strips, concentric circles or other shapes may be laminated, printed, etched, masked, coated or otherwise formed onto one or more major surfaces of the fabric. Each of these patterns can be formed by using differing thicknesses and/or different numbers of layers of polymer. The entire upper surface of a fabric could be coated. Alternatively, different portions of the surface could be coated with different thicknesses and/or different numbers of layers of polymer. This can be done to provide a coated fabric with areas of greater or lesser porosity, areas of greater or lesser surface irregularity or roughness, areas of different texture, and/or areas of greater flexibility or rigidity. Controlled coating of the fabric may also provide preferred movement or folding, reinforcement of certain areas, greater wear resistance, areas in which it is harder for a tear to form or propagate near a suture, or a combination of any of these.

Figure 22:
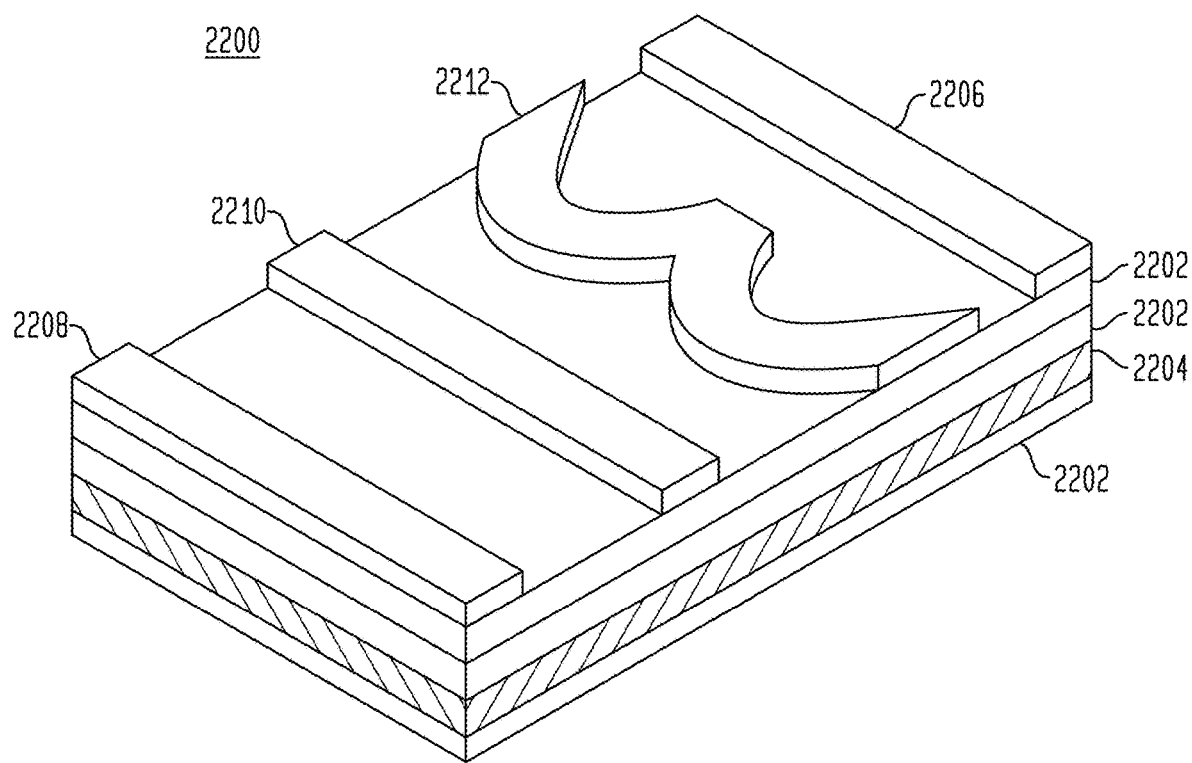
FIG. 22 is a perspective view of a fabric having a structured upper surface and a different number of polymer layers on each side of the fabric layer.

FIG. 22 illustrates another example of a partially coated fabric 2200 in which a fabric layer 2204 may be coated on its entire lower surface with a single polymer layer 2202. However, two continuous polymer layers 2202 may be applied to the upper surface of fabric layer 2204, and a third polymer layer may be printed or otherwise applied thereto in a discontinuous fashion over the continuous layers. A portion of this third layer may be, in this example, applied to the continuous layers 2202 so as to overlie two opposed edges 2206 and 2208 of the coated fabric 2200. This could be done to reinforce those areas of the coated fabric that may be attached with, for example, sutures, to the luminal and abluminal surfaces of a stent and wrapped around the inflow end of the stent to provide internal and external cuffs. Another portion of the third layer may include a curved portion 2212 to help reinforce that portion of the resulting inner cuff at which leaflets will likely be attached. The third layer may also include another strip 2210 located in the area of the coated fabric 2200 which will actually wrap around the inflow end of the stent to help prevent abrasion upon contact between the cuffs and the stent and to provide a sturdier portion for suturing to the inflow end of the stent.

Figure 23A:
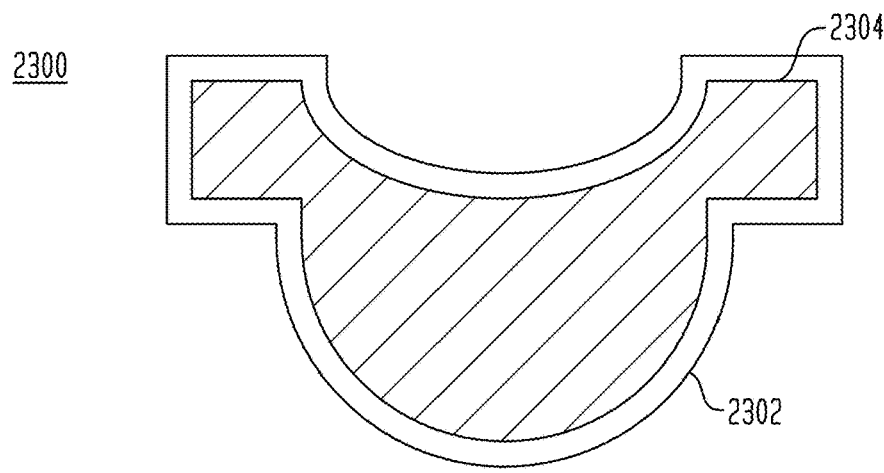
FIG. 23A is a plan view of a leaflet coated on the edges of the fabric layer.
Figure 23B:
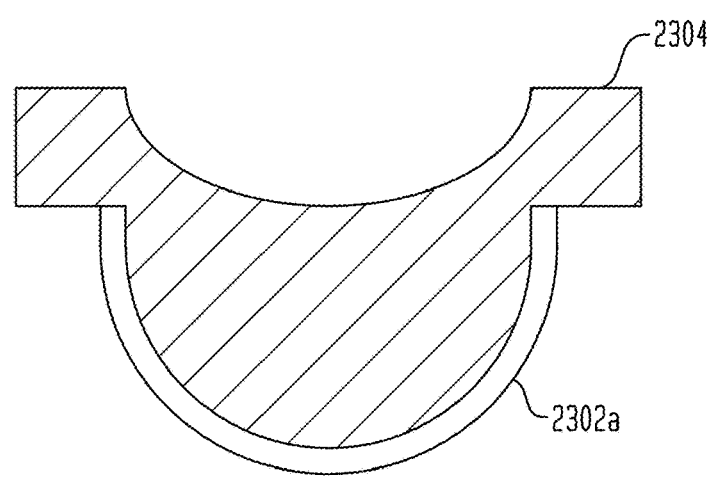
FIG. 23B is a plan view of the underside of the leaflet coated along the sewing edge.
Figure 23C:
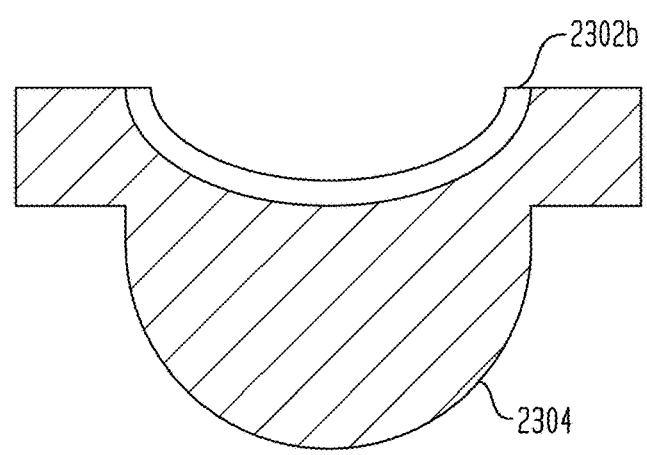
FIG. 23C is a plan view of the top side of the leaflet coated along the free edge.

FIGS. 23A-23C, for example, illustrate a patterned coated fabric for use in a leaflet 2300. The fabric layer 2304 may be discontinuously coated with a polymer layer 2302 such that only the area a few millimeters from each edge of the fabric layer is coated. The pattern as just described may be used for a leaflet in which only the attachment edge and the free edge of the leaflet are coated, as shown in FIG. 23A. In some embodiments, the pattern as just described for a leaflet may have a fabric layer discontinuously coated with a polymer layer such that an area extending about 10 mm from the attachment edge and the free edge is coated with the polymer. In other embodiments, the coating areas may not be uniform and the fabric 2304 may be coated in an area extending about 10 mm from the attachment edge with polymer 2302*a* and in an area extending about 5 mm from the free edge with polymer 2302*b*, as is shown in FIG. 23B and FIG. 23C, respectively. FIG. 23B illustrates the underside (or upstream surface) of the leaflet which attaches to the stent, while FIG. 23C illustrates the other side (or downstream surface) of the leaflet. The reverse may also be possible when used for a leaflet.

Figure 24:
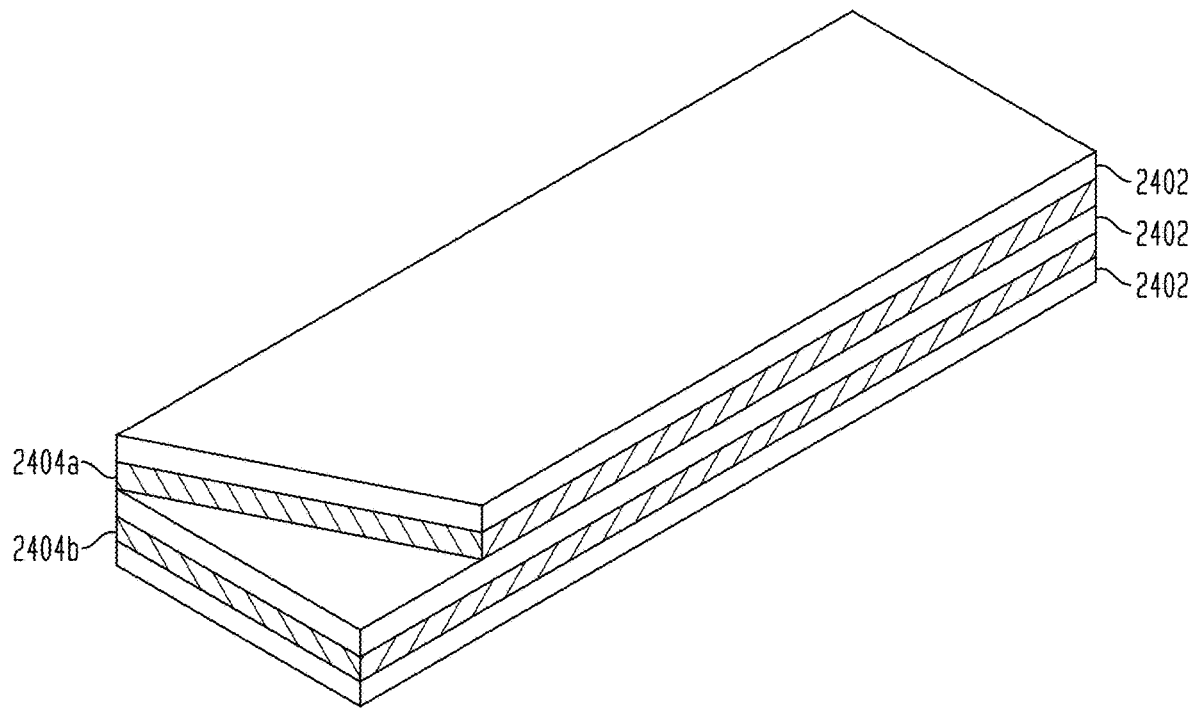
FIG. 24 is a perspective view of a coated fabric having multiple layers of fabric and at least one polymer layer between each fabric layer.

FIG. 24 illustrates a coated fabric composed of multiple polymer layers and multiple fabric layers. The fabric layers may be oriented such that their warp fibers either are oriented substantially parallel to the longitudinal edges of the coated fabric (not on a bias), or at a bias of between about 30 degrees and about 60 degrees relative to the longitudinal edges of the coated fabric. The coated fabric with multiple polymer layers and multiple fabric layers may be formed by alternating each polymer layer with a fabric layer such that each fabric layer has a polymer layer on both its top surface and its bottom surface. In FIG. 24, a first fabric layer 2404*a* is oriented at about a 45 degree bias relative to the longitudinal edges of the coated fabric, while second fabric layer 2404*b* is not oriented on a bias. Each fabric layer 2404*a*, 2404*b* may be coated with a polymer layer 2402.

Figure 25:
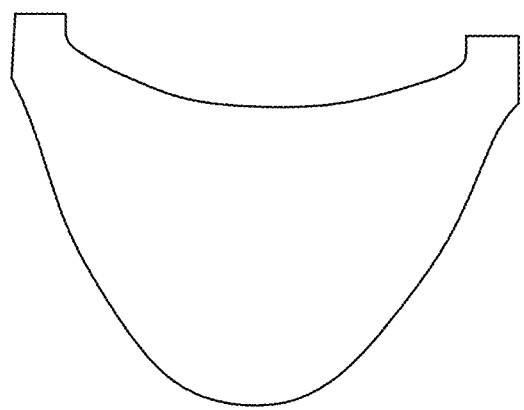
FIG. 25 is a plan view of a heart valve leaflet fabricated from UHMWPE fibers.
Figure 26:
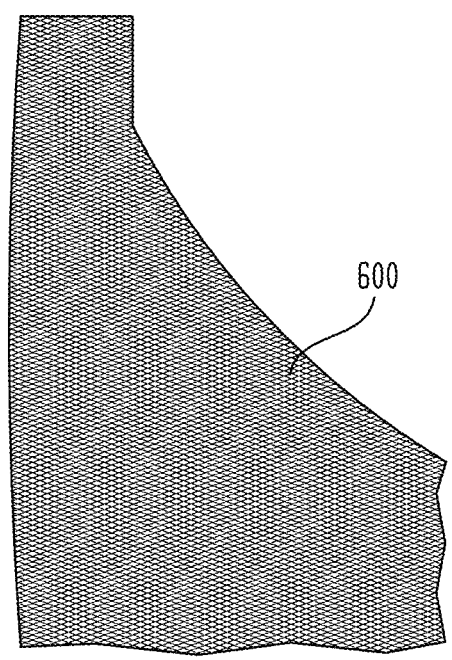
FIG. 26 is an enlarged view of a portion of the heart valve leaflet of FIG. 25.

FIGS. 25 and 26 depict a heart valve leaflet fabricated from a fabric composed of UHMWPE fibers. The fabric may be cut to a desired geometry by stamping, mechanical cutting, laser cutting or other known techniques. As shown in FIG. 25, the UHMWPE fabric is cut to produce a heart valve leaflet having fibers 600 oriented at a 45 degree angle relative to the direction from the attachment edge to the free edge of the leaflet. FIG. 26 shows an enlarged portion of the heart valve leaflet of FIG. 25 showing the edge quality of the heart valve leaflet produced by laser cutting. The laser cutting may melt the edges of the leaflets to effectively create a single, continuous seam. There may be a preference for a smooth transition between the main leaflet body and the edges of the leaflet. If the transition is not smooth, blood cells may encounter a relatively large amount of shear stress at the transition point, which can activate the blood cells, creating a potential for undesirable thrombus formation. The edges of the leaflet may be coated with a polymer as described above to ensure a smooth transition between the main leaflet body and the edges of the leaflet. In still further embodiments, at least one of the leaflets may be composed of a woven or knitted fabric that is coated or uncoated and fabricated such that its fibers are at a bias angle of between about 30 degrees and about 60 degrees relative to a line that extends perpendicular to the free edge of the leaflet when the leaflet is in a flattened condition or lies within a plane (e.g., before the leaflet is attached to the valve assembly). In another embodiment, all of the leaflets may be fabricated with their fibers at that same relative bias. In still a further embodiment, the leaflets may not all be fabricated with their fibers at that same bias. In one such instance, all of the leaflets may be fabricated with their fibers on a bias of between about 30 degrees and about 60 degrees relative to a line that extends perpendicular to the free edge of the leaflet, but the fibers of at least one of the leaflets are not on the same bias as the fibers of the other leaflets of the valve assembly. In still another such embodiment, the fibers of at least one such leaflet are biased at between about 30 degrees and about 60 degrees relative to a line that extends perpendicular to the free edge of the leaflet and the fibers of at least one other leaflet are not.

FIGS. 28-46A further illustrate the structural diversity of coated and uncoated synthetic fabrics useful in medical devices in accordance with the present disclosure. This diversity is illustrated by using leaflets and cuffs useful in the construction of collapsible/expandable heart valves. It should be understood, however, that these structures are illustrative and that the fabric materials depicted can be used in other medical devices and their shape, thickness, and composition may be adjusted to suit that particular purpose.

Looking at FIG. 28, leaflet 2808, an uncoated leaflet, consists only of a fabric 2840. Leaflet 2808 includes a first major surface or downstream surface 2815 and a second major surface or upstream surface 2820. Leaflet 2808 is similar to leaflet 108 shown in FIG. 2 attached to a stent so as to form a one-way valve assembly. The actual surface illustrated in FIG. 2 is the first major surface or downstream surface as blood flows into the valve from the inflow or annulus end 130 to the outflow or aortic end 132. Blood flows from upstream to downstream and, accordingly, the first major surface is considered the downstream side with the downstream surface 2815 and the opposite major surface is the upstream surface 2820. Stated in another way, the downstream surface 2815 is the major surface generally facing the outflow or aortic end 132 of the stent when the valve leaflets are in a closed position during use. The upstream surface 2820 generally faces the inflow or annulus end 130 of the stent when the leaflets are in the closed position.

Leaflet 2808 has a free edge 2830, a attachment edge 2825, and a plurality of tabs or flaps 2835. Generally, the leaflet is attached to the cuff and/or to the stent at or adjacent the attachment edge 2825. The tabs 2835 often form commissures at which two adjacent leaflets meet. Each tab 2835 is often attached to an adjacent tab of an adjacent leaflet and/or to the stent at, for example, a commissure attachment feature such as element 116 in FIG. 2. While much of the fabric moves during operation of the prosthetic heart valve, the greatest degree of movement is experienced by the free edge 2830. It is pushed out of the way from the center of the valve toward the luminal surface of the stent when blood is flowing, and is pushed back toward the center of the valve where it engages or coapts with other leaflets when the valve is closed.

As noted, the fabric leaflet 2808 in FIG. 28 is uncoated, and it can be composed of any uncoated at least partially synthetic fabric as disclosed herein. Leaflet 2808 is illustrated as a single layer of fabric, although multiple layers of fabric could be stacked directly atop one another and attached to one another by suitable methods, such as gluing, stitching, spot welding, and the like.

Figure 29:
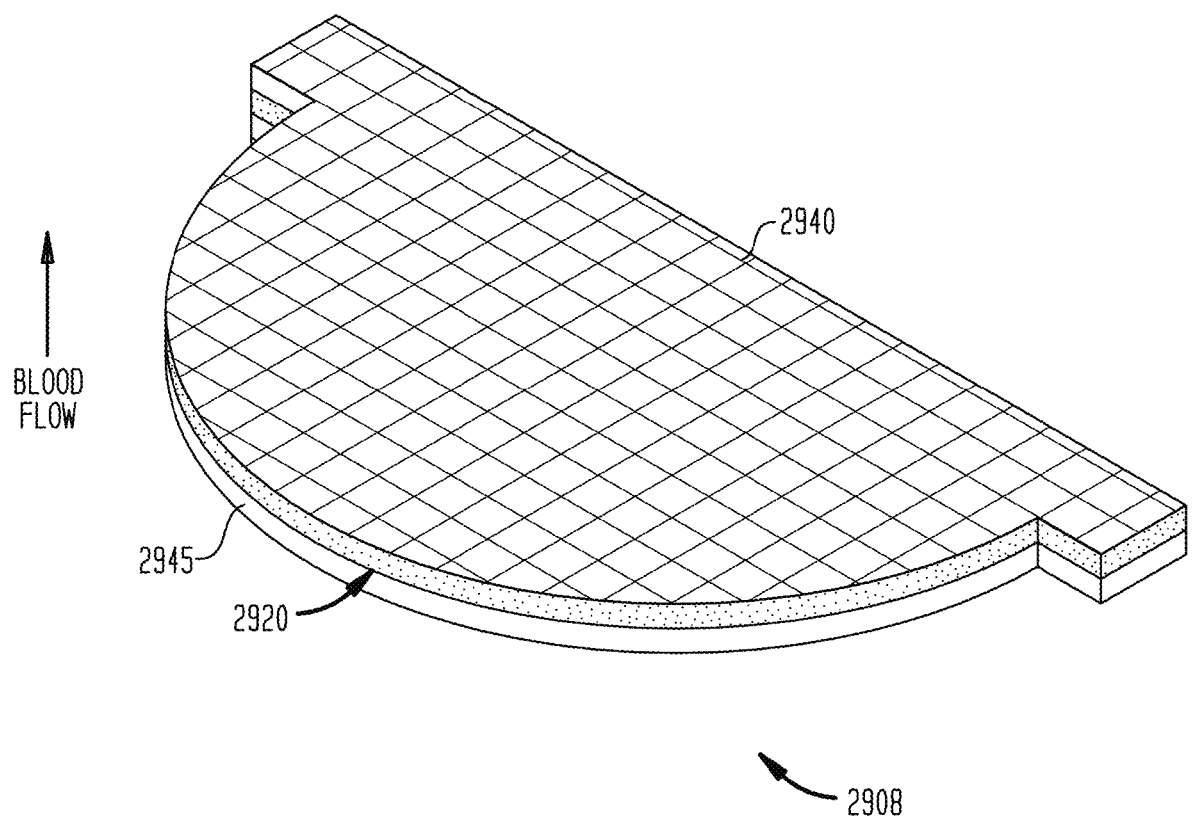
FIG. 29 is a schematic perspective view of a leaflet formed from a coated fabric according to the present disclosure.

FIG. 29 illustrates a coated fabric and is generally of the same structure and composition as that illustrated in FIG. 28, other than the coating. The leaflet 2908 in FIG. 29 includes a fabric layer 2940, which can be composed of any of the fabrics disclosed herein, as well as a polymer layer 2945. In FIG. 29, polymer layer 2945 is generally coextensive with the shape and size of fabric layer 2940 and is attached to the upstream surface 2920 of the fabric layer. Fabric layer 2940 and polymer layer 2945 are illustrated as being of roughly the same thickness, however, that need not be the case. Multiple fabric layers and/or multiple polymer layers are possible and contemplated as described elsewhere herein.

Moreover, the leaflet 2908 in FIG. 29 is illustrated with the downstream surface not covered by a polymer layer. It can, however, be covered by one or more polymer layers as well. Indeed, this concept is illustrated in FIG. 30.

Figure 30:
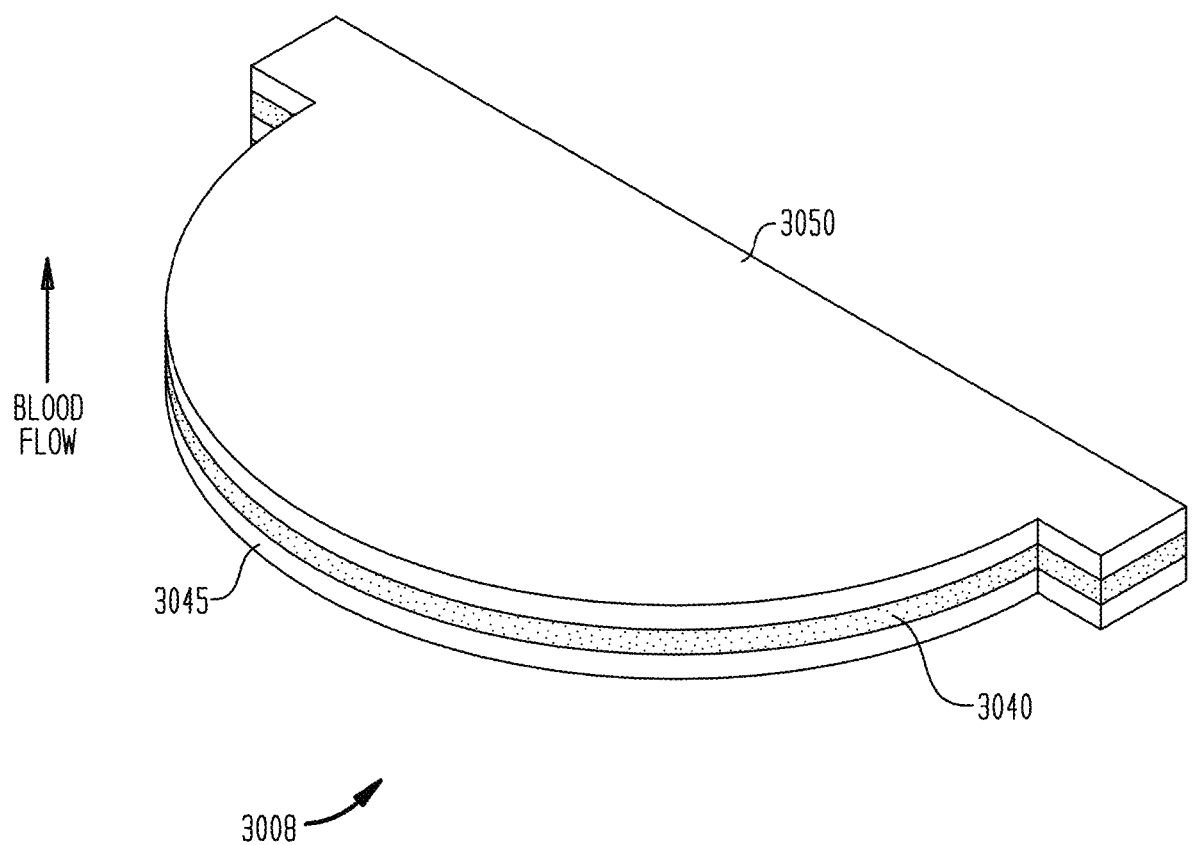
FIG. 30 is a schematic perspective view of a leaflet formed from another coated fabric according to the present disclosure.

FIG. 30 illustrates a valve leaflet 3008 as generally described in FIGS. 28 and 29 comprised of a fabric layer 3040, a first polymer layer 3045 covering the entire upstream surface of the fabric layer and a second polymer layer 3050 covering the entire downstream surface of the fabric layer. As before, the individual layers can be made of any of the fabrics and any of the polymer coating materials described herein. While a leaflet having three layers is illustrated, more layers are possible, and the layers may be of varying thicknesses.

Figure 31:
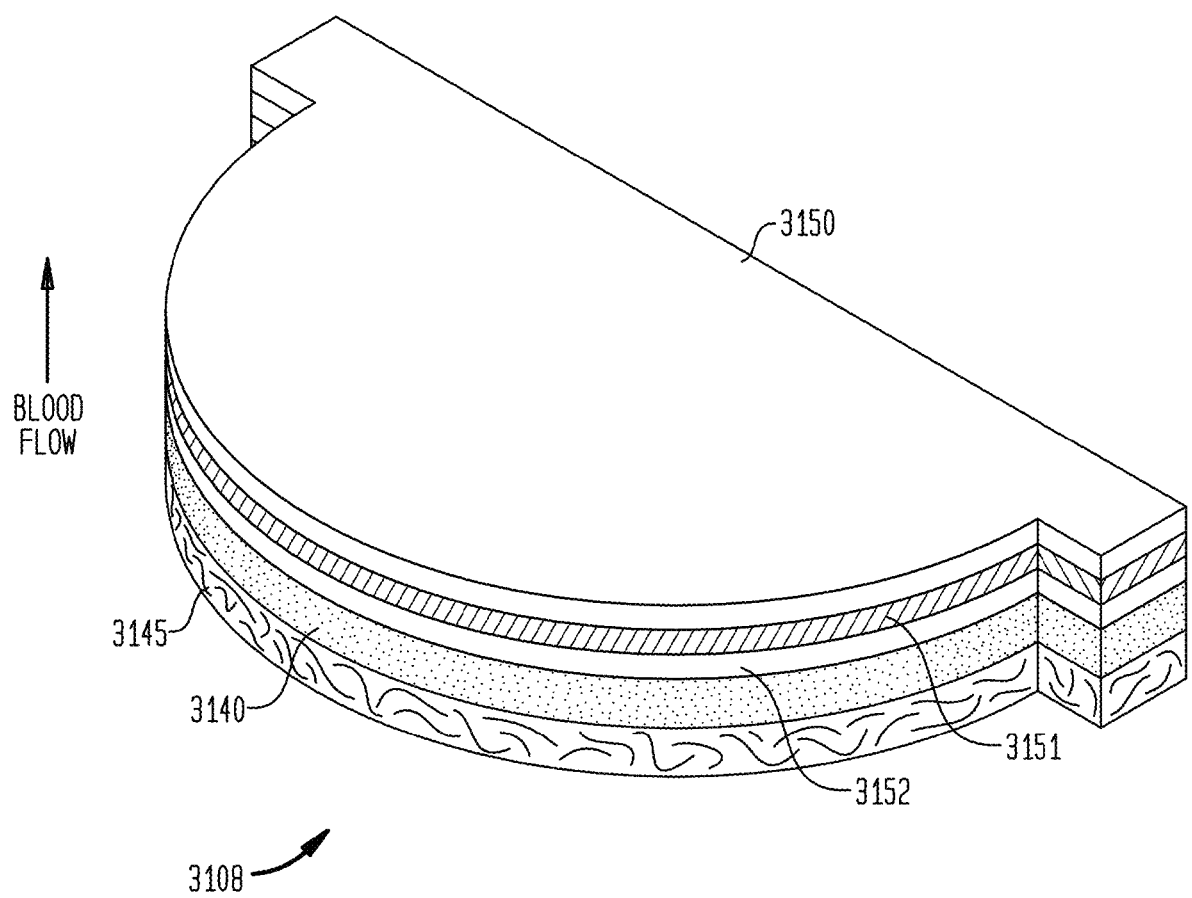
FIG. 31 is a schematic perspective view of a leaflet formed from another coated fabric according to the present disclosure.

Similarly, FIG. 31 illustrates a leaflet 3108 as described in connection with FIGS. 28-30. Leaflet 3108 has a multilayered structure in which the fabric layer 3140 is coated on both of its major surfaces with at least one polymer layer. Leaflet 3108 contains a fabric layer 3140 as discussed herein, and a single polymer layer 3145 covering the entire upstream surface of the fabric layer. There are, however, three polymer layers covering and attached to, directly or indirectly, the entire downstream surface of leaflet 3108. The most downstream or outermost layer 3150 may be made of ultra-high molecular weight polyethylene (UHMWPE), the next adjacent layer 3151 may be made of low density polyethylene, and the third and final layer 3152 situated against the fabric layer 3140 may also be composed of UHMWPE.

The three polymer layers 3150, 3151, and 3152 illustrated in FIG. 31 have roughly the same combined thickness as polymer layer 3145 disposed on the upstream surface of fabric layer 3140. This need not be the case. Each of the individual polymer layers may be thin or thick and their combination may be thicker or thinner than polymer layer 3145 or fabric layer 3140. Moreover, while three polymer layers are illustrated, as discussed elsewhere herein, the number of layers that can be applied to any one major surface of the fabric layer can be as many as 20 layers.

Figure 32:
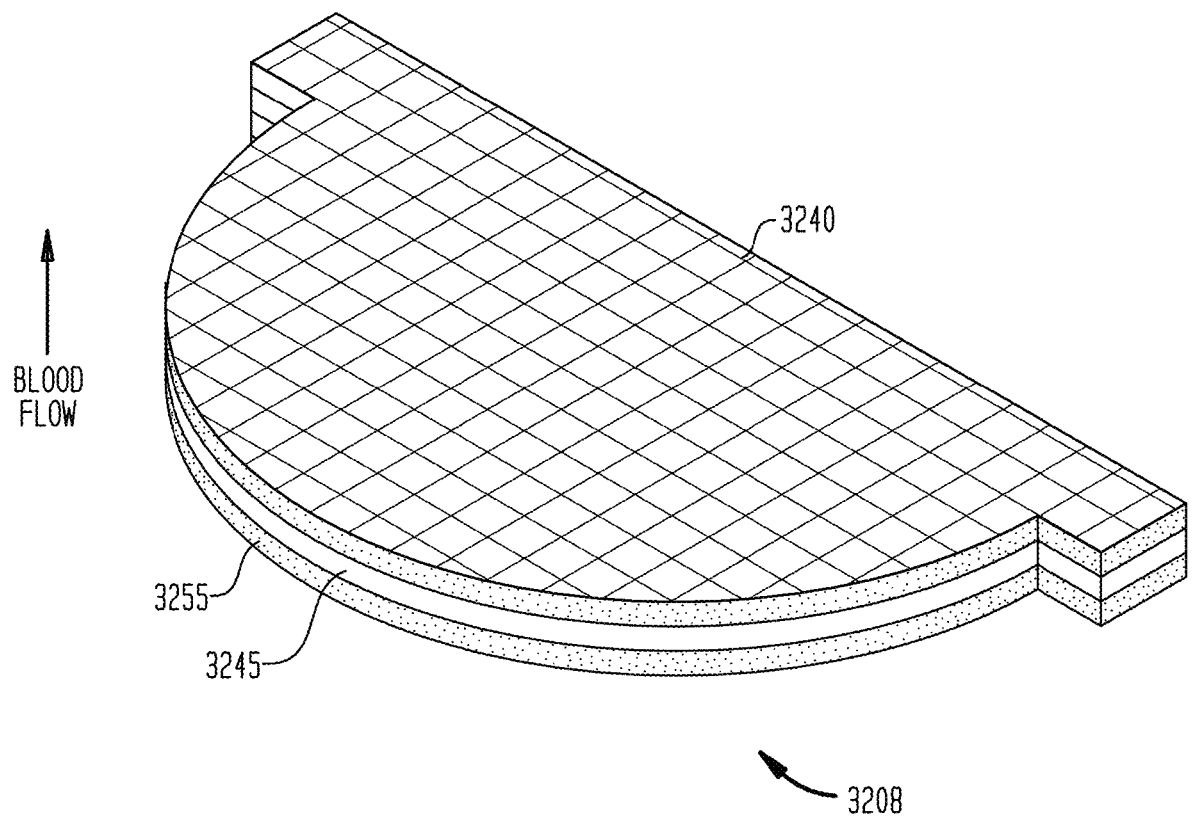
FIG. 32 is a schematic perspective view of a leaflet formed from another coated fabric according to the present disclosure.

FIG. 32 shows another construction of a leaflet generally discussed and illustrated in FIGS. 28-31. Leaflet 3208, however, includes two fabric layers separated by, and each attached to, a polymer layer disposed between them. Specifically, fabric layer 3240 forms a downstream side of leaflet 3208 and fabric layer 3255 forms the upstream side of the leaflet. Fabric layers 3240 and 3255 may be the same as one another, or may be different from one another in composition, thread count, fiber orientation, weave pattern, thickness, etc. A polymer layer 3245 is disposed between and is coextensive with the second (upstream) major surface of fabric layer 3240 and the first (downstream) major surface of fabric layer 3255. Fabric layers 3240 and 3255 may be the same as or different from one another in composition, structure, thickness, etc., and each may be a single layer or multiple layers independently of one another. While a single polymer layer 3245 is illustrated between the fabric layers, this layer could be composed of multiple polymer layers having the same or different structures, thicknesses, and compositions.

Figure 33:
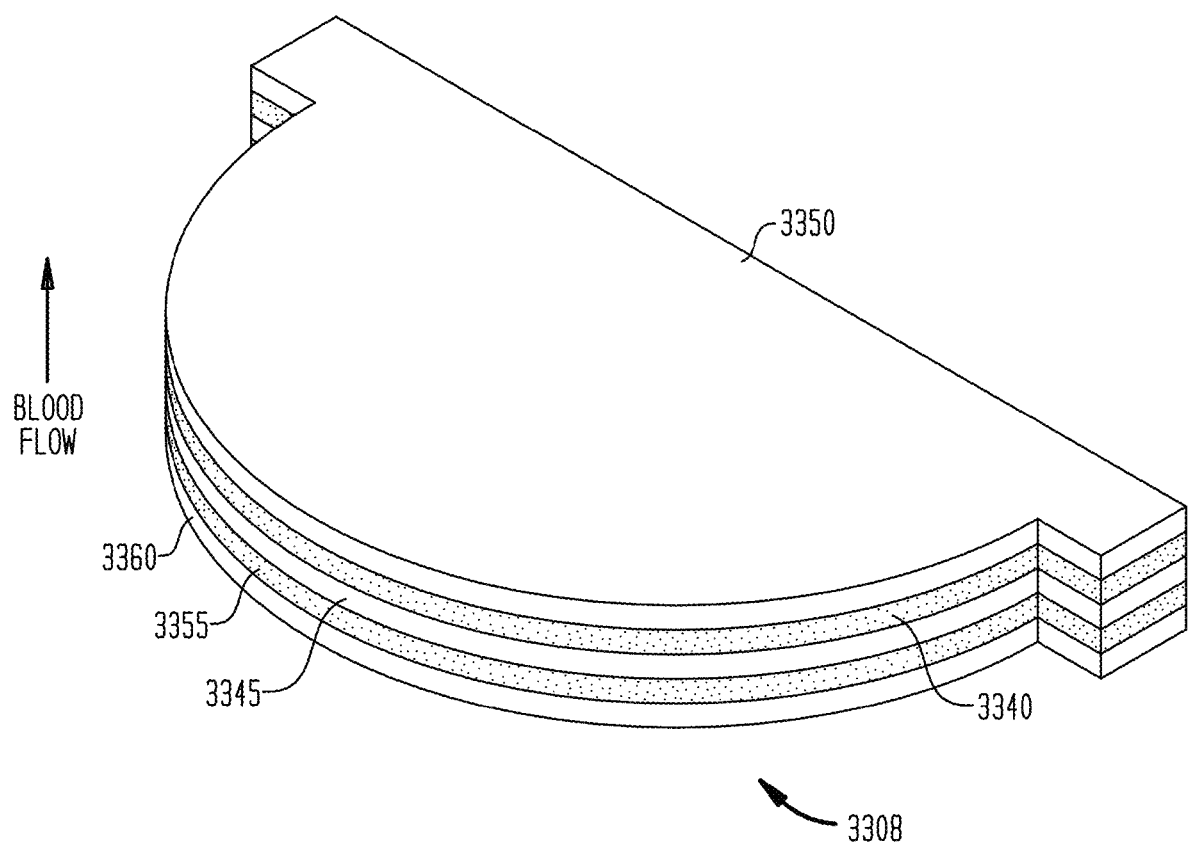
FIG. 33 is a schematic perspective view of a leaflet formed from another coated fabric according to the present disclosure.

FIG. 33 illustrates yet another possible construction of a fabric leaflet, as generally described in connection with FIGS. 28-32. Leaflet 3308 is constructed with two fabric layers 3340 and 3355, and a polymer layer 3345 disposed between them. Additionally, the downstream surface of fabric layer 3340 is covered with a polymer layer 3350 and the upstream surface of fabric layer 3355 of leaflet 3308 is also covered with a polymer layer 3360. Fabric layers 3340 and 3355 may be the same as one another, or may be different from one another in composition, thread count, fiber orientation, weave pattern, thickness, etc. Similarly, polymer layers 3345, 3350 and 3360 may be the same as one another or may be different from one another in structure, composition, thickness, etc.

Figure 34:
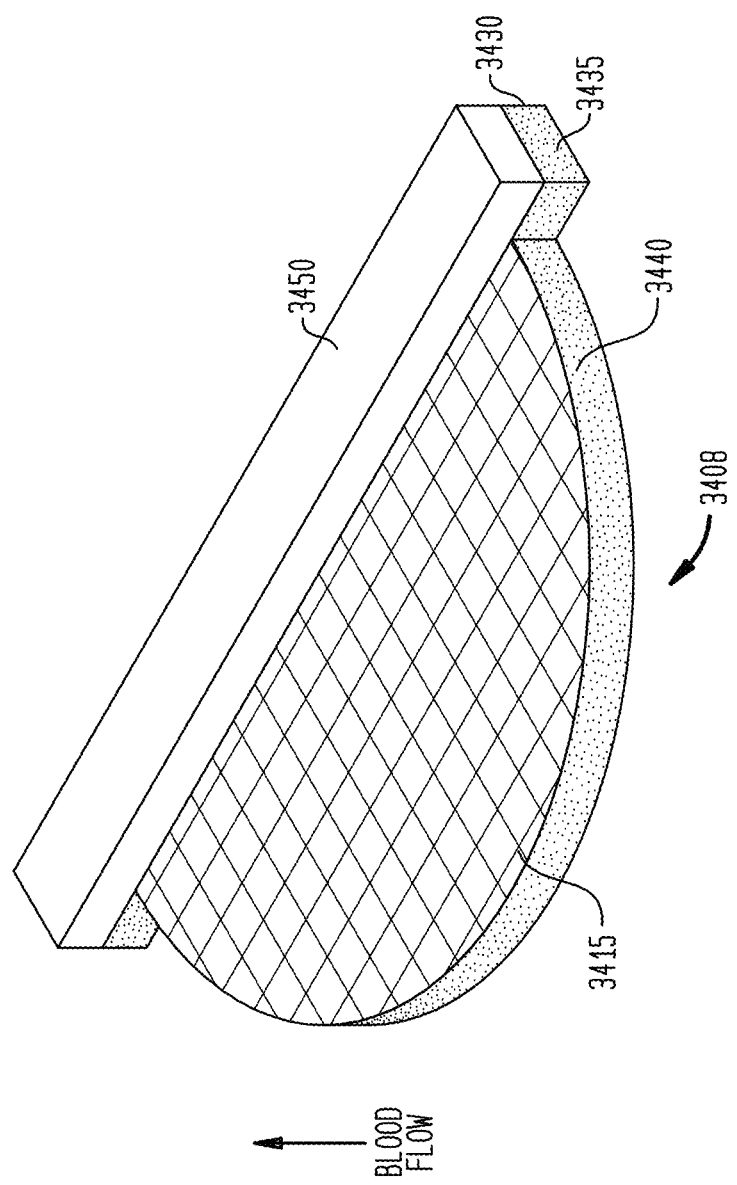
FIG. 34 is a schematic perspective view of a leaflet formed from a partially coated fabric according to the present disclosure.

FIG. 34 illustrates a partially coated leaflet 3408. Leaflet 3408 comprises a fabric layer 3440. Any fabric described in accordance with the disclosure may be used. Leaflet 3408 also includes a partial polymer coating 3450 disposed as a single layer on its downstream surface 3415 adjacent the free edge 3430 of the leaflet. This partial polymer layer 3450 is illustrated as being the same width as tabs 3435 and roughly the same thickness as fabric layer 3440. However, that need not be the case. Polymer layer 3450 may be wider or narrower across the downstream face 3415 of fabric layer 3440 and may be thicker or thinner than the fabric layer. That said, layer 3450 is often thinner and not as wide as the fabric layer. Multiple polymer layers and fabric layers may be used as opposed to the single layers illustrated. The partial coating 3450 adjacent the free edge 3430 of leaflet 3408 may serve one or more purposes. For example, it may help add weight to bias the leaflet back into a closed position, it may help the leaflet retain its intended shape, and may promote or prevent cell attachment and proliferation adjacent the free edge 3430.

Figure 34A:
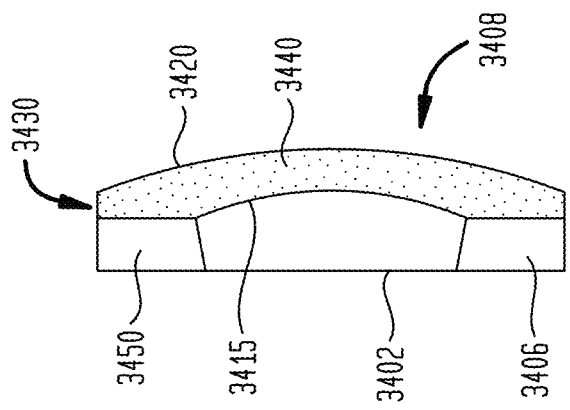
FIG. 34A is a schematic partial cross-section of a stent and a valve assembly incorporating the leaflet of FIG. 34.

FIG. 34A is a partial cross-section of a stent and a valve assembly similar to those shown in FIG. 2. A portion of the stent 3402 is illustrated in cross-section with an internal cuff 3406 attached to a luminal surface of the stent. Leaflet 3408 is attached to cuff 3406 and/or stent 3402 at or adjacent its attachment edge 3425, which may be sutured to the cuff and/or stent. Leaflet 3408 is illustrated in its open position as it extends generally downstream to accommodate blood flow from the inflow end of the stent to the outflow end past the upstream surface 3420 of the leaflet. Partial coating 3450 is disposed on the downstream surface 3415 of the leaflet edge adjacent the free edge 3430 of fabric layer 3440 and is illustrated engaging the luminal surface of stent 3402. Partial coating 3450 therefore prevents direct contact of the fabric layer 3440 and any layer disposed on the downstream surface of the fabric layer with the inner surface of the stent during blood flow, thereby providing additional wear resistance and helping to prevent the fraying of the free edge 3430 of the fabric layer. In addition to providing resistance to wear, such partial coating 3450 could also help maintain the shape of the leaflet and its ability to coapt with other leaflets, despite cell ingrowth on the downstream surface 3415 of the leaflet. Without partial coating 3450, intercellular attachment could exert forces that could tend to pull the free edge out of proper position. Instead of, or in addition to, a partial coating 3450 on the downstream surface 3415, a similar partial coating may be applied to the upstream surface 3420 of the leaflet, adjacent the free edge 3430 or otherwise, to resist the deformation of the leaflet due to cellular ingrowth.

Partial polymer layer 3450 is shown extending fully across the entirety of the free edge 3430 of leaflet 3408 between tabs 3435. This need not be the case. Partial polymer layer 3450 may be provided adjacent free edge 3430 but not overlying tabs 3435. Further, partial polymer layer 3450 may be a discontinuous layer of two, three, or more coated portions forming in essence a dashed line adjacent free edge 3430. Still further, layer 3450 may be formed of spots or dots formed intermittently adjacent free edge 3430. Each dot or each dash may have a different thickness and/or may be composed of a different composition.

Figure 35:
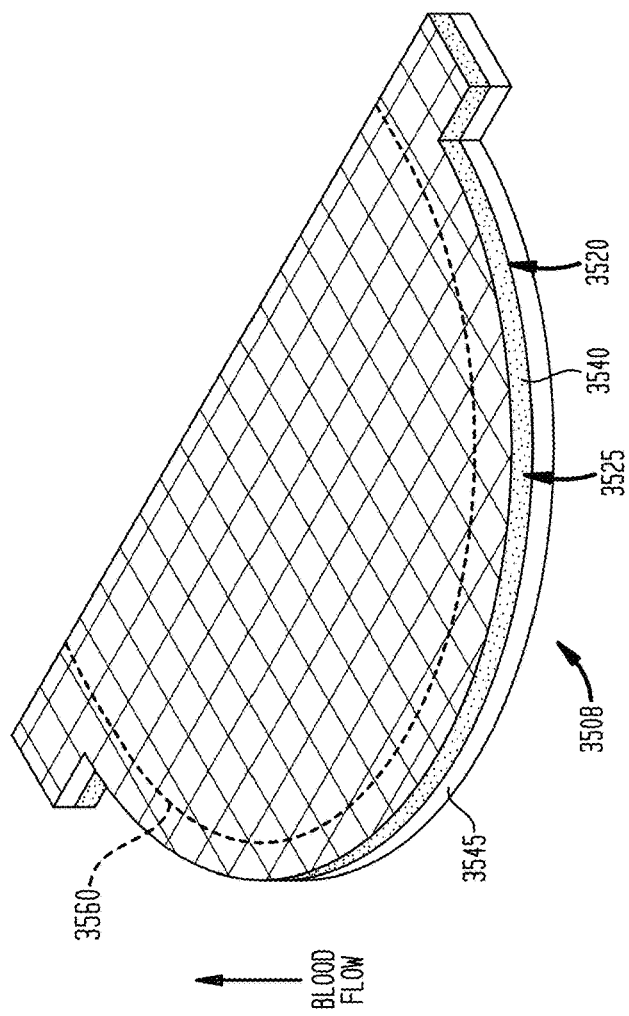
FIG. 35 is a schematic perspective view of a leaflet formed from another partially coated fabric according to the present disclosure.
Figure 35A:
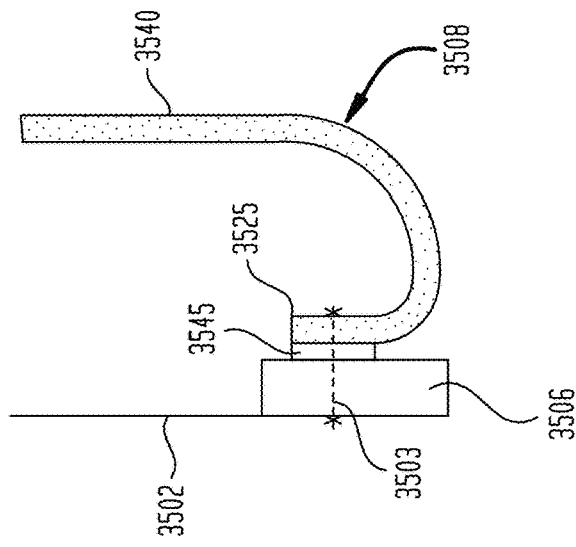
FIG. 35A is a schematic partial cross-section of a stent and a valve assembly incorporating the leaflet of FIG. 35.

FIG. 35 illustrates another embodiment of the fabric leaflets generally illustrated in FIGS. 28-34. Leaflet 3508 includes a fabric layer 3540 and a polymer layer 3545 disposed on its upstream surface 3520. Polymer layer 3545, however, does not cover the entirety of the upstream surface 3520 of fabric layer 3540. It is a relatively narrower layer in width and runs adjacent the attachment edge 3525, extending inwardly therefrom for some predefined width. An illustrative width is shown using the dashed semicircular line 3560 in FIG. 35. FIG. 35A is a partial cross-section of a stent 3502 and a valve assembly similar to those illustrated in FIG. 2. Attached to a luminal surface of stent 3502 is a cuff 3506. Leaflet 3508 as shown is composed of fabric layer 3540, which is rolled or folded adjacent its attachment edge 3525 for attachment purposes. Disposed between fabric layer 3540 and cuff 3506 is polymer layer 3545, which is provided adjacent the attachment edge 3525 of fabric layer 3540. As is true for FIG. 34A, leaflet 3508 is illustrated in the open position, e.g., a position that would be roughly when blood is flowing through the valve from the inflow end of the stent to the outflow end. Leaflet 3508 may be attached via a suture 3503 anchoring both fabric layer 3540 and polymer layer 3545 to cuff 3506 and/or stent 3502.

As was true for the partial layer 3450 in FIG. 34, the partial layer 3545 need not be a single layer nor need it be the same thickness or composition as fabric layer 3540. As was previously described, its width need not extend over the entire upstream surface 3520 of fabric layer 3540. Indeed, generally, it may be provided with sufficient width only to allow a suture therethrough. Partial layer 3545 may provide additional reinforcement and/or may help prevent fraying when suturing leaflet 3508 to cuff 3506 and/or stent 3502. It may serve other purposes as well.

Partial polymer layer 3545 is illustrated as being disposed on the upstream surface 3520 of fabric layer 3540. However, it may be disposed on the downstream surface or on both the upstream and downstream surfaces to provide additional reinforcement and/or other advantages. Partial layer 3545 also is illustrated as covering the entire attachment edge and tabs of leaflet 3508. That need not be the case. It need not be provided at the tabs and/or may be provided as discontinuous dashes or spots of varying compositions, number of layers and thicknesses as previously discussed in connection partial layer 3450 in FIG. 34.

Figure 36:
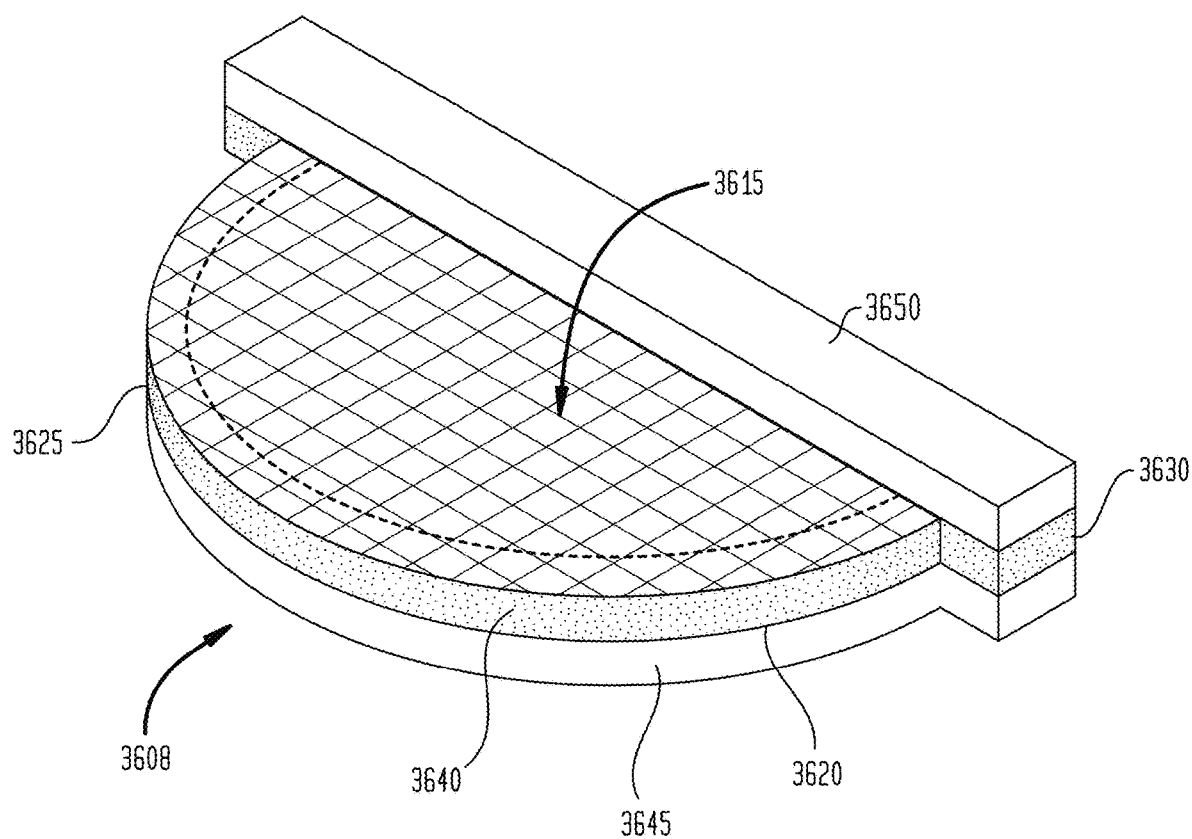
FIG. 36 is a schematic perspective view of a leaflet formed from another partially coated fabric according to the present disclosure.

FIG. 36 is an amalgam of the leaflets illustrated previously in FIGS. 34 and 35. It includes a fabric layer 3640 having attached to its downstream surface 3615 a partial polymer layer 3650 adjacent its free edge 3630. It also includes a partial polymer layer 3645 on the upstream surface 3620 of fabric layer 3640 adjacent the attachment edge 3625.

Figure 37:
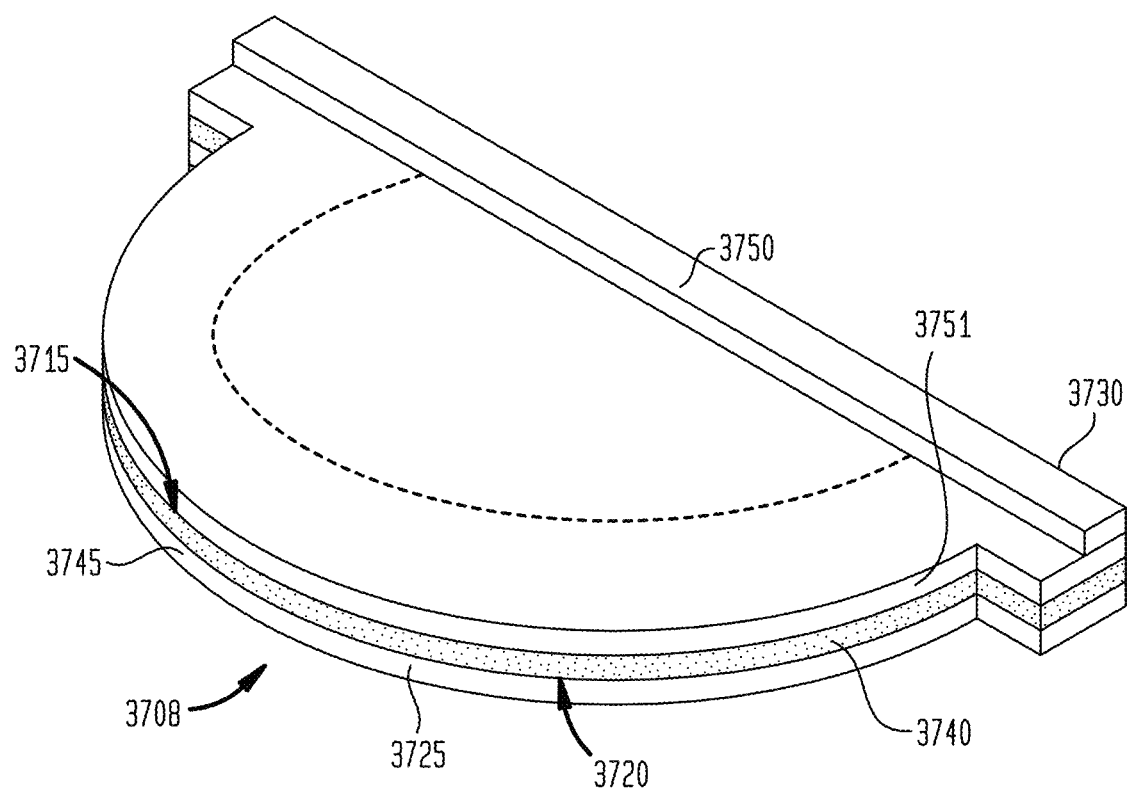
FIG. 37 is a schematic perspective view of a leaflet formed from another partially coated fabric according to the present disclosure.

FIG. 37 illustrates another embodiment of a leaflet such as described in FIGS. 28-36. Leaflet 3708 includes a fabric layer 3740 having a polymer layer 3751 applied to its entire downstream surface 3715. Adjacent the free edge 3730 is a further partial polymer layer 3750 applied atop/upon layer 3751. Partial layer 3750 may be any layer as previously described, such as, for example, partial layer 3450 in FIG. 34. Leaflet 3708 also includes a partial polymer layer 3745 attached to the upstream surface 3720 of fabric layer 3740 adjacent the attachment edge 3725, generally as described for partial polymer layer 3545 in FIG. 35.

As illustrated in FIG. 37, however, the width of polymer layer 3745 adjacent the attachment edge 3725 is much greater than the width of polymer layer 3750 adjacent the free edge 3730 of leaflet 3708. This is meant merely to illustrate the fact that there are partial layers on various surfaces of a leaflet and that they may independently have different widths.

Figure 38:
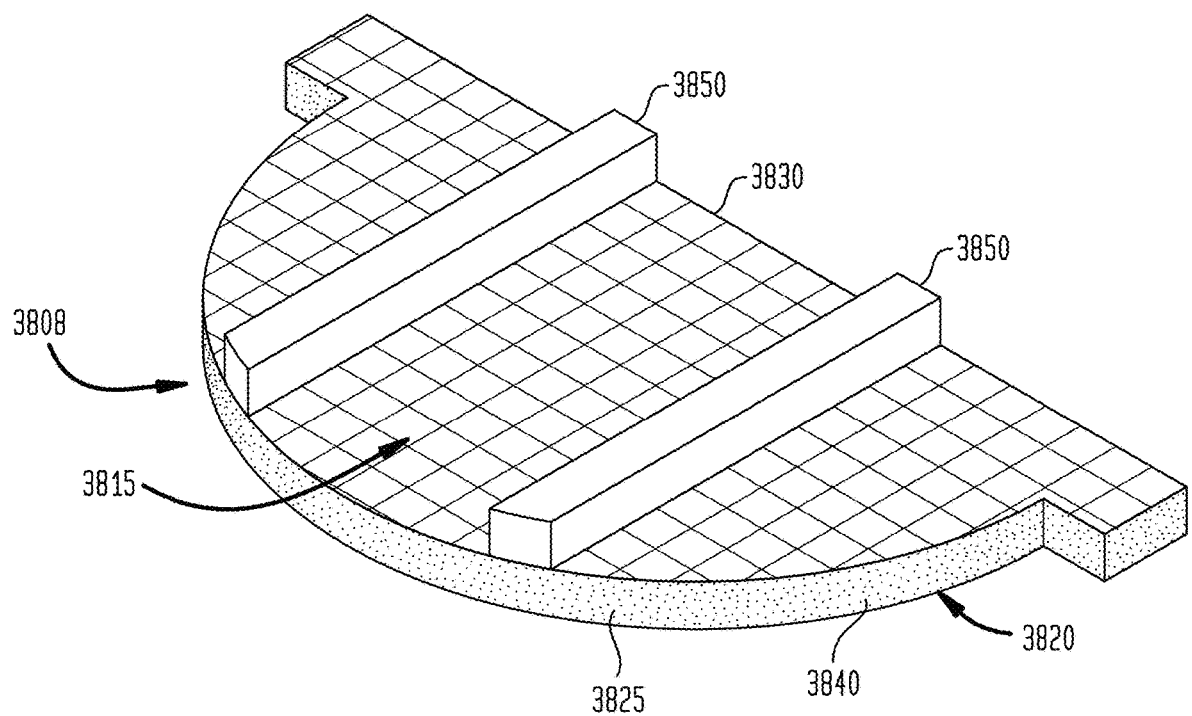
FIG. 38 is a schematic perspective view of a leaflet formed from another partially coated fabric forming ribs according to the present disclosure.

FIG. 38 illustrates another embodiment of a leaflet 3808 generally as described in FIGS. 28-37. Leaflet 3808 contains a fabric layer 3840 similar to the fabric layers previously described. Disposed on the downstream surface 3815 of the leaflet are one or more "ribs" or reinforcing strips 3850 composed of a partial polymer layer. These ribs are shown as running from approximately the attachment edge 3825 to the free edge 3830 of leaflet 3808. Reinforcing ribs 3850 may provide weight and structure to bias the leaflet from an open position back to a closed position. They may also provide some measure of structural rigidity and reinforcement to leaflet 3808. While shown as extending from the attachment edge 3825 of the leaflet to the free edge 3830, that may not be the case. They may extend from attachment edge 3825 approximately halfway along the downstream surface 3815 of the leaflet toward the free edge 3830. Similarly, they may extend from adjacent free edge 3830 approximately 30% of the way along the downstream surface of fabric layer 3840 toward the attachment edge 3825. Ribs 3850 may be of any length, thickness, width, number of polymer layers and composition.

While ribs 3850 are shown applied to the downstream surface 3815 of fabric layer 3840, they could be applied to the upstream surface 3820 thereof instead of, or in addition to, their application to the downstream surface. Moreover, the entire downstream surface of the leaflet in FIG. 38 may be coated with an additional polymer layer (not shown) to provide a smooth, if undulating, surface topography. A similar polymer layer could be provided on the upstream surface of the leaflet if ribs 3850 were applied to upstream surface 3820.

Figure 39:
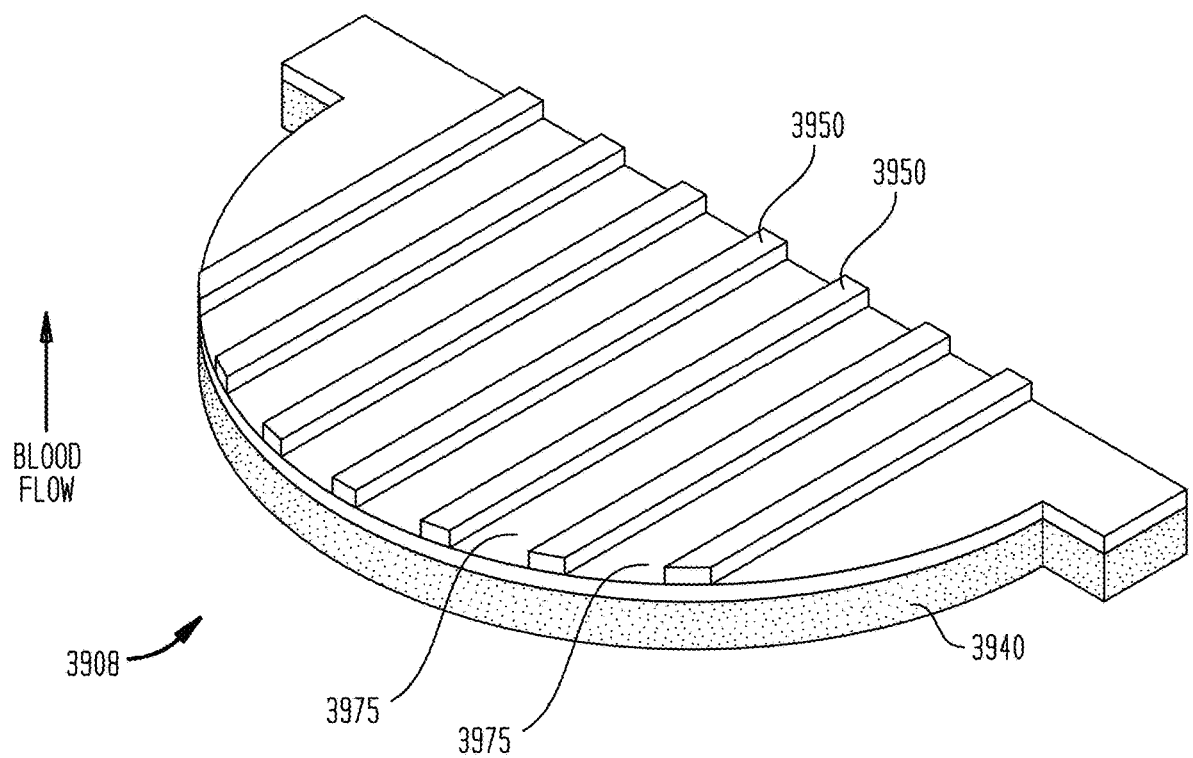
FIG. 39 is a schematic perspective view of a leaflet formed from another partially coated fabric forming ribs according to the present disclosure.

This concept of reinforcing ribs is further illustrated in FIG. 39 in which leaflet 3908 contains a plurality of ribs 3950 again extending from adjacent the attachment edge to the free edge of fabric layer 3940. In addition to providing reinforcement, shape and biasing as previously described in connection with the leaflet in FIG. 38, the spaces 3975 between ribs 3950 may act as folding regions helping to provide a controlled fold of the leaflet when the prosthetic heart valve is collapsed for loading into a catheter for transcatheter or transapical delivery. In a variant hereof, leaflet 3908, or any leaflet described herein, whether coated or uncoated, may be scored on its upstream surface or downstream surface, such as with a laser, to produce a pattern on the surface. Such pattern may facilitate folding of the leaflet during collapsing of the prosthetic heart valve, may increase the flexibility of the leaflet for opening and closing during use, or may improve the performance of the leaflet in other ways.

Figure 40:
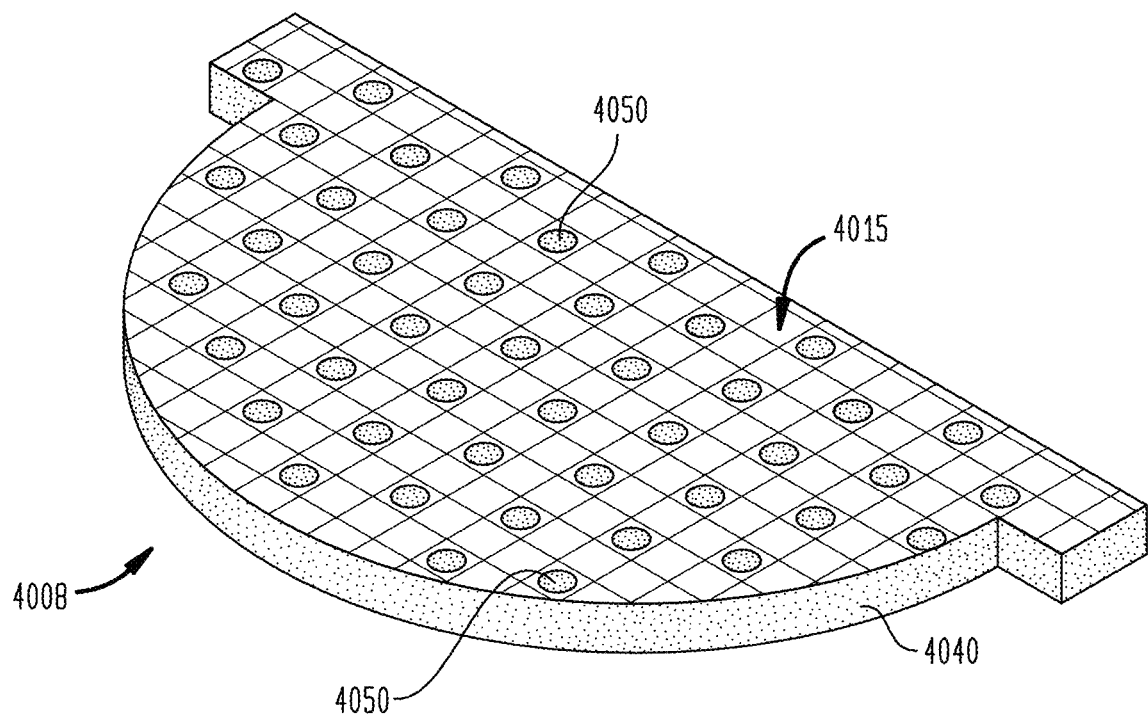
FIG. 40 is a schematic perspective view of a leaflet formed from another partially coated fabric forming spots according to the present disclosure.

FIG. 40 illustrates another leaflet embodiment. Here, leaflet 4008 comprises a fabric layer 4040 having a downstream surface 4015 to which are attached one or more polymer dots or spots 4050. Like the polymer ribs illustrated in FIGS. 38 and 39, the spots 4050 may provide weight to help bias the leaflet to a closed position in operation. Spots 4050 may also provide selective reinforcement and/or abrasion resistance. While shown as spots or dots in FIG. 40, these spots could be present in any number and in any shape such as, without limitation, crosses, lines, dashes, polygons, etc.

Figure 41:
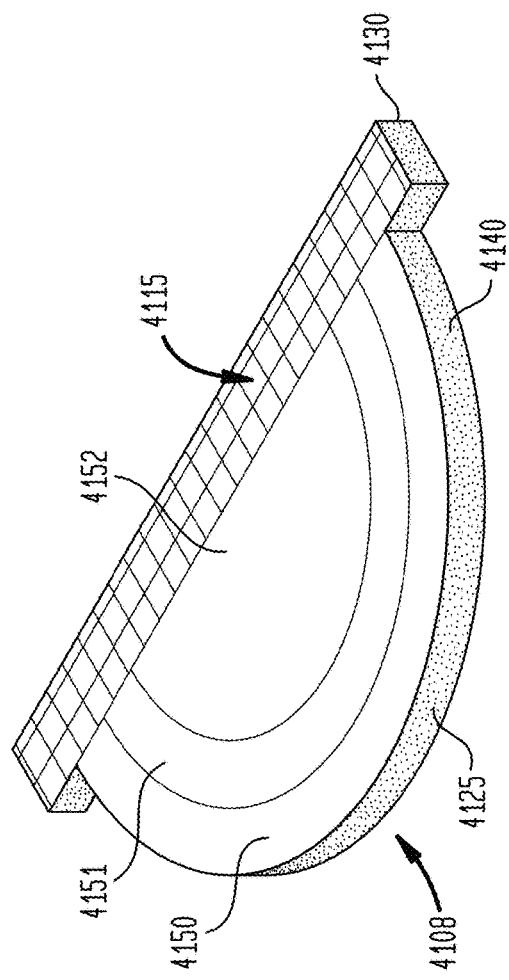
FIG. 41 is a schematic perspective view of a leaflet formed from another coated fabric according to the present disclosure.
Figure 41B:
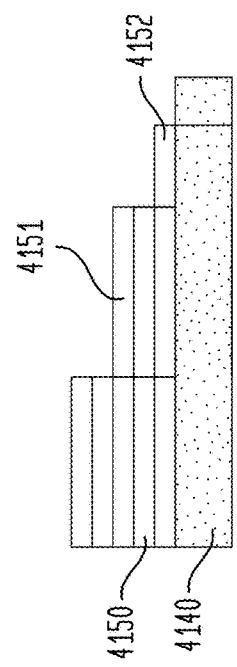
FIG. 41B is a cross-sectional view of a further variant of the leaflet of FIG. 41.
Figure 41A:
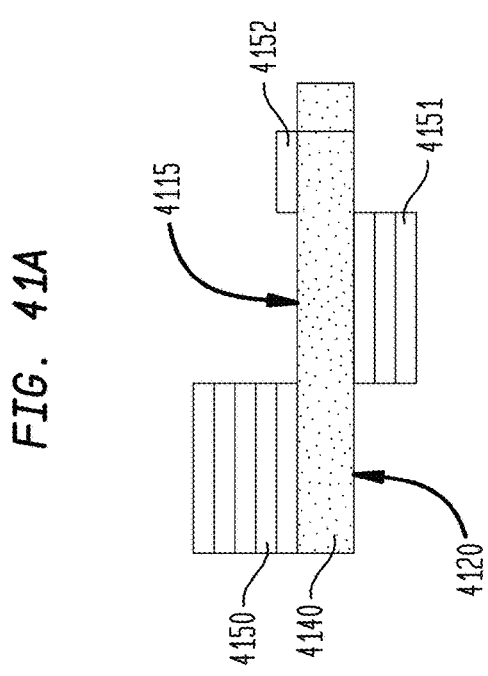
FIG. 41A is a cross-sectional view of a variant of the leaflet of FIG. 41.

FIGS. 41, 41A, and 41B illustrate other partial coating arrangements for a leaflet. In FIG. 41, partial polymer coatings are disposed on the downstream surface 4115 of the fabric layer 4140 of leaflet 4108. A first semicircular polymer coating area 4150 of a predetermined width may be comprised of five individual polymer layers, which may be the same or different in composition and thickness. Disposed relatively inwardly toward the free edge 4130 of leaflet 4108 is a second concentric semicircular partial coated area 4151 comprised of three different polymer layers. These layers may have the same composition and thickness or a different composition and/or thickness from those used in partial coated area 4150. They may have the same or a different width as well. Finally, further inwardly and closer free edge 4130 is partial coated area 4152 composed of a single polymer layer. Partial coated area 4152 may be made of one of the polymers used in partial coated areas 4150 or 4151 or may be made of a different material altogether. It may have a width that is the same as or different from areas 4150 and 4151. The area directly adjacent free edge 4130 in this embodiment is uncoated. This entire structure could be coated with an additional continuous layer that would provide a smoother surface, albeit one gradually getting thinner from the attached edge 4125 to free edge 4130.

FIG. 41A shows a similar construction, however, coating area 4151 is disposed on the upstream surface 4120 of the leaflet as opposed to the downstream surface 4115. Partial coated area 4150 composed of five individual polymer layers and partial coated area 4152 composed of a single polymer layer are disposed on the downstream surface 4115.

FIG. 41B shows a similar construction, however, instead of being semicircular or forming a rainbow, the coated areas are formed in parallel strips, with the first strip 4150 running roughly parallel to the free edge 4130 composed of five individual polymer layers, the next strip 4151 composed of three layers and the last area 4152 composed of a single layer.

Figure 42:
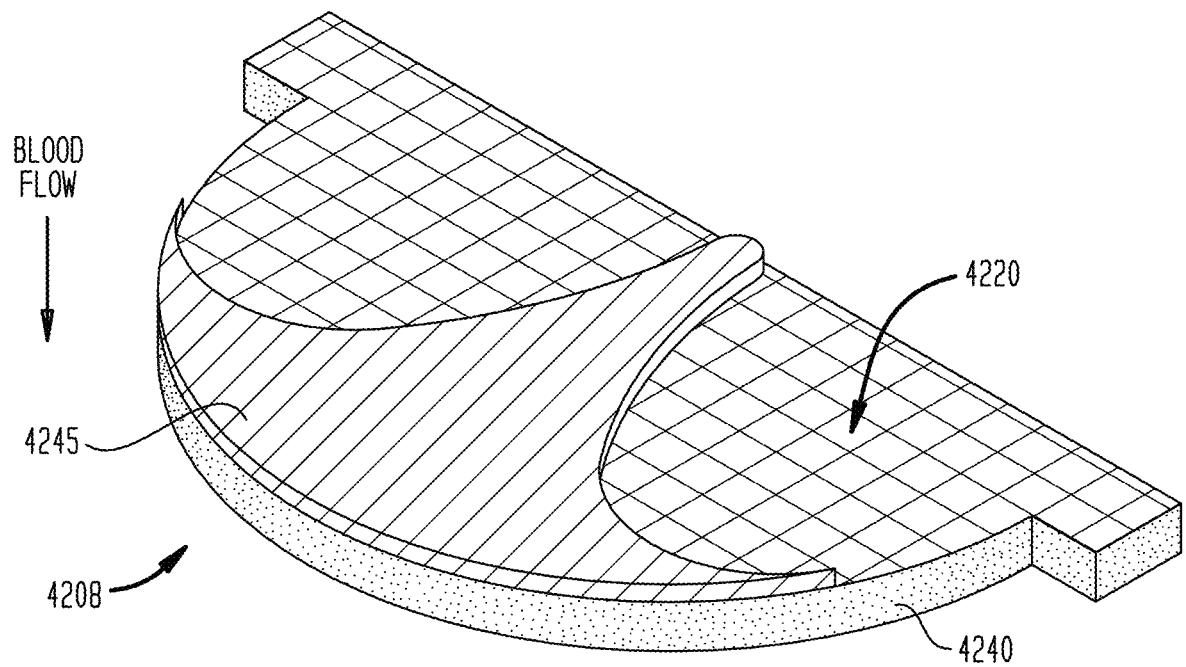
FIG. 42 is a schematic perspective view of a leaflet formed from another partially coated fabric according to the present disclosure.

FIG. 42 illustrates a partial coating on a fabric leaflet 4208 disposed on the upstream side of the leaflet. In particular, leaflet 4208 is shown comprising a fabric layer 4240 and applied to its upstream surface 4220 is a reinforcing partial polymer coating 4245. This structure is made of a partial coating of at least one polymer layer, and possibly a plurality of polymer layers, in any shape or size as described in FIGS. 28-41.

Figure 43:
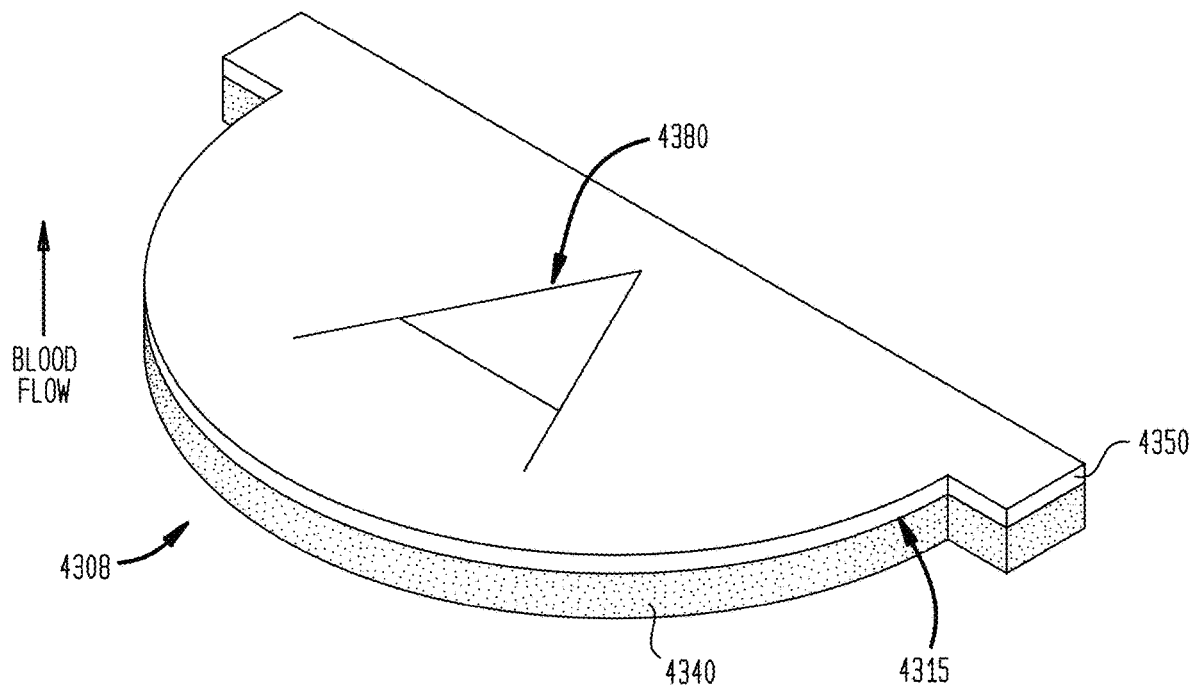
FIG. 43 is a schematic perspective view of a leaflet formed from another coated fabric incorporating indicia according to the present disclosure.
Figure 43A:
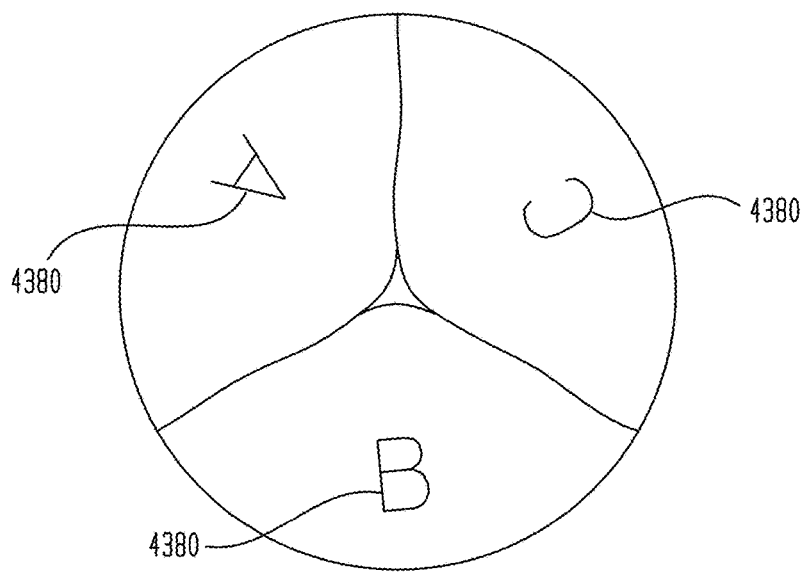
FIG. 43A is a highly schematic transverse cross-section of a prosthetic heart valve incorporating a plurality of the leaflets of FIG. 43.

The leaflet 4308 in FIGS. 43 and 43A is similar in structure to a leaflet described in connection with FIG. 29, except that the polymer layer 4350 is disposed on the downstream surface 4315 of fabric layer 4340. Leaflet 4308, however, contains one or more indicia 4380 that may be apparent visually to the naked eye, may be radiopaque to make it visible during surgery when the device is implanted within a patient's anatomy, or both. Indicia 4380 may help a surgeon position and orient the valve as needed and may assist in visualizing the movement of the leaflet to show an operable valve. Letters are used as the indicia 4380 in FIG. 43, but numbers, Roman numerals, symbols, or any other relevant indicia may be used as well. FIG. 43A is a view of a coapted set of leaflets such as shown in FIG. 3. It illustrates the use of a plurality of indicia 4380 individually on each leaflet 4308. The indicia may be embedded within polymer layer 4350, may be sandwiched between adjacent polymer layers, or may be disposed between polymer layer 4350 and fabric layer 4340.

FIGS. 44, 44A, 44B, and 44C illustrate an embodiment similar to that shown in FIG. 43. Leaflet 4408, however, is an uncoated fabric composed entirely of fabric layer 4440. Woven into that fabric, melted or otherwise embedded into the fabric, or glued or otherwise applied to a surface of the fabric may be visual and/or radiopaque indicia 4480. FIG. 44A shows an embodiment like that shown in FIG. 43A, in which indicia 4480 constitute a plurality of letters. FIG. 44B shows indicia 4480 as Roman numerals, and FIG. 44C shows the indicia as a series of dots.

Figure 45:
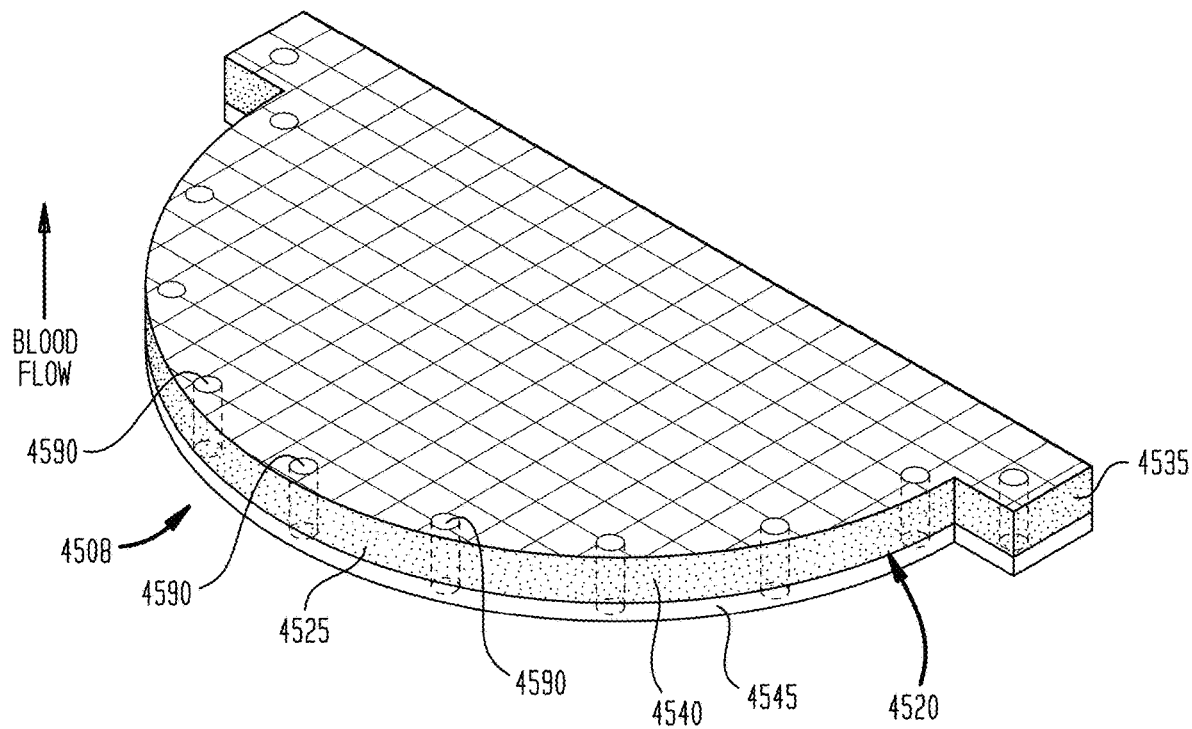
FIG. 45 is a schematic perspective view of a leaflet formed from another partially coated fabric incorporating holes according to the present disclosure.
Figure 45A:
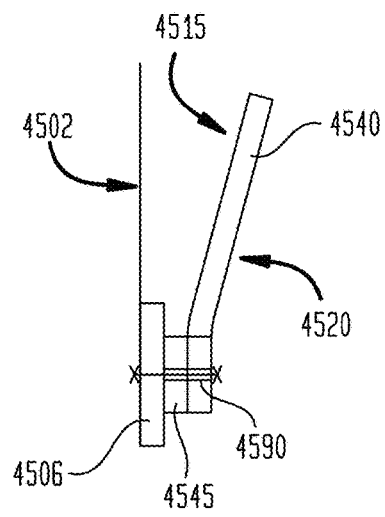
FIG. 45A is a schematic partial cross-section of a stent and a valve assembly including a cuff and the leaflet of FIG. 45.
Figure 45B:
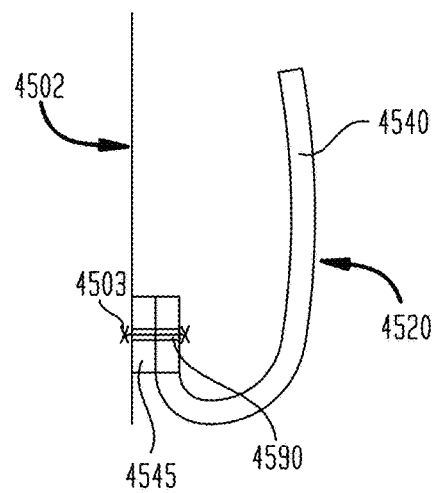
FIG. 45B is a schematic partial cross-section of a stent and a valve assembly incorporating the leaflet of FIG. 45.

FIGS. 45, 45A and 45B illustrate a leaflet as previously described in connection with FIG. 35. Leaflet 4508 includes a fabric layer 4540 and attached to its upstream surface 4520 adjacent attachment edge 4525 is a polymer layer 4545, which partially coats the upstream surface 4520 of the fabric layer. Additionally, leaflet 4508 includes a number of holes 4590 disposed adjacent attachment edge 4525 and through both fabric layer 4540 and partial polymer layer 4545. These holes 4590 may facilitate suturing, lacing or other attachment of leaflet 4508 to the support structure. Holes 4590 may also be formed in the leaflet tabs 4535 to facilitate the attachment or lacing of the leaflet commissures to one another by aligning the holes in adjacent leaflet tabs, as well as the attachment of the leaflets to the stent. Holes 4590 may be formed by laser drilling, a process that locally melts the polymer fabric and polymer layer forming a smooth, tough, abrasion resistant surface, much like a grommet, that can provide resistance to damage caused by the passage of sutures therethrough during the suturing process. These holes or grommets 4590 may be coated with a more lubricous coating or polymer material that is permanent or one that can be removed to further improve the suturing process and prevent damage to the leaflet. Moreover, the laser drilling process may melt the various layers together in a localized area, which could help prevent fraying or damage. While laser drilled holes have been described, the holes may be produced by any other means as well, such as molding, mechanical or water jet drilling, and the like.

FIG. 45A shows a partial cross-sectional view of a stent with an attached valve assembly as previously described. In this view, stent 4502 has a cuff 4506 attached to its luminal surface. Leaflet 4508 composed of fabric layer 4540 contains a partial polymer layer 4545 on its downstream surface 4515, which is disposed between the cuff and the fabric layer 4540. Leaflet 4508 contains grommets 4590 through which the leaflet is sutured or laced to cuff 4506, stent 4502, or both. Grommets may also be formed in a pattern in cuff 4506 to facilitate the attachment of the cuff to the stent. FIG. 45B shows a similar arrangement in which the device contains no cuff and a partial polymer layer 4545 is disposed on the upstream side 4520 of leaflet 4508, as illustrated in FIG. 45. Grommets 4590 are provided through both fabric layer 4540 and partial polymer layer 4545, enabling the leaflet to be sutured or laced via suture 4503 to the stent 4502. Grommets have been described here in connection with partially coated leaflets. However, these grommets could be formed in fully coated or completely uncoated leaflets, in coated or uncoated cuffs, and in any portion of a medical device that may be attached to a support structure by a suture.

Figure 46:
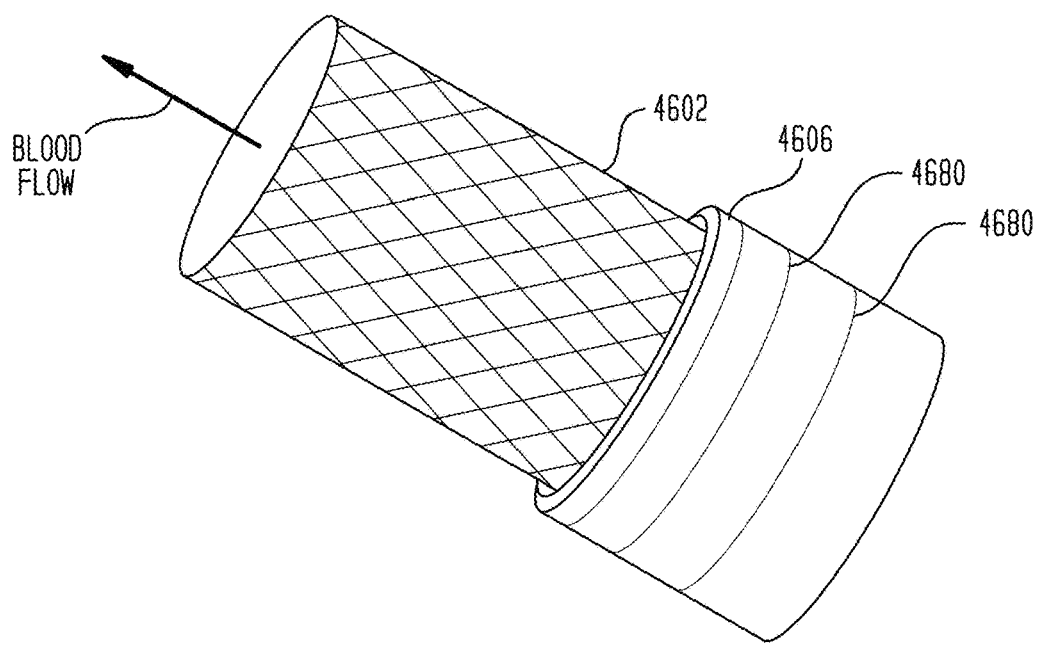
FIG. 46 is a schematic perspective view of a stent having a cuff formed from a coated fabric incorporating radiographic bands according to the present disclosure.
Figure 46A:
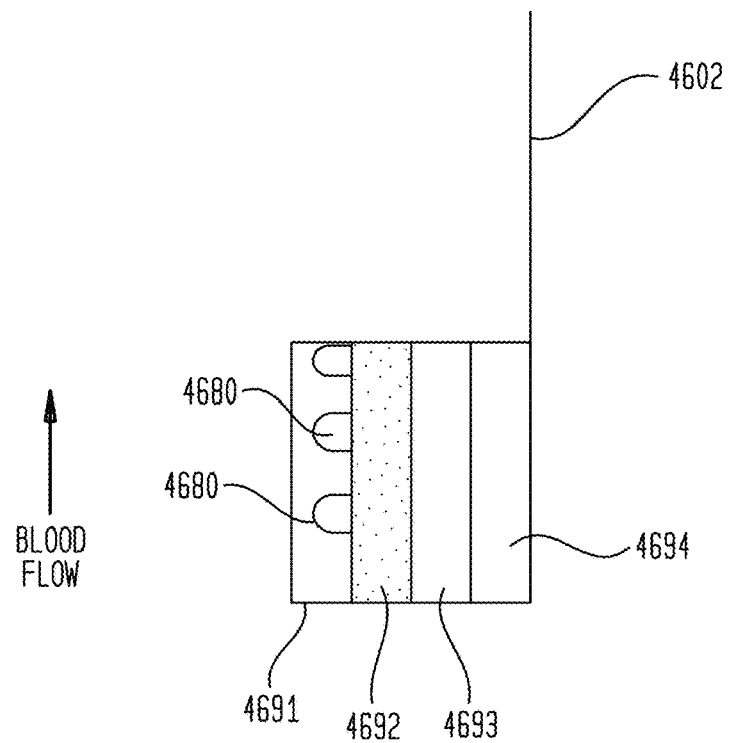
FIG. 46A is a schematic partial cross-section of the stent and cuff of FIG. 46.

FIG. 46 illustrates a stent 4602 containing a cuff 4606 on its abluminal or exterior surface. Cuff 4606 contains a plurality of indicia, in this case, radiopaque bands 4680 disposed at various intervals to assist the surgeon in placement of the prosthetic valve. The structure of cuff 4606 is illustrated in more detail in FIG. 46A. Attached to the exterior of stent 4602, and provided for illustrative purposes only, cuff 4606 has four layers. The outermost layer 4691 is a polymer layer covering the entire exterior surface of cuff 4606. The next innermost layer is a fabric layer 4692. Disposed between the fabric layer 4692 and outermost polymer layer 4691 are the circumferential radiopaque and/or visual indicia 4680. Between the fabric layer 4692 and stent 4602 are two additional polymer layers 4693 and 4694. Each of layers 4691, 4693 and 4694 may be composed of the same or different polymer materials or may have the same or different dimensions and thicknesses as previously described in connection with the leaflets described in FIGS. 28-45.

The uses of partial coatings or patterned full coatings to provide abrasion resistance to the free edge of leaflets, to help facilitate the attachment of the leaflets to a supporting structure by reinforcing and preventing the unraveling of attachment edges, to provide reinforcing structures, folding zones, etc., and to provide indicia, have been described mainly in terms of leaflets and, to a lesser extent, cuffs designed for use in collapsible/expandable valves. However, some of the described structures, such as grommets and indicia, may be incorporated in both coated and uncoated fabrics for use in other collapsible/expandable valves. They may all be used as well in constructing leaflets and cuffs or other structures for surgical valves—those sewn in place using open heart surgery. And they may be used in other medical devices as described herein.

One coated fabric which may be useful for some applications is composed of five layers, two polymer layers (each about 20 μm thick) laminated to one side of a woven fabric and two other polymer layers (each about 20 μm thick) laminated to the other side of the same fabric. These polymer layers may be, for example, made of Dyneema Purity® membrane 55501 available from DSM Biomedical (www.dsmbiomedical.com). Dyneema Purity® membrane 55501 is composed of UHMWPE and is said to be known for uses in the medical device industry. The properties of Dyneema Purity® membrane 55501 are specified in its Product Data Sheet from DSM Biomedical dated June 2015. Other materials, a greater or lesser number of layers, layers of variable thicknesses, and different woven fabrics may be used instead. For example, Dyneema Purity® TG dtex10 TS450 may be an example of a suitable fiber for use in producing the fabrics disclosed herein, including for cuffs and/or leaflets of a prosthetic heart valve. The properties of Dyneema Purity® TG dtex10 TS450 are specified in its Product Data Sheet from DSM Biomedical dated Sep. 2013. That fabric may be used in uncoated form, or may include Dyneema Purity® membrane 55501 as one or more polymer coating layers.

After the desired fabric material has been created and shaped or cut, it will typically need to be connected to a supporting structure (such as a stent if the material is intended for use as a cuff and/or prosthetic leaflets). The attachment may be accomplished through any one of a number of suitable methods, including suturing, heat bonding, weaving or knitting directly to the supporting structure, gluing, wrapping, electrospinning, laminating, mechanical attachment such as hooks, hook-and-loop fasteners, being sandwiched between two supporting structures, or being bonded directly to the supporting structure, such as integrating the fabric to the supporting structure while the supporting structure is in a non-set state (e.g., a liquid) in which curing the supporting structure results in the fabric being integrated into the supporting structure.

In attaching fabric-based components to a stent and/or to another support structure of a medical device, the fabric may be attached such that the fibers are oriented in a particular direction. This consideration applies both to uncoated fabrics, as well as coated fabrics described below. Most woven fabrics are produced using fibers that are woven at right angles to each other. These fabrics may be cut and attached to the support structure such that the direction of at least one of the fibers in the weave is substantially parallel to the longitudinal axis of the support structure, and another fiber is oriented generally perpendicular to the longitudinal axis of the support structure. Alternatively, these fabrics may be mounted to the support structure such that the fibers are generally oriented on a bias, i.e., at an oblique angle, relative to the longitudinal axis of the support structure. The fabrics may, for example, be used to form an inner cuff and/or an outer cuff of a collapsible/expandable heart valve or the skirt or other fabric covering of a surgical heart valve. When used for an inner cuff or an outer cuff of a collapsible/expandable heart valve, the oblique angle may be between about 30 degrees and about 60 degrees relative to the longitudinal axis of the support structure when the heart valve is in an expanded use condition. In some embodiments, the fabric may be oriented such that the fibers are oriented at about 45 degrees relative to the longitudinal axis of the support structure when the heart valve is in an expanded use condition. (See EP 2,949,292, the disclosure of which is hereby incorporated by reference herein for its teaching of the manufacture and attachment of a woven fabric at an oblique angle relative to the longitudinal axis of a stent.)

One aspect of the disclosure is a collapsible/expandable heart valve which may be implanted through a catheter or trocar, the heart valve including a valve assembly comprising a coated or uncoated fabric as described herein, and in particular, a heart valve in which the coated or uncoated fabric is used to form the leaflets and/or cuffs shown in FIGS. 28-46A. In one such embodiment, the outer cuff may be made of a coated or uncoated fabric of the disclosure. In another such embodiment, the inner cuff may be made of a coated or uncoated fabric of the disclosure. In still another such embodiment, both the inner and outer cuffs may be made of a coated or uncoated fabric of the disclosure. In still a further embodiment, the inner cuff may be coated while the outer cuff is not. In another embodiment, the inner cuff may be uncoated and the outer cuff may be coated.

In another embodiment, at least one leaflet may be made from a coated or uncoated fabric material in accordance with the disclosure. In another embodiment, some, but not all of the leaflets may be made from a coated or uncoated fabric material in accordance with the disclosure. It is also contemplated that all leaflets may be produced from a coated or uncoated fabric material in accordance with the disclosure. In one desirable embodiment, all of the leaflets may be made of the same uncoated fabric of the disclosure. In another embodiment, all of the leaflets may be made of the same coated fabric of the disclosure.

It is also an embodiment of this aspect of the disclosure that at least one cuff and at least one leaflet of the valve assembly may be composed of a coated or uncoated fabric of the disclosure. In one further embodiment, both the at least one cuff and the at least one leaflet of the valve assembly may be made of a coated fabric in accordance with the disclosure. In another embodiment, both the cuff and the leaflet may be made from an uncoated fabric in accordance with the present disclosure.

While the disclosure above provides for the use of uncoated and/or coated fabrics for prosthetic leaflets, inner cuffs, and/or outer cuffs of collapsible/expandable and surgical prosthetic cardiac valves, the concepts may be similarly or identically applied to other prosthetic valves, such as prosthetic venous valves. Prosthetic venous valves may have generally similar structures and components as those described for the prosthetic heart valves, including a stent, one or more prosthetic leaflets, and optionally inner and/or outer cuffs. If the stent is self-expandable or balloon expandable, the stent may maintain a desired position within the vasculature via a friction fit. If the stent is non-collapsible, it may be sutured or otherwise fixed at the desired position within the vasculature. The one or more prosthetic leaflets may be coupled to the stent and/or to an inner and/or outer cuff attached to the stent, for example via sutures. The prosthetic leaflets may allow blood to flow in substantially only one direction within the vasculature. The inner and/or outer cuffs may assist in enhancing sealing to help prevent blood from flowing in the retrograde direction past the prosthesis, and may also aid in coupling the one or more prosthetic leaflets to the stent. The prosthetic leaflets, inner cuffs, and outer cuffs of the prosthetic venous valves may be formed of any of the materials described above for similar components of the prosthetic cardiac valves, for example including the uncoated and/or coated fabrics described herein.

The uncoated and/or coated fabrics described herein may have still further applications, for example with occluders, which may also be referred to as closure devices. Such occluders may be used to treat any suitable abnormality or condition, including patent foramen ovale ("PFO"), atrial septal defect ("ASD"), ventricular septal defect ("VSD"), patent ductus arteriosus ("PDA"), and left atrial appendage ("LAA") closure. Occluders may have various different configurations depending on factors such as the type of abnormality to be occluded, the location of the target site, the condition of the patient's vasculature or cardiac anatomy, and the practitioner's preferences. The occluders described herein have a collapsed condition and an expanded condition. For example, in the embodiment shown in FIG. 27A, a closure device 2000 has a first expanded volume portion 2010 and a second expanded volume portion 2020 that are substantially perpendicular to a central axis extending along closure device 2000. The first expanded volume portion 2010 may be proximate a first end of closure device 2000, with the second expanded volume portion 2020 spaced axially from the first expanded volume portion 2010 and proximate a second end of closure device 2000. The first expanded volume portion 2010 may be connected to the second expanded volume portion 2020 via an axial portion 2030.

Figure 27A:
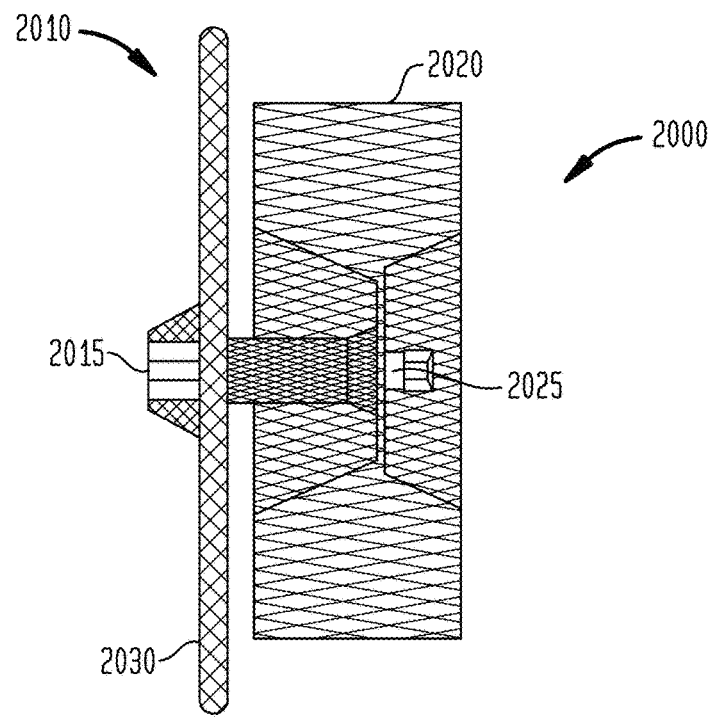
FIG. 27A is a longitudinal cross-section of a medical closure device according to an embodiment of the disclosure.

As depicted in FIG. 27A, the first expanded volume portion 2010 in the expanded condition may have the shape of a thin disk, and is intended to help maintain the closure device 2000 in position at the target site, as described in greater detail below. The second expanded volume portion 2020 in the expanded condition may, in some cases, be a generally cylindrical body that is substantially thicker in the axial direction than the first expanded volume portion 2010 and axially disposed toward the second end. The second expanded volume portion 2020 when expanded may be sized to be somewhat larger in diameter (e.g., about 10-30% larger) than the inside diameter of the vessel, cavity, or lumen to be occluded to facilitate anchoring of the device to prevent dislodgement, but not so large when collapsed as to not fit in the vessel, cavity or lumen.

At the same time, in the expanded condition, the first expanded volume portion 2010 of the closure device 2000 may have a diameter that is larger than the diameter of the second expanded volume portion 2020. This larger diameter is intended to abut the wall surrounding the abnormal aperture to prevent device movement further into the aperture and to assist in sealing the aperture. For example, the first expanded volume portion 2010 may be oversized so as to overlie the ostium or opening of the LAA in a position adjacent to, and in flush contact with, the wall of the atrium.

The first expanded volume portion 2010 may also be flexible so as to be capable of conforming to the curvature of the wall of the atrium in LAA applications or other cardiac or vascular structures in other applications. Although one configuration of the first and second expanded volume portions 2010, 2020 is described above and shown in the figures, various other configurations and sizes may be used depending on the particular application or condition to be treated. For example, one or both expanded volume portions 2010, 2020 may be thin disks or disks having a convex distal end, or the device may include a smaller diameter cylindrical portion between two larger diameter disks. Moreover, the depth or thickness of the first and/or second expanded volume portions may depend on the thickness and number of layers used to make the closure device 2000.

The first expanded volume portion 2010, the second expanded volume portion 2020, and the axial portion 2030 may each be formed of a shape-memory alloy, such as braided nitinol, to facilitate collapsing the closure device 2000 for minimally invasive delivery, and to facilitate expansion to a pre-set shape upon delivery of the closure device 2000 to the intended location. A first coupling 2015 may be disposed adjacent the first expanded volume portion 2010 and may enable connection of a delivery device or other device to closure device 2000. For example, first coupling 2015 may include internal or external threads that mate with corresponding threads of another device. A second coupling 2025, similar to the first coupling 2015, may be disposed adjacent to or within the second expanded volume portion 2020. Second coupling 2025 may also include internal or external threads for connection to corresponding threads of another device. It should be understood that other coupling mechanisms, such as press-fit or snap-fit arrangements, may be utilized in first and second couplings 2015, 2025. Additional details of closure device 2000 and similar devices are described in U.S. Pat. No. 8,758,389, the disclosure of which is hereby incorporated by reference herein.

Figure 27B:
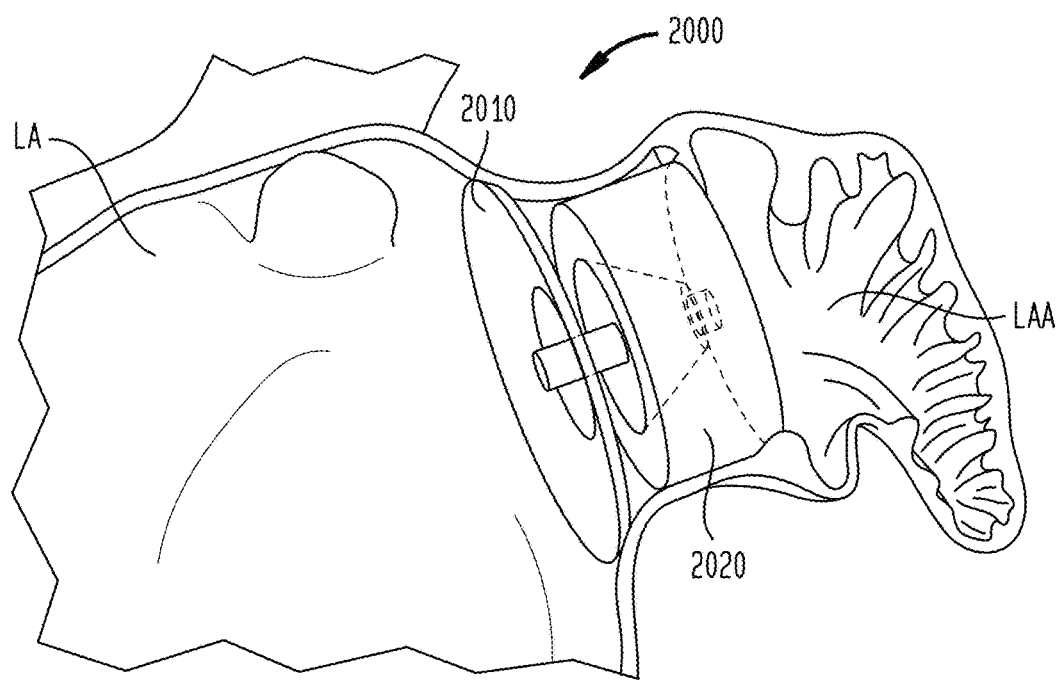
FIG. 27B is a highly schematic view of the medical closure device of FIG. 27A implanted into a left atrial appendage.

FIG. 27B is a schematic view of closure device 2000 positioned within the LAA of a left atrium LA. In patients with certain conditions, such as atrial fibrillation, blood clots may tend to form in the LAA. Implanting a device such as closure device 2000 may lead to partial or complete occlusion of the LAA, thus reducing the risk of thrombi breaking off the LAA and entering the blood stream. In order to help better occlude the LAA, it may be desirable to include fabrics on the interior surface, exterior surface, or both surfaces of the closure device 2000. For example, part or all of the outer surface, and/or part or all of the inner surface, of closure device 2000 may include one or more layers of the uncoated and/or coated fabrics described herein. Such fabrics may help better and/or more quickly occlude the LAA. In some embodiments, if portions of closure device 2000 are formed of two or more layers of braided metal, such as braided nitinol, uncoated and/or coated fabrics of the present disclosure may be included between the two or more layers of braided metal. Other closure devices, such as PFO closure devices, may similarly include uncoated and/or coated fabrics of the present disclosure on part or all of an exterior surface and/or on part or all of an interior surface (and/or between multiple layers of braided mesh if present), for similar purposes as described in connection with closure device 2000.

The uncoated and/or coated fabrics described herein may also be used to form the entirety, or portions, of various types of prosthetic vascular conduits. For example, a prosthetic aortic graft may be implanted into the aorta to treat a weakened portion of the aorta resulting from a thoracic aneurysm. Prosthetic vascular conduits may be used to perform a bypass to reroute the path of blood flow, for example as a lower extremity bypass, a cardiac bypass in conjunction with open heart surgery, or to serve as an access point to the circulatory system, such as for hemodialysis. Prosthetic vascular conduits may also be used as arteriovenous ("AV") shunts. AV fistulas are abnormal connections between an artery and vein, although they may be surgically created in order to assist with hemodialysis treatment. When an AV fistula is surgically created, an AV shunt formed from the uncoated and/or coated fabrics described herein may be implanted to provide the desired connection between the artery and vein. Prosthetic vascular conduits are typically cylindrical in shape and have been formed of PTFE or Dacron. However, prosthetic vascular grafts may instead be formed of the uncoated and/or coated fabrics described herein.

In addition to the above uses, the fabrics described herein may have additional uses. For example, hernias occur when there is an opening or a weakness in the muscle and/or connective tissue through which organs begin to push. Hernias are frequently treated with a fabric mesh that provides closure and support of the weakness and/or opening that forms the hernia. The mesh acts to patch the hernia, and is frequently formed of a plastic material. Such patches may instead be formed of the uncoated or coated fabrics disclosed herein, whether the patches are continuous or formed as a mesh. And while hernia repair is one exemplary use of patches formed of the uncoated or coated fabrics disclosed herein, such patches may be used in any other suitable procedure, including skin patches, vaginal patches, and/or cardiac patches to provide the desired support to the underlying anatomy.

In some embodiments, the fabrics described herein may be used to form adhesion barriers. Adhesion barriers are medical implants that may be used to reduce abnormal internal scarring following surgery. The uncoated or coated fabrics of the adhesion barriers may act to separate internal tissues and/or organs while they heal post-surgery.

While the above-described embodiments of devices that incorporate the uncoated or coated fabrics described herein are generally directed to devices intended to be permanently implanted into the body, the fabrics may be used for various types of medical devices that are used in medical procedures, but not intended to be implanted at all, or not intended to be implanted for longer than the surgical procedure. One such example is an embolic protection device. Generally, an embolic protection device may be used to prevent emboli that are dislodged during a medical procedure from entering the vasculature. Typically, embolic protection devices either capture dislodged emboli so that the emboli can be removed from the body, or otherwise deflect emboli from entering high-risk vasculature (such as the carotid arteries) so that the emboli are able to pass through the vasculature where there may be a lower risk of complications from the emboli. Embolic protection devices may include various types of filters that allow blood to pass through the filter, but are formed as meshes or with pore sizes small enough to trap emboli therein, or otherwise to deflect emboli. Such embolic protection devices may be formed of the fabrics described herein. Examples of embolic protection devices are disclosed in greater detail in U.S. Patent Pub. Nos. 2014/0249567 and 2018/0116780, the disclosures of which are hereby incorporated by reference herein. While the fabrics described herein may be used with short-term filters such as those described immediately above, they may also be used in permanently implanted filters, such as inferior vena cava ("IVC") filters, whether or not the IVC filter is intended to be retrievable. IVC filters typically have a central base and a plurality of legs that extend outwardly from the base to form an overall conical shape, with the legs intended to make contact with the interior surface of the lumen of the IVC to help support the IVC filter in place. The IVC filter functions by allowing blood to flow around the filter, while trapping emboli that pass into the filter, preventing the emboli from causing blockages in the vasculature downstream of the IVC filter. The IVC filters may be formed of a metal or other biocompatible material and the uncoated and coated fabrics described herein may encapsulate portions or all of the IVC filter, or in other embodiments the IVC filter may be formed entirely of the coated fabrics described herein. It should be understood that for IVC filters, or any other application disclosed herein, specific parameters of the disclosed fabrics, such as dimensions, as well as fabrication methods, may be altered to suit the particular application.

According to an aspect of the disclosure, a prosthetic heart valve comprises:

an expandable stent extending in a longitudinal direction between an inflow end and an outflow end;

a cuff coupled to a luminal surface of the stent; and a plurality of prosthetic leaflets coupled to at least one of the cuff and the stent and having an open condition and a closed condition, the plurality of prosthetic leaflets adapted to allow blood to flow from the inflow end toward the outflow end when in the open condition and to retard blood from flowing from the outflow end toward the inflow end when in the closed condition, each of the plurality of leaflets being formed of a fabric;

wherein the fabric has a first group of fibers extending in a first direction of the fabric and a second group of fibers extending in a second direction of the fabric different than the first direction, the first group of fibers and the second group of fibers being interlaced in an ordered arrangement, the first group of fibers and the second group of fibers both being composed of ultra-high molecular weight polyethylene (UHMWPE), at least one layer of the fabric having a thread count of between about 300 and about 500 fibers by between about 100 and about 300 fibers per square inch, the fabric having a thickness of between about 50 μm and about 100 μm; and/or the fabric is a woven fabric; and/or each of the plurality of prosthetic leaflets includes a free edge adapted to move as the plurality of prosthetic leaflets transitions between the open condition and the closed condition, and an attachment edge directly attached to at least one of the cuff and the stent; and/or when each of the plurality of leaflets is in a flattened condition, the first group of fibers extend in the first direction at an angle of between about 30 degrees and about 60 degrees relative to a line that extends perpendicular to the free edge; and/or the fabric is not coated by a polymer coating; and/or the fibers of the first group of fibers are coated with a first polymer coating, and the fibers of the second group of fibers are coated with a second polymer coating; and/or the fabric has a tensile strength of between about 50 N and about 100 N; and/or the fabric having an areal density of between about 0.5 ounces/yard and about 1.0 ounces/yard$^2$; and/or each fiber in the first group of fibers is formed of a plurality of UHMWPE filaments, and each fiber in the second group of fibers is formed of a plurality of UHMWPE filaments; and/or the cuff is formed of a second fabric, the second fabric having a third group of fibers extending in a first direction of the second fabric and a fourth group of fibers extending in a second direction of the second fabric different than the first direction of the second fabric, the third group of fibers and the fourth group of fibers being interlaced in an ordered arrangement, the third group of fibers and the fourth group of fibers both being composed of UHMWPE, at least one layer of the second fabric having a thread count of between about 300 and about 500 fibers by between about 100 and about 300 fibers per square inch, the second fabric having an areal density of between about 0.5 ounces/yard$^2$ and about 1.0 ounces/yard$^2$; and/or the second fabric is a woven fabric; and/or the third group of fibers extend in the first direction of the second fabric at an angle of between about 30 degrees and about 60 degrees relative to the longitudinal axis of the stent when the stent is in an expanded condition; and/or each of the plurality of prosthetic leaflets has a first major surface opposite a second major surface, the first major surface generally facing the outflow end of the stent in the closed condition, the second major surface generally facing the inflow end of the stent in the closed condition; and/or a polymer coating on at least one of the first major surface and the second major surface; and/or the polymer coating is formed of UHMWPE; and/or the polymer coating is disposed on an entirety of at least one of the first major surface and the second major surface; and/or the polymer coating is disposed on an entirety of the first major surface and on an entirety of the second major surface; and/or each of the plurality of prosthetic leaflets includes a free edge adapted to move as the plurality of prosthetic leaflets transitions between the open condition and the closed condition, and an attachment edge directly attached to at least one of the cuff and the stent; and/or the polymer coating is disposed on the first major surface adjacent the attachment edge or on the second major surface adjacent the attachment edge; and/or the attachment edge is directly attached to the at least one of the cuff and the stent via one or more sutures extending through the polymer coating; and/or at least some portions of the first major surface are not coated by the polymer coating, and at least some portions of the second major surface are not coated by the polymer coating; and/or the polymer coating is disposed adjacent the attachment edge on the second major surface, at least some other portions of the second major surface remaining uncoated by the polymer coating, and the polymer coating is disposed adjacent the free edge on the first major surface, at least some other portions of the first major surface remaining uncoated by the polymer coating; and/or portions of the first major surface adjacent the free edge are coated by the polymer coating, at least some other portions of the first major surface remaining uncoated by the polymer coating, and portions of the second major surface adjacent the free edge are not coated by the polymer coating; and/or the second major surface is entirely uncoated by the polymer coating; and/or portions of the second major surface adjacent the free edge are coated by the polymer coating, at least some other portions of the second major surface remaining uncoated by the polymer coating, and portions of the first major surface adjacent the free edge are not coated by the polymer coating; and/or the polymer coating is disposed adjacent the free edge on the second major surface, at least some other portions of the second major surface remaining uncoated by the polymer coating, and the polymer coating is disposed adjacent the free edge on the first major surface, at least some other portions of the first major surface remaining uncoated by the polymer coating; and/or the polymer coating is disposed in a plurality of strips on the second major surface so that portions of the second major surface between adjacent ones of the plurality of strips are uncoated by the polymer coating, each of the plurality of strips extending in a direction from the attachment edge toward the free edge.

According to another aspect of the disclosure, a prosthetic heart valve comprises:

an expandable stent having a luminal surface; and a valve assembly attached to the luminal surface of the stent, the valve assembly including a cuff and a leaflet, the leaflet having a first major surface, an opposed second major surface, an attachment edge, a free edge, and a plurality of tabs, both the cuff and the leaflet composed of an uncoated woven fabric composed of a polymer, the woven fabric having a thread count of 300-500×100-300 fibers per square inch, an areal density of between 0.5 and 1.0 ounces/yd$^2$, a thickness of between about 20 and about 250 μm, and a tensile strength of between about 50 N and about 100 N; and/or the polymer is polytetrafluoroethylene ("PTFE"); and/or the polymer is low density PTFE, high density PTFE, or ultra-high molecular weight PTFE ("UHMWPTFE"); and/or the polymer is stretched PTFE or expanded PTFE; and/or the polymer is polyethylene ("PE"); and/or the polymer is low density PE, high density PE, or ultra-high molecular weight PE ("UHMWPE"); and/or the polymer is polypropylene ("PP"); and/or the polymer is low density PP, high density PP, or ultra-high molecular weight PP ("UHMWPP"); and/or the polymer is a copolymer or block polymer of PE and PP; and/or the polymer is a polyurethane, an acrylic, a polyester, a polyamide, a polyimide, a vinyl acetate, an alkyd, an epoxy, a silane, or a siloxane; and/or the woven fabric has an areal density of about 0.5 ounces/yd$^2$; and/or the woven fabric has an areal density of about 0.8 ounces/yd$^2$; and/or the woven fabric has an areal density of about 1.0 ounces/yd$^2$; and/or the woven fabric has a thickness of between about 50 and about 100 μm; and/or the woven fabric has a thickness of between about 75 μm; and/or the woven fabric has a tensile strength of about 75N; and/or the woven fabric has a thread count of 440×220 fibers per square inch; and/or at least one grommet is disposed in the attachment edge or in one of the plurality of tabs.

According to a further aspect of the disclosure; a prosthetic heart valve comprises:

an expandable stent having a luminal surface; and a valve assembly attached to the luminal surface of the stent, the valve assembly including a cuff and a leaflet, the leaflet having a first major surface, an opposed second major surface, an attachment edge, a free edge, and a plurality of tabs, both the cuff and the leaflet composed of a woven fabric composed of a first polymer, the leaflet further comprising a coating composed of a second polymer disposed on at least one of the first major surface and the second major surface; and/or the woven fabric has an areal density of between 0.5 and 1.0 ounces/yd$^2$; and/or the woven fabric has an areal density of about 0.5 ounces/yd$^2$; and/or the woven fabric has an areal density of about 0.8 ounces/yd$^2$; and/or the woven fabric has an areal density of about 1.0 ounces/yd$^2$; and/or the woven fabric, including the coating, has a thickness of between about 20 and about 250 µm; and/or the woven fabric, including the coating, has a thickness of between about 50 and about 100 µm; and/or the woven fabric, including the coating, has a thickness of between about 75 µm; and/or the woven fabric has a tensile strength of between about 50 N and about 100 N; and/or the woven fabric has a tensile strength of about 75 N; and/or the woven fabric has a thread count of 300-500×100-300 fibers per square inch; and/or the woven fabric has a thread count of 440×220 fibers per square inch; and/or the first polymer is polytetrafluoroethylene ("PTFE"); and/or the first polymer is low density PTFE, high density PTFE, or ultra-high molecular weight PTFE ("UHMWPTFE"); and/or the first polymer is stretched PTFE or expanded PTFE; and/or the first polymer is polyethylene ("PE"); and/or the first polymer is low density PE, high density PE, or ultra-high molecular weight PE ("UHMWPE"); and/or the first polymer is polypropylene ("PP"); and/or the first polymer is low density PP, high density PP, or ultra-high molecular weight PP ("UHMWPP"); and/or the first polymer is a copolymer or block polymer of PE and PP; and/or the first polymer is a polyurethane, an acrylic, a polyester, a polyamide, a polyimide, a vinyl acetate, an alkyd, an epoxy, a silane, or a siloxane; and/or the second polymer is polytetrafluoroethylene ("PTFE"); and/or the second polymer is low density PTFE, high density PTFE, or ultra-high molecular weight PTFE ("UHMWPTFE"); and/or the second polymer is stretched PTFE or expanded PTFE; and/or the second polymer is polyethylene ("PE"); and/or the second polymer is low density PE, high density PE, or ultra-high molecular weight PE ("UHMWPE"); and/or the second polymer is polypropylene ("PP"); and/or the second polymer is low density PP, high density PP, or ultra-high molecular weight PP ("UHMWPP"); and/or the second polymer is a copolymer or block polymer of PE and PP; and/or the second polymer is a polyurethane, an acrylic, a polyester, a polyamide, a polyimide, a vinyl acetate, an alkyd, an epoxy, a silane, or a siloxane; and/or the coating is composed of between 1 and 20 coating layers having a total coating thickness of between about 5 µm and about 50 µm; and/or at least one grommet is disposed in the attachment edge or in one of the plurality of tabs.

According to another aspect of the disclosure, a prosthetic heart valve comprises:

an expandable stent having a luminal surface; and a valve assembly attached to the luminal surface of the stent, the valve assembly including a cuff and a leaflet, the leaflet having a first major surface, an opposed second major surface, an attachment edge, a free edge, and a plurality of tabs, both the cuff and the leaflet composed of a woven fabric composed of a first polymer, at least one of the attachment edge, the free edge, and the plurality of tabs the leaflet further comprising a coating composed of a second polymer disposed on at least one of the attachment edge, the free edge, and the plurality of tabs; and/or the woven fabric has an areal density of between 0.5 and 1.0 ounces/yd$^2$; and/or the woven fabric has an areal density of about 0.5 ounces/yd$^2$; and/or the woven fabric has an areal density of about 0.8 ounces/yd$^2$; and/or the woven fabric has an areal density of about 1.0 ounces/yd$^2$; and/or the woven fabric, including the coating, has a thickness of between about 20 and about 250 µm; and/or the woven fabric, including the coating, has a thickness of between about 50 and about 100 µm; and/or the woven fabric, including the coating, has a thickness of between about 75 µm; and/or the woven fabric has a tensile strength of between about 50 N and about 100 N; and/or the woven fabric has a tensile strength of about 75 N; and/or the woven fabric has a thread count of 300-500×100-300 fibers per square inch; and/or the woven fabric has a thread count of 440×220 fibers per square inch; and/or the first polymer is polytetrafluoroethylene ("PTFE"); and/or the first polymer is low density PTFE, high density PTFE, or ultra-high molecular weight PTFE ("UHMWPTFE"); and/or the first polymer is stretched PTFE or expanded PTFE; and/or the first polymer is polyethylene ("PE"); and/or the first polymer is low density PE, high density PE, or ultra-high molecular weight PE ("UHMWPE"); and/or the first polymer is polypropylene ("PP"); and/or the first polymer is low density PP, high density PP, or ultra-high molecular weight PP ("UHMWPP"); and/or the first polymer is a copolymer or block polymer of PE and PP; and/or the first polymer is a polyurethane, an acrylic, a polyester, a polyamide, a polyimide, a vinyl acetate, an alkyd, an epoxy, a silane, or a siloxane; and/or the second polymer is polytetrafluoroethylene ("PTFE"); and/or the second polymer is low density PTFE, high density PTFE, or ultra-high molecular weight PTFE ("UHMWPTFE"); and/or the second polymer is stretched PTFE or expanded PTFE; and/or the second polymer is polyethylene ("PE"); and/or the second polymer is low density PE, high density PE, or ultra-high molecular weight PE ("UHMWPE"); and/or the second polymer is polypropylene ("PP"); and/or the second polymer is low density PP, high density PP, or ultra-high molecular weight PP ("UHMWPP"); and/or the second polymer is a copolymer or block polymer of PE and PP; and/or the second polymer is a polyurethane, an acrylic, a polyester, a polyamide, a polyimide, a vinyl acetate, an alkyd, an epoxy, a silane, or a siloxane; and/or the coating is composed of between 1 and 20 coating layers having a total coating thickness of between about 5 μm and about 50 μm; and/or at least one grommet is disposed in the attachment edge or in one of the plurality of tabs.

According to still another aspect of the disclosure, a prosthetic heart valve comprises:

an expandable stent having a luminal surface and an abluminal surface;

a cuff disposed on the abluminal surface of the stent; and at least two prosthetic leaflets each having a first major surface, an opposed second major surface, an attachment edge, a free edge, and a plurality of tabs, both the cuff and the at least two prosthetic leaflets being composed of a woven fabric composed of a polymer, the woven fabric having a thread count of 300-500×100-300 fibers per square inch, an areal density of between 0.5 and 1.0 ounces/yd$^2$, a thickness of between about 20 and about 250 μm, and a tensile strength of between about 50 N and about 100 N; and/or the polymer is polytetrafluoroethylene ("PTFE"); and/or the polymer is low density PTFE, high density PTFE, or ultra-high molecular weight PTFE ("UHMWPTFE"); and/or the polymer is stretched PTFE or expanded PTFE; and/or the polymer is polyethylene ("PE"); and/or the polymer is low density PE, high density PE, or ultra-high molecular weight PE ("UHMWPE"); and/or the polymer is polypropylene ("PP"); and/or the polymer is low density PP, high density PP, or ultra-high molecular weight PP ("UHMWPP"); and/or the polymer is a copolymer or block polymer of PE and PP; and/or the polymer is a polyurethane, an acrylic, a polyester, a polyamide, a polyimide, a vinyl acetate, an alkyd, an epoxy, a silane, or a siloxane; and/or the woven fabric has an areal density of about 0.5 ounces/yd$^2$; and/or the woven fabric has an areal density of about 0.8 ounces/yd$^2$; and/or the woven fabric has an areal density of about 1.0 ounces/yd$^2$; and/or the woven fabric has a thickness of between about 50 and about 100 μm; and/or the woven fabric has a thickness of between about 75 μm; and/or the woven fabric has a tensile strength of about 75N; and/or the woven fabric has a thread count of 440×220 fibers per square inch; and/or at least one grommet is disposed in the attachment edge or in one of the plurality of tabs; and/or a coating fully covers the first major surface or the second major surface of each of the at least two prosthetic leaflets, the coating composed of a second polymer; and/or a coating covering one or more of the attachment edges, free edges, and the pluralities of tabs of the at least two prosthetic leaflets, the coating composed of a second polymer; and/or the coating is disposed only upon one or more of the attachment edges, free edges, and the pluralities of tabs of the at least two prosthetic leaflets; and/or the second polymer is polytetrafluoroethylene ("PTFE"); and/or the second polymer is low density PTFE, high density PTFE, or ultra-high molecular weight PTFE ("UHMWPTFE"); and/or the second polymer is stretched PTFE or expanded PTFE; and/or the second polymer is polyethylene ("PE"); and/or the second polymer is low density PE, high density PE, or ultra-high molecular weight PE ("UHMWPE"); and/or the second polymer is polypropylene ("PP"); and/or the second polymer is low density PP, high density PP, or ultra-high molecular weight PP ("UHMWPP"); and/or the second polymer is a copolymer or block polymer of PE and PP; and/or the second polymer is a polyurethane, an acrylic, a polyester, a polyamide, a polyimide, a vinyl acetate, an alkyd, an epoxy, a silane, or a siloxane; and/or the coating is composed of between 1 and 20 coating layers having a total coating thickness of between about 5 μm and about 50 μm.

According to yet a further embodiment of the disclosure, an uncoated woven fabric leaflet for a prosthetic replacement heart valve comprises:

a piece of woven polymer fabric comprising a first major surface, a second major surface, an attachment edge and a free edge, said polymer fabric composed of polyethylene ("PE"), polypropylene ("PP") or polytetrafluoroethylene ("PTFE") fibers and having a thread count of 300-500×100-300 fibers per square inch, a thickness of between about 10 μm and about 200 μm, and an areal density of no more than about 1.0 ounces/yard$^2$; and/or indicia composed of a radiopaque fiber forming a portion of the woven polymer fabric; and/or at least one grommet in the woven polymer fabric adjacent the attachment edge; and/or a plurality of tabs disposed on the woven polymer fabric adapted to form of commissures; and/or at least one grommet is disposed in each of the plurality of tabs; and/or the polymer fabric is composed of PE or PTFE fibers and has a thread count of 300-500×100-300 fibers per square inch, a thickness of between about 50 μm to 100 μm, and a areal density of about 0.65 ounces/yard$^2$ or greater.

According to another aspect of the disclosure, a coated woven fabric leaflet for a prosthetic replacement heart valve comprises:

a piece of woven polymer fabric comprising a first major surface and an opposed second major surface, an attachment edge and a free edge, said polymer fabric composed of polyethylene ("PE"), polypropylene ("PP") or polytetrafluoroethylene ("PTFE") fibers and having a thread count of 300-500×100-300 fibers per square inch, a thickness of between about 10 μm and about 200 μm, and an areal density of no more than about 1.0 ounces/yard$^2$; and a coating disposed on at least one of the first major surface and the second major surface, the coating composed of PE, PP or PTFE, wherein the piece of woven polymer fabric, including the coating, has a thickness no greater than about 250 μm; and/or indicia composed of a radiopaque fiber forming a portion of the woven fabric; and/or at least one grommet in the woven polymer fabric adjacent the attachment edge; and/or a plurality of tabs disposed on the woven polymer fabric adapted to form of commissure; and/or at least one grommet disposed in each of the plurality of tabs; and/or the coating coats less than an entirety of the at least one of the first major surface and the second major surface; and/or the coating is disposed adjacent the free edge of the leaflet; and/or the coating is disposed adjacent the attachment edge of the leaflet; and/or the coating is disposed adjacent the attachment edge of the first major surface and adjacent the free edge of the second major surface; and/or the coating forms ribs emanating from either the attachment edge or the free edge of the leaflet; and/or radiopaque indicia disposed between the coating and the fabric; and/or at least one grommet disposed through the fabric and the coating adjacent the attachment edge; and/or the polymer fabric is composed of PE or PTFE fibers and has a thread count of 300-500×100-300 fibers per square inch, a thickness of between about 50 μm to 100 μm, and an areal density of about 0.65 ounces/yard² or more, and the coating is composed of PE or PTFE; and/or the coating is disposed adjacent the attachment edge, the free edge, or both.

According to a further aspect of the disclosure, a valve assembly comprises:

a cuff; and three prosthetic leaflets sutured or laced to the cuff, each leaflet composed of an uncoated piece of woven polymer fabric having a first major surface, a second major surface, an attachment edge, a free edge, and a plurality of tabs, wherein the polymer fabric is composed of polyethylene ("PE"), polypropylene ("PP") or polytetrafluoroethylene ("PTFE") fibers and has a thread count of 300-500×100-300 fibers per square inch, a thickness of between about 10 μm and 200 μm, and an areal density of no more than about 1.0 ounces/yard²; and/or three commissures formed by tabs of adjacent ones of the three leaflets being sutured or laced together.

According to an aspect of the disclosure, a prosthetic valve assembly comprises:

a cuff; and three prosthetic leaflets sutured or laced to the cuff, each leaflet composed of an uncoated piece of woven polymer fabric having a first major surface, a second major surface, an attachment edge, a free edge and a plurality of tabs, the polymer fabric being composed of polyethylene ("PE") or polytetrafluoroethylene ("PTFE") fibers and having a thread count of 300-500×100-300 fibers per square inch, a thickness of between about 50 μm and 100 μm, and an areal density of more than about 0.65 ounces/yard; and a coating disposed on at least one of the first major surface and the second major surface, the coating being composed of PE or PTFE, woven polymer fabric and the coating together having a thickness no greater than about 250 μm; and/or three commissures formed by tabs of adjacent ones of the three prosthetic leaflets being sutured or laced together; and/or the coating is disposed on the attachment edge, the free edge, or both; and/or a grommet disposed in the woven polymer fabric adjacent the attachment edge; and/or the coating is a single layer the at least one of the first major surface and the second major surface; and/or the coating has a thickness of between about 2 μm and about 50 μm; and/or the coating has a thickness of between about 5 μm and about 25 μm; and/or the coating contains a plurality of layers on the at least one of the first major surface and the second major surface; and/or the total thickness of the plurality of layers of coating is between about 2 μm and about 50 μm; and/or the total thickness of the plurality of layers of coating is between about 5 μm and about 25 μm; and/or the coating is formed as a single layer on each of the first major surface and the second major surface; and/or each single layer of coating has a thickness of between about 2 μm and about 50 μm; and/or each single layer of coating has a thickness of between about 5 μm and about 25 μm.

According to still another aspect of the disclosure, an uncoated knitted fabric leaflet for a prosthetic heart valve comprises:

a piece of knitted polymer fabric comprising a first major surface, a second major surface, an attachment edge and a free edge, the polymer fabric composed of polyethylene ("PE"), polypropylene ("PP"), or polytetrafluoroethylene ("PTFE") fibers and having a stitch density of between about 2 and about 750 loops per square inch (Wales density× courses per inch) and a thickness of between about 10 μm and about 200 μm.

According to a further embodiment of the disclosure, a coated knitted fabric leaflet for a prosthetic heart valve comprises:

a piece of knitted polymer fabric comprising a major surface and an opposed major surface, an attachment edge and a free edge, the polymer fabric composed of polyethylene ("PE"), polypropylene ("PP"), or polytetrafluoroethylene ("PTFE") fibers and having a stitch density of between about 2 and about 750 loops per square inch and a thickness of between about 10 μm to 200 μm; and at least one coating disposed on at least one of the major surface and the opposed major surface, the at least one coating composed of PE, PP or PTFE, wherein the at least one coating has a total thickness of between about 2 μm and about 50 μm, such that the coated knitted fabric has a total thickness no greater than about 250 μm.

According to yet a further aspect of the disclosure, a prosthetic valve assembly comprises:

a cuff; and three prosthetic leaflets sutured or laced to the cuff, at least one of the cuff and the prosthetic leaflets composed of an uncoated piece of knitted polymer fabric comprising a first major surface, a second major surface, an attachment edge, a free edge and a plurality of tabs, the polymer fabric being composed of polyethylene ("PE"), polypropylene ("PP"), or polytetrafluoroethylene ("PTFE") fibers and having a stitch density of between about 2 and about 750 loops per square inch, and a thickness of between about 10 μm and about 200 μm.

According to a further aspect of the disclosure; a prosthetic valve assembly comprises:

a cuff; and three prosthetic leaflets sutured or laced to the cuff, at least one of the cuff and the leaflets composed of a coated piece of knitted polymer fabric comprising a first major surface, a second major surface, an attachment edge, a free edge and a plurality of tabs, the polymer fabric composed of polyethylene ("PE"), polypropylene ("PP"), or polytetrafluoroethylene ("PTFE") fibers and having a stitch density of between about 2 and about 750 loops per square inch, a thickness of between about 10 µm and about 200 µm, and at least once coating composed of PE, PP or PTFE, the at least one coating having a total thickness of between about 2 µm and about 50 µm.

According to an aspect of the disclosure, a process for assembling a medical device comprises:

lacing a fiber through a grommet provided in a first coated or uncoated woven or knitted polymer fabric; and attaching the first coated or uncoated woven or knitted polymer fabric to a stent, superstructure, support or a second coated or uncoated woven or knitted polymer fabric using the fiber; and/or the first coated or uncoated woven or knitted polymer fabric is attached to the second coated or uncoated woven or knitted polymer fabric; and/or the first coated or uncoated woven or knitted polymer fabric is also attached to the stent.

According to another aspect of the disclosure, a prosthetic heart valve comprises:

an expandable stent;

a prosthetic leaflet having a first major surface and a second opposed major surface; and a cuff having a first major surface and a second opposed major surface, the prosthetic leaflet being attached to both the stent and the cuff, the prosthetic leaflet and the cuff both being composed of a woven polymer fabric, at least a portion of one of the first major surfaces and the second opposed major surfaces of the leaflet or the cuff being coated with at least one layer of a bio-absorbable or biodegradable polymer coating; and/or the at least one layer of the bio-absorbable or biodegradable polymer coating is selected from the group consisting of: poly-glycolic acid, poly-L-lactic acid, copolymers of poly-glycolic acid, poly-L-lactic acid, polycaprolactone, poly-DL lactic acid, polytrimethylene carbonate, polydioxanone, poliglecaprone and polyglactin; and/or the at least one layer of the bio-absorbable or biodegradable polymer coating has a total thickness of up to about 100 µm; and/or the at least one layer of a bio-absorbable or biodegradable polymer coating has a total thickness of between about 2 µm and about 50 µm; and/or the at least one layer of a bio-absorbable or biodegradable polymer coating is provided in a thickness sufficient to delay tissue growth on the coated surface.

Although the present disclosure has been made with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims. For example, features of one embodiment described above may be combined with features of other embodiments described above.

The invention claimed is:

1. A prosthetic heart valve, comprising:
an expandable stent extending in a longitudinal direction between an inflow end and an outflow end;
a cuff coupled to a luminal surface of the stent;
a plurality of prosthetic leaflets formed separately from the cuff and coupled to at least one of the cuff and the stent and having an open condition and a closed condition, the plurality of prosthetic leaflets adapted to allow blood to flow from the inflow end toward the outflow end when in the open condition and to retard blood from flowing from the outflow end toward the inflow end when in the closed condition, each of the plurality of leaflets being formed of a fabric and having a free edge adapted to move as the prosthetic leaflets transition between the open condition and the closed condition, an attachment edge directly attached by sutures to at least one of the cuff or the stent, and a first major surface opposite a second major surface, the first major surface generally facing the outflow end of the stent in the closed condition and the second major surface generally facing the inflow end of the stent in the closed condition,
wherein the fabric has a first group of fibers extending in a first direction of the fabric and a second group of fibers extending in a second direction of the fabric different than the first direction, the first group of fibers and the second group of fibers being interlaced in an ordered arrangement, the first group of fibers and the second group of fibers both being composed of ultra-high molecular weight polyethylene (UHMWPE), at least one layer of the fabric having a thread count of between about 300 and about 500 fibers by between about 100 and about 300 fibers per square inch, the fabric having a thickness of between about 50 µm and about 100 µm, and when each of the plurality of leaflets is in a flattened condition, the first group of fibers extend in the first direction at an angle of between about 30 degrees and about 60 degrees relative to a line that extends perpendicular to the free edge; and
a nonwoven polymer coating on at least one of the first major surface or the second major surface of each of the plurality of leaflets adjacent the attachment edge so that the sutures extend through the nonwoven polymer coating, wherein at least some portion of the first major surface is not coated by the nonwoven polymer coating and at least some portion of the second major surface is not coated by the nonwoven polymer coating, the nonwoven polymer coating applied to a prosthetic leaflet forming a coated leaflet portion, the strength of the coated leaflet portion being greater than the strength of the fabric.

2. The prosthetic heart valve of claim 1, wherein the fabric is a woven fabric.

3. The prosthetic heart valve of claim 1, wherein the fibers of the first group of fibers are coated with a first polymer coating, and the fibers of the second group of fibers are coated with a second polymer coating.

4. The prosthetic heart valve of claim 1, wherein the fabric has a tensile strength of between about 50 N and about 100 N.

5. The prosthetic heart valve of claim 1, wherein the fabric has an areal density of between about 0.5 ounces/yard$^2$ and about 1.0 ounces/yard$^2$.

6. The prosthetic heart valve of claim 1, wherein each fiber in the first group of fibers is formed of a plurality of UHMWPE filaments, and each fiber in the second group of fibers is formed of a plurality of UHMWPE filaments.

7. The prosthetic heart valve of claim 1, wherein the cuff is formed of a second fabric, the second fabric having a third group of fibers extending in a first direction of the second fabric and a fourth group of fibers extending in a second direction of the second fabric different than the first direction of the second fabric, the third group of fibers and the fourth group of fibers being interlaced in an ordered arrangement, the third group of fibers and the fourth group of fibers both being composed of UHMWPE, at least one layer of the second fabric having a thread count of between about 300 and about 500 fibers by between about 100 and about 300 fibers per square inch, the second fabric having an areal density of between about 0.5 ounces/yard$^2$ and about 1.0 ounces/yard$^2$.

8. The prosthetic heart valve of claim 7, wherein the second fabric is a woven fabric.

9. The prosthetic heart valve of claim 7, wherein the third group of fibers extend in the first direction of the second fabric at an angle of between about 30 degrees and about 60 degrees relative to the longitudinal axis of the stent when the stent is in an expanded condition.

10. The prosthetic heart valve of claim 1, wherein the nonwoven polymer coating is formed of UHMWPE.

11. The prosthetic heart valve of claim 1, wherein the nonwoven polymer coating is disposed on the first major surface adjacent the attachment edge.

12. The prosthetic heart valve of claim 11, wherein the nonwoven polymer coating is disposed adjacent the attachment edge on the second major surface, at least some other portions of the second major surface remain uncoated by the nonwoven polymer coating, the nonwoven polymer coating is disposed adjacent the free edge on the first major surface, and at least some other portions of the first major surface remain uncoated by the nonwoven polymer coating.

13. The prosthetic heart valve of claim 1, wherein portions of the second major surface adjacent the free edge are coated by the nonwoven polymer coating, at least some other portions of the second major surface remain uncoated by the nonwoven polymer coating, and portions of the first major surface adjacent the free edge are not coated by the nonwoven polymer coating.

14. The prosthetic heart valve as claimed in claim 1, wherein the nonwoven polymer coating is disposed on the second major surface adjacent the attachment edge.

* * * * *